United States Patent [19]
Tanaka et al.

[11] Patent Number: 5,639,860
[45] Date of Patent: Jun. 17, 1997

[54] ENDOTHELIN-ANTAGONIZING PEPTIDE

[75] Inventors: Takeo Tanaka; Yoshikazu Morishita, both of Machida; Mika Makino, Muroran; Shigeru Chiba, Kawasaki; Isao Kawamoto, Hiratsuka; Eiji Tsukuda, Sunto-gun; Mayumi Yoshida, Sagamihara; Chieko Bando, Machida; Kazuo Yamaguchi, Sagamihara; Yuzuru Matsuda, Koganei; Shigeto Kitamura, Machida; Toshihide Ikemura, Mishima; Tatsuhiro Ogawa; Keiichi Yano, both of Kawasaki; Toshiyuki Suzawa, Yamato; Kenji Shibata, Kawasaki; Motoo Yamasaki, Machida, all of Japan

[73] Assignee: Kyowa Hakko Kogyo Co., Ltd., Tokyo, Japan

[21] Appl. No.: 321,625

[22] Filed: Oct. 12, 1994

Related U.S. Application Data

[63] Continuation-in-part of Ser. No. 108,612, Aug. 27, 1993, abandoned.

[30] Foreign Application Priority Data

Dec. 27, 1991 [JP] Japan ................... 3-347293

[51] Int. Cl.⁶ .............................. A61K 38/10
[52] U.S. Cl. .................. 530/326; 530/317; 530/327; 530/328; 530/329
[58] Field of Search ............... 530/326, 327, 530/328, 329, 317; 514/13

[56] References Cited

PUBLICATIONS

Uchida, Bioch Biophys Res Commun 183, 1197–1202, 1992.

*Primary Examiner*—Cecilia J. Tsang
*Assistant Examiner*—David Lukton
*Attorney, Agent, or Firm*—Antonelli, Terry, Stout & Kraus, LLP

[57] ABSTRACT

Peptides represented by the following formula (I):

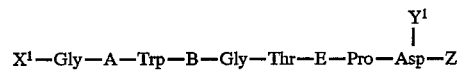

wherein A represents Asn or Asp; B represents His or Lys; and E represents Ala or Ser;

(1) $X^1$ and $Y^1$ are combined together to form a single bond as $X^1$—Y1, or (2) $X^1$ represents hydrogen and $Y^1$ represents hydroxy;

and Z represents, in case of (1),

Trp-Phe-Phe-Asn-Tyr-Tyr-7Hyt-$Z^1$
Trp-Val-Tyr-Phe-Ala-His-Leu-Asp-Ile-Ile-Trp-$Z^1$,
Trp-Val-Tyr-Tyr-Ala-His-Leu-Asp-Ile-Ile-Trp-$Z^1$,
Trp-Leu-Tyr-Phe-Ala-His-Gln-Asp-Val-Ile-Trp-$Z^1$,
Trp-Phe-Phe-Asn-Tyr-R-T-$Z^1$ wherein $Z^1$ is an organic moiety, wherein R is Tyr or a covalent bond, T is Trp, Ala, Phe, Tyr, Trp-Trp, Asn-Tyr-Tyr-Trp, Trp-Asn-Tyr-Tyr-Trp, Trp-Val-Tyr-Phe-Ala-His-Leu-Asp-Ile-Ile-Trp, or in case of (2), Z represents Trp-Val-Tyr-Phe-Ala-His-Leu-Asp-Ile-Ile-Trp-$Z^1$
Trp-Val-Tyr-Tyr-Ala-His-Leu-Asp-Ile-Ile-Trp-$Z^1$
Trp-Leu-Tyr-Phe-Ala-His-Gln-Asp-Val-Ile-Trp-$Z^1$.

These peptides have endothelin-antagonizing activity, and are useful for treating hypertension, asthma, cerebral apoplexy, angina pectoris, acute renal failure, cardiac infarction and cerebral vasospasm.

4 Claims, No Drawings

ENDOTHELIN-ANTAGONIZING PEPTIDE

CROSS REFERENCE TO RELATED PATENT APPLICATION

This application is a continuation-in-part of U.S. Ser. No.: 08/108,612 filed Aug. 27, 1993, now abandoned.

FIELD OF THE INVENTION

The present invention relates to a novel peptide which has endothelin-antagonizing activity, and an intermediate for its synthesis. The peptide has excellent endothelin-antagonizing activity, and is therefore useful for treatment of hypertension, asthma, cerebral apoplexy, angina pectoris, acute renal failure, cardiac infarction, cerebral vasospasm, etc.

BACKGROUND OF THE INVENTION

Endothelin is a cyclic peptide which possesses a strong, long-lasting vasoconstricting effect, and is thought to be one of the substances responsible for hypertension, asthma, acute renal failure, cardiac infarction, cerebral apoplexy, angina pectoris and cerebral vasospasm. Consequently, a substance which antagonizes endothelin and inhibits its effects is expected to be useful for the treatment and prevention of these diseases.

It is known that the cyclic peptide represented by the formula (A) SEQ ID NO:1

$$\boxed{U-Leu-D-Trp(R')-D-Glu(OR^2)-Ala} \quad (A)$$

(wherein U represents D-Val or D-allo-Ile, $R^1$ represents hydrogen or an amino-protective group, and $R^2$ represents hydrogen or a carboxyl-protective group) exhibits the endothelin antagonism (Japanese Published Unexamined Patent Application No. 130299/91).

DISCLOSURE OF THE INVENTION

The present inventors have made a screening of numerous substances produced by microorganisms in order to find a naturally occurring physiologically active substance having endothelin-antagonizing activity, have succeeded in isolating substances from the cultures of microorganisms belonging to the genus Streptomyces newly isolated from the soil, which substances have endothelin-antagonizing activity and a suppressing effect on the increase in intracellular calcium and intracellular guanosine-3',5'-cyclic monophosphate concentrations due to endothelin, and have named the substances Compound (I-1), Compound (I-2) and Compound (I-3). As the result of further investigations, the present inventors have successfully determined the structure of these substances, have synthesized novel derivatives of these substances, and thus have completed the present invention.

According to the present invention, there is provided a peptide compound represented by the following formula (I):

X-A-Trp-B-Gly-Thr-E-G-Y   (I) SEQ ID NO:2 wherein
A represents Asn or Asp;
B represents His or Lys;
E represents Ala or Ser;
G represents Ala or Pro;

X represents X1-Gly or $$X^3-\underset{\underset{X^2}{|}}{Cys};$$

Y represents hydroxy, lower alkoxy, amino, $$\underset{Asp-Z}{\overset{Y^1}{|}} \text{ or } \underset{Cys-Z}{\overset{Y^2}{|}}$$

wherein
each of $X^1$ and $X^3$ represents hydrogen, benzyloxycarbonyl, t-butyloxycarbonyl or 9-fluorenylmethyloxycarbonyl, or carbonyl-substituted or unsubstituted lower alkanoyl;
each of $X^2$ and $Y^2$ represents hydrogen;
$Y^1$ represents hydroxy, lower alkoxy or amino; or
$X^1$ and $Y^1$, or $X^2$ and $Y^2$ are combined together to form a single bond as $X^1$-$Y^1$ or $X^2$-$Y^2$; and
Z represents hydroxy, lower alkoxy, benzyloxy, benzhydryloxy, amino,

[structure: indole with CH₂CH₂NH—]

[structure: naphthalene with CH₂]

—NHCHCO—Z² where
$Z^2$ is hydroxy, lower alkoxy, benzyloxy, benzhydryloxy or amino,

Gly-Z¹ where $Z^1$ is hydroxy, lower alkoxy, benzyloxy, benzhydryloxy, amino,

[structure: indole with CH₂CH₂NH—]

or

[structure: naphthalene with CH₂]

—NHCHCO—Z² where $Z^2$ is as defined previously, or $Z^1$ is combined with $X^1$ to form a single bond as $X^1$-$Z^1$, Ala-Z¹ where $Z^1$ is as defined previously,

Val-Z¹ where $Z^1$ is as defined previously,

Trp-$Z^1$ where $Z^1$ is as defined previously,

Trp-Gly-$Z^1$ where $Z^1$ is as defined previously,

Trp-Asn-Tyr-Tyr-Trp-$Z^1$ where $Z^1$ SEQ ID NO:3 is as defined previously,

Trp-Phe-Phe-Asn-Tyr-Tyr-7Hyt-$Z^1$    SEQ ID NO:4 where $Z^1$ is as defined previously, and 7Hyt represents 7-hydroxytryptophan,

Trp-Ile-Ile-Trp-$Z^1$    SEQ ID NO:5 where $Z^1$ SEQ ID NO:6 is as defined previously,

Trp-Val-Tyr-Phe-W-His-Leu-Asp-Ile-Ile-Trp-$Z^1$ where $Z^1$ is as defined previously and W represents Ala, Ser or Cys, Trp-W-His-Leu-Asp-Ile-Ile-Trp-$Z^1$    SEQ ID NO:7 where $Z^1$ and W are as defined previously,

Trp-Val-Tyr-Tyr-W-His-Leu-Asp-Ile-Ile-Trp-$Z^1$    SEQ ID NO:8 where $Z^1$ and W are as defined previously,

Trp-Leu-Tyr-Phe-W-His-Gln-Asp-Val-Ile-Trp-$Z^1$    SEQ ID NO:9 where $Z^1$ and W are as defined previously,

Trp-Val-Tyr-Phe-W-Phe-Phe-Asn-Tyr-Tyr-Trp-$Z^1$    SEQ ID NO:10 where Z1 and W are as defined previously,

Trp-Phe-Phe-Asn-Tyr-Tyr-W-His-Leu-Asp-Ile-Ile-Trp-$Z^1$    SEQ ID NO:11 where $Z^1$ is as defined previously,

Trp-Phe-Phe-Asn-Tyr-Tyr-Asn-Ile-Ile-Trp-$Z^1$    SEQ ID NO:12 where $Z^1$ is as defined previously,

J-Phe-M-Q-Tyr-R-T-$Z^1$    SEQ ID NO:13 where
J is Trp or a single bond,
M is Phe or a single bond,
Q is Asn or a single bond,
R is Tyr or a single bond,
T is Trp,
  Ala,
  Phe,
  Tyr,
  Trp-Trp, SEQ ID NO:14
  Asn-Tyr-Tyr-Trp, SEQ ID NO:15
  Trp-Asn-Tyr-Tyr-Trp,
  Trp-Val-Tyr-Phe-W-His-Leu-Asp-Ile-Ile-Trp, SEQ ID NO:16
  where W is as defined previously, or a single bond,
2 or more of J, M, Q, R and T are not a single bond simultaneously, and $Z^1$ is as defined previously, or a pharmaceutically acceptable salt thereof.

Also, according to the present invention there is provided an intermediate represented by the following formula (II):

$X^4$-J-Phe-M-Q-Tyr-R-T-$Z^3$    (II) SEQ ID NO:17 wherein $X^4$ represents hydrogen or benzyloxycarbonyl, t-butyloxycarbonyl or 9-fluorenylmethyloxycarbonyl, $Z^3$ represents hydroxy, lower alkoxy, benzyloxy or benzhydryloxy, and J, M, Q, R and T are as defined previously, which is useful for the synthesis of a peptide compound represented by the formula (I).

The peptide compound represented by the above formula (I) is referred to as Compound (I), and compounds represented by the other formulas are similarly referred to.

In the definitions for the above formulas (I) and (II), the lower alkyl and the alkyl moiety in lower alkoxy mean linear or branched alkyl having 1–6 carbon atoms, for example methyl, ethyl, propyl, isopropyl, butyl, isobutyl, sec-butyl, tert-butyl, pentyl, neopentyl, hexyl and isohexyl. The lower alkanoyl means those having linear or branched 1–6 carbon atoms, such as formyl, acetyl, propionyl, butyryl, valeryl, pivaloyl and pentanoyl.

As the pharmaceutically acceptable salt of Compound (I), mention may be made of an acid addition salt, a metal salt and an organic base addition salt. Specifically, the pharmaceutically acceptable acid addition salt includes, for example, inorganic acid salts such as hydrochloride, sulfate, phosphate, etc. and organic acid salts such as acetate, maleate, fumarate, tartrate, citrate, etc. The pharmaceutically acceptable metal salt includes, for example, alkali metal salts such as sodium salt, potassium salt, etc., alkaline earth metal salts such as magnesium salt, calcium salt, etc., aluminum salt, zinc salt, etc. The pharmaceutically acceptable organic base addition salt includes, for example, primary amines such as methylamine, ethylamine, aniline, etc., secondary amines such as dimethylamine, diethylamine, pyrrolidine, piperidine, morphopline, piperazine, etc., tertiary amines such as trimethylamine, triethylamine, N,N-dimethylaniline, pyridine, etc. and ammonia, etc.

The method for producing compounds (I) and (II) is given below.

Of Compound (I), Compound (I-1), Compound (I-2) or Compound (I-3) having the structures listed below is produced by culturing in a medium a microorganism belonging to the genus Streptomyces capable of producing Compound (I-1), Compound (I-2) or Compound (I-3) to form and accumulate Compound (I-1), Compound (I-2) or Compound (I-3) in the culture, and recovering Compound (I-1), Compound (I-2) or Compound (I-3) therefrom.

Compound (I-1)

⌐ Gly—Asn—Trp—His—Gly—Thr—Ala—Pro—Asp
—Trp—Phe—Phe—Asn—Tyr—Tyr—Trp—OH

SEQ ID NO:18

Compound (I-2)

⌐ Gly—Asn—Trp—His—Gly—Thr—Ala—Pro—Asp
—Trp—Phe—Phe—Asn—Tyr—Tyr—7Hyt—OH

SEQ ID NO:19

-continued

Compound (I-3)

Gly—Asn—Trp—His—Gly—Thr—Ser—Pro—Asp—Trp—Phe—Phe—Asn—Tyr—Tyr—Trp—OH

SEQ ID NO:20

The specific preferred microorganism is an actinomyces such as Streptomyces sp. RE-701 which was isolated by the present inventors from the soil in the areas of Kitashitara-gun, Aichi; and Streptomyces sp. RE-629 which was isolated by the present inventors from the soil in the areas of Tsuno-gun, Yamaguchi.

The bacteriological properties of Streptomyces sp. RE-701 strain are described below.

I. Morphology

In a usual agar medium, the strain RE-701 possesses a septum and forms branched aerial mycelia and substrate mycelia. Characteristic fragmentation of the substrate mycelia is not observed. Also, there is no formation of sporangia or sclerotia.

Chains of more than 10 spores form as the end of sporophores simply branched from the aerial mycelium, and the shapes are open loops or spirals. The mature spores are oval of size 0.4–0.5 μm×0.6–0.8 μm with a smooth surface and without flagella.

II. Growth conditions on various media

The strain RE-701 grows normally or vigorously, forming grayish aerial mycelia on usual synthetic and natural media. The substrate mycelia exhibit a grayish-white to brown color. Soluble pigments are not produced.

The growth and color characteristics of the strain RE-701 when cultured in various media at 28° C. for 10 days are shown below. The color indications follow the classifications in the Color Harmony Manual, Container Corporation of America.

1. Glucose-asparagine agar medium
   Growth, reverse side color: moderate, putty (1½ ec)
   Aerial mycelia: moderate, white (a)
   Soluble pigment: none
2. Glycerol-asparagine agar medium
   Growth, reverse side color: Poor, oyster white (b)
   Aerial mycelia: somewhat poor, white (a)
   Soluble pigment: none
3. Sucrose-nitrate agar medium
   Growth, reverse side color: good, putty (1½ ec)
   Aerial mycelia: moderate, gray (f)
   Soluble pigment: none
4. Starch-inorganic salt agar medium
   Growth, reverse side color: good, light antique gold (1½ ic)
   Aerial mycelia: abundant, gray (g)
   Soluble pigment: none
5. Tyrosine agar medium
   Growth, reverse side color: poor, light tan (3 gc)
   Aerial mycelia: poor, light beige (3 ec)
   Soluble pigment: none
6. Nutrient agar medium
   Growth, reverse side color: moderate, honey gold (2 ic)
   Aerial mycelia: somewhat poor, white (a)
   Soluble pigment: none
7. Malt extract-yeast extract agar medium,
   Growth, reverse side color: good, mustard gold (2 ne)
   Aerial mycelia; moderate, white (a)
   Soluble pigment: none
8. Oatmeal agar medium
   Growth, reverse side color: somewhat good, white (1½ lg)
   Aerial mycelia: poor, charcoal gray (o)
   Soluble pigment: none III. Physiological properties The physiological properties of the strain RE-701 are described below. The growth temperature range indicates the results obtained by observation for 6 days. With respect to the other items, the results obtained by observation for 2 weeks at 28° C. are shown.

(1) Carbon utilization: A Pridham and Gottlieb inorganic medium (ISP No. 9) was used as a basal medium.

The strain RE-701 assimilates D-glucose, D-fructose, sucrose, inositol, raffinose and D-mannitol, but do not assimilate D-arabinose and L-rhamnose. The assimilation of D-xylose is uncertain.

(2) Effects on milk: coagulation, no liquefaction
(3) Hydrolysis of starch: positive
(4) Growth temperature range: 7°–41° C.
(5) Formation of melanoid pigments: negative
(6) Liquefaction of gelatin: negative IV. Cell wall composition In analysis for diaminopimelic acid by hydrolysis of the whole cells, only LL-diaminopimelic acid was detected.

The strain is classified in the genus Streptomyces of Actinomycetales, on the basis of the spore chains' formation on the aerial mycelia and the configuration of diaminopimelic acid, etc.

Therefore, the strain was named as Streptomyces sp. RE-701, and has been deposited with the Fermentation Research Institute, Agency of Industrial Science and Technology under FERM BP-3624, as of Oct. 29, 1991.

The bacteriological characteristics of Streptomyces sp. RE-629 are described below.

I. Morphology

In a usual agar medium, the strain RE-629 possesses a septum and form branched aerial mycelia and substrate mycelia. Characteristic fragmentation of the substrate mycelia is not observed. Also, there is no formation of sporangia or sclerotia.

Chains of more than 10 spores form at the end of sporophores simply branched from the aerial mycelium, and the shapes are open loops or spirals. The mature spores are oval of size 0.7–0.8 μm×0.7–1.0 μm with a smooth surface and without flagella.

II. Growth conditions on various media

The strain RE-629 grows normally or vigorously, forming grayish aerial mycelia on usual synthetic and natural media. The substrate mycelia exhibit a grayish-white to brown color. Brownish soluble pigments are produced on specific media.

The growth and color characteristics of the strain RE-629 on various media at 28° C. after 14 days are shown below. The color indications follow the classifications in the Color Harmony Manual, Container Corporation of America.

1. Glycerol-asparagine agar medium
   Growth, reverse side color: good, bamboo (2 gc)
   Aerial mycelia; good, natural (2 dc)
   Soluble pigment: none
2. Starch-inorganic salt agar medium
   Growth, reverse side color: good, dull gold (2 ng)
   Aerial mycelia: abundant, silver gray (3 fe)
   Soluble pigment: present 3. Malt extract-yeast extract agar medium
Growth, reverse side color: Good, oak brown (4 pi)
Aerial mycelia: good, silver gray (3 fe)
Soluble pigment: present
4. Oatmeal agar medium
Growth, reverse side color: moderate, olive (1½ pl)
Aerial mycelia: moderate, lamp black (o)
Soluble pigment: present III. Physiological properties The physiological properties of the strain RE-629 are described below. The growth temperature range indicates the results obtained by observation for 5 days. With respect to the other items, the results obtained by observation for 2 weeks at 28° C. are shown.

(1) Carbon utilization: A Pridham and Gottlieb inorganic medium (ISP No. 9) was used as the basal medium. The strain RE-629 assimilates D-glucose, D-fructose, sucrose, inositol, raffinose, D-mannitol and D-xylose, but does not assimilate L-rhamnose. The assimilation of D-arabinose is uncertain.

(2) Growth temperature range: 13°–43° C.

(3) Formation of melanoid pigments:
 (a) peptone/yeast/iron agar culture: none
 (b) tyrosine agar culture: none IV. Cell wall composition In analysis for diaminopimelic acid by hydrolysis of the whole cells, only LL-diaminopimelic acid was detected.

The strain is classified in the genus Streptomyces of Actinomycetales, on the basis of the spore chains' formation on the aerial mycelia and the configuration of diaminopimelic acid, etc.

Therefore, the strain was named as Streptomyces sp. RE-629, and has been deposited with the Fermentation Research Institute, Agency of Industrial Science and Technology under FERM BP-4126, as of Dec. 17, 1992.

For the culturing of the strains RE-701, and RE-629, a method usually used for the culturing of Actinomycetes is used. As the medium for culturing, either a natural medium or a synthetic medium can be used so long as it appropriately contains carbon sources, nitrogen sources, inorganic materials, etc. which may be assimilated by the cells.

As the carbon source, a carbohydrate such as glucose, fructose, sucrose, stabirose, starch, dextrine, mannose, maltose and molasses; an organic acid such as citric acid, malic acid, acetic acid and fumaric acid; an alcohol such as methanol and ethanol; a hydrocarbon such as methane, ethane, propane and n-paraffin; an amino acid such as glutamic acid; and glycerol can be used.

As the nitrogen source, an ammonium salt such as ammonium chloride, ammonium sulfate, ammonium nitrate and ammonium phosphate, an amino acid such a aspartic acid, glutamine, cystine or alanine; and urea, peptone, meat extract, yeast extract, dry yeast, corn steep liquor, soybean powder, cottonseed lees, soybean casein, Casamino acid, pharmamedia (product of Procter and Gamble, U.S.A.), etc. can be used.

As the inorganic material, dipotassium hydrogen phosphate, potassium dihydrogen phosphate, sodium dihydrogen phosphate, magnesium sulfate, ferrous sulfate, manganese sulfate, copper sulfate, cobalt sulfate, zinc sulfate, calcium pantothenate, ammonium molybdate, aluminum potassium sulfate, barium carbonate, calcium carbonate, cobalt chloride, sodium chloride, etc. can be used.

In addition, vitamins such as thiamine, and other substances may be added as necessary to the culture medium in order to stimulate the production of Compound (I-1), Compound (I-2) or Compound (I-3).

When the microorganism utilized requires a specific substance, it is of course necessary to supplement the culture with the requisite substance.

Culturing is carried out by shaking culture, aeration stirring culture, etc. at 20°–40° C. and at a near neutral pH. Culturing is discontinued after 3 to 7 days, when the maximum amount of Compound (I-1), Compound (I-2) or Compound (I-3) is accumulated in the culture.

For isolation of the accumulated Compound (I-1), Compound (I-2) and Compound (I-3) from the culture, the ordinary method for isolating a physiologically active substance from cultures is used. Separation and collection of the Compound (I-1), Compound (I-2) and Compound (I-3) accumulated in the cells are carried out in a conventional manner as used for recovering the physiologically active substances from cells. For example, the cells are collected from the culture by filtration and centrifugation, and extracted with an organic solvent such as methanol, acetone, etc. Then the extract may be purified by partition chromatography, column chromatography or thin-layer chromatography using an adsorbent resin, silica gel, chemically modified silica gel, reverse phase silica gel, alumina, cellulose, diatomaceous earth, magnesium silicate, ion-exchange resin and the like, or gel filtration, to give Compound (I-1), Compound (I-2) and Compound (I-3).

In the above-described procedure, Compound (I-1), Compound (I-2) and Compound (I-3) may be detected by development on silica gel thin-layer chromatography, coloring by an iodine reaction or spraying of 50% sulfuric acid thereto, and heating. Alternatively, the detection is carried out by measurement of the absorption at a 253.7 nm wavelength with high performance liquid chromatography (hereunder referred to as HPLC) by use of a C-18 reverse phase silica gel column.

Compounds (I) and (II), including the substances Compound (I-1), Compound (I-2) and Compound (I-3) which are produced by culture of said microorganism, may be produced by synthetic means.

That is, Compounds (I) and (II) according to the present invention can be synthesized with a peptide synthesizer manufactured by Applied Biosystems, Inc., U.S.A. (ABI Co.) or manufactured by Shimadzu Seisakusho, using an $N^\alpha$-t-butyloxycarbonylamino acid or an $N^\alpha$-9-fluorenylmethyloxycarbonylamino acid whose side chains have been appropriately protected, following the synthesis programs of the same companies.

In addition, the cyclic peptide in Compound (I) may be obtained by synthesizing a partial peptide whose side chains have been appropriately protected, with the above-mentioned synthesizer or according to the usual liquid phase peptide synthesis method ("Fundamentals and Experiments in Peptide Synthesis", Izumiya, N. et al., Maruzen) described below, using a condensing agent such as benzotriazole-1-yl-oxy-tris-pyrrolidinophosphonium hexafluorophosphate (PyBOP), etc. to obtain a cyclized partial peptide, and further using a peptide synthesizer or liquid phase synthesis method, or an appropriate combination of the two, condensing the C-terminal peptide with the cyclized partial peptide thus obtained. For the C-terminal peptide, Compound (II), for example, may be effectively used.

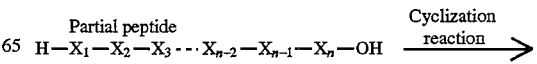

Partial peptide  Cyclization reaction
$H-X_1-X_2-X_3 \cdots X_{n-2}-X_{n-1}-X_n-OH \longrightarrow$

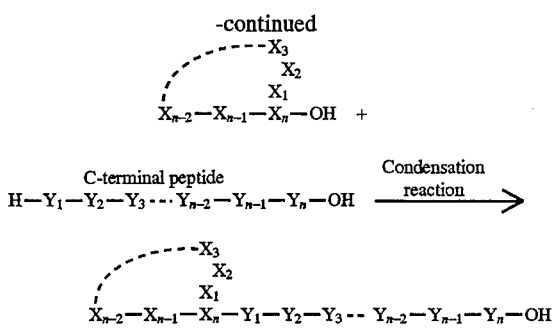

The protected amino acid which is a starting material for Compounds (I) and (II) may be obtained from ABI Co., Shimadzu Seisakusho, Kokusan Chemicals. Inc., Nova Biochem Co. or Peptide Laboratories, Inc.

The thus obtained Compounds (I) and (II) may be purified by HPLC using a reverse phase column or any of the above mentioned chromatography methods.

A conventional method is used to obtain a pharmaceutically acceptable salt of Compound (I). That is, an acid addition salt or an organic base addition salt of Compound (I) can be obtained by dissolving Compound (I) in an aqueous solution of the corresponding acid or organic base, and freeze-drying the solution. Also, a metal salt of Compound (I) can be obtained by dissolving Compound (I) in an aqueous solution containing the corresponding metal ion, and purifying it by gel filtration of HPLC.

Embodiments of Compounds (I) and (II) are shown below in Table 1.

| Compound Example | Amino Acid Sequence |
|---|---|
| Sequence | |
| I-1 (1),(5) | ⌐Gly—Asn—Trp—His—Gly—Thr—Ala—Pro—Asp—Trp—Phe—Phe—Asn—Tyr—Tyr—Trp—OH  SEQ ID NO:18 |
| I-2 (2) | ⌐Gly—Asn—Trp—His—Gly—Thr—Ala—Pro—Asp—Trp—Phe—Phe—Asn—Tyr—Tyr—7Hyt—OH  SEQ ID NO:19 |
| I-3 (3) | ⌐Gly—Asn—Trp—His—Gly—Thr—Ser—Pro—Asp—Trp—Phe—Phe—Asn—Tyr—Tyr—Trp—OH  SEQ ID NO:20 |
| I-4 (4) Sequence 1 | H—Gly—Asn—Trp—His—Gly—Thr—Ala—Pro—Asp—Trp—Phe—Phe—Asn—Tyr—Tyr—Trp—OH  SEQ ID NO:21 |
| I-5 (5) Sequence 2 | cyclo (Gly—Asn—Trp—His—Gly—Thr—Ala—Pro—Asp—Trp—Phe—Phe—Asn—Tyr—Tyr—Trp)  SEQ ID NO:22 |
| I-6 (6) Sequence 3 | H—Cys—Asn—Trp—His—Gly—Thr—Ala—Pro—Cys—Trp—Phe—Phe—Asn—Tyr—Tyr—Trp—OH  SEQ ID NO:23 |
| I-7 (7) | H—Cys—Asn—Trp—His—Gly—Thr—Ala—Pro—Cys—Trp—Phe—Phe—Asn—Tyr—Tyr—Trp—OH  SEQ ID NO:24 |
| I-8 (8) | CH$_3$CO—Cys—Asn—Trp—His—Gly—Thr—Ala—Pro—Cys—Trp—Phe—Phe—Asn—Tyr—Tyr—Trp—OH  SEQ ID NO:25 |
| II-9 (9) Sequence 4 | H—Trp—Phe—Phe—Asn—Tyr—Tyr—Trp—OH  SEQ ID NO:26 |
| II-10 (10) Sequence 5 | H—Trp—Phe—Asn—Tyr—Tyr—Trp—OH  SEQ ID NO:27 |
| II-11 (11) Sequence 6 | H—Trp—Phe—Phe—Asn—Tyr—Trp—OH  SEQ ID NO:28 |
| II-12 (12) Sequence 7 | H—Trp—Phe—Phe—Tyr—Tyr—Trp—OH  SEQ ID NO:29 |
| II-13 (13) Sequence 8 | H—Phe—Phe—Asn—Tyr—Tyr—Trp—OH  SEQ ID NO:30 |
| I-14 (14) | ⌐Gly—Asn—Trp—His—Gly—Thr—Ala—Pro—Asp—OH  SEQ ID NO:31 |

-continued

| Compound Example | Amino Acid Sequence |
|---|---|
| I-15 (15) | ⌐Gly—Asn—Trp—His—Gly—Thr—Ala—Pro—Asp—Trp—OH SEQ ID NO:32 |
| I-16 (16) | ⌐Gly—Asn—Trp—His—Gly—Thr—Ala—Pro—Asp—Gly—OCH₃ SEQ ID NO:33 |
| I-17 (17) | ⌐Gly—Asn—Trp—His—Gly—Thr—Ala—Pro—Asp—Trp—Phe—Phe—Asn—Tyr—Tyr—OH SEQ ID NO:34 |
| I-18 (18) | ⌐Gly—Asn—Trp—His—Gly—Thr—Ala—Pro—Asp—Trp—Phe—Phe—Asn—Tyr—Tyr—Trp—Trp—OH SEQ ID NO:35 |
| I-19 (19) | ⌐Gly—Asn—Trp—His—Gly—Thr—Ala—Pro—Asp—Trp—Phe—Phe—Asn—Tyr—Tyr—Trp—Asn—Tyr—Tyr—Trp—OH SEQ ID NO:36 |
| I-20 (20) | ⌐Gly—Asn—Trp—His—Gly—Thr—Ala—Pro—Asp—Trp—Phe—Phe—Asn—Tyr—Tyr—Trp—Val—Tyr—Phe—Ala—His—Leu—Asp—Ile—Ile—Trp—OH SEQ ID NO:37 |
| I-21 (21) | ⌐Gly—Asn—Trp—His—Gly—Thr—Ala—Pro—Asp—Trp—Phe—Phe—Asn—Tyr—Tyr—Ala—OH SEQ ID NO:38 |
| I-22 (22) | ⌐Gly—Asn—Trp—His—Gly—Thr—Ala—Pro—Asp—Trp—Phe—Phe—Asn—Tyr—Tyr—Phe—OH SEQ ID NO:39 |
| I-23 (23) | ⌐Gly—Asn—Trp—His—Gly—Thr—Ala—Pro—Asp—Trp—Phe—Phe—Asn—Tyr—Tyr—Tyr—OH SEQ ID NO:40 |
| I-24 (24) | ⌐Gly—Asn—Trp—His—Gly—Thr—Ala—Pro—Asp—Trp—Phe—Phe—Asn—Tyr—Tyr—Asn—Tyr—Tyr—Trp—OH SEQ ID NO:41 |
| I-25 (25) | ⌐Gly—Asn—Trp—His—Gly—Thr—Ala—Pro—Asp—Trp—Val—Tyr—Phe—Ala—His—Leu—Asp—Ile—Ile—Trp—OH SEQ ID NO:42 |
| I-26 (26) Sequence 9 | H—Gly—Asn—Trp—His—Gly—Thr—Ala—Pro—Asp—Trp—Val—Tyr—Phe—Ala—His—Leu—Asp—Ile—Ile—Trp—OH SEQ ID NO:43 |
| I-27 (27) | ⌐Gly—Asn—Trp—His—Gly—Thr—Ala—Pro—Asp—Trp—Ile—Ile—Trp—OH SEQ ID NO:44 |
| I-28 (28) | ⌐Gly—Asn—Trp—His—Gly—Thr—Ala—Pro—Asp—Trp—Leu—Tyr—Phe—Ala—His—Gln—Asp—Val—Ile—Trp—OH SEQ ID NO:45 |
| I-29 (29) | ⌐Gly—Asn—Trp—His—Gly—Thr—Ala—Pro—Asp—Ala—OCH₂C₆H₅ SEQ ID NO:46 |
| I-30 (30) | ⌐Gly—Asn—Trp—His—Gly—Thr—Ala—Pro—Asp—Val—OCH₂C₆H₅ SEQ ID NO:47 |
| I-31 (31) | ⌐Gly—Asn—Trp—His—Gly—Thr—Ala—Pro—Asp—Trp—Gly—OCH₃ SEQ ID NO:48 |

-continued

| Compound Example | Amino Acid Sequence |
|---|---|
| I-32 (32) | ⌐Gly—Asn—Trp—His—Gly—Thr—Ala—Pro—Asp—Trp—Asn—Tyr—<br>Tyr—Trp—OH SEQ ID NO:49 |
| I-33 (33) | ⌐Gly—Asn—Trp—His—Gly—Thr—Ala—Pro—Asp—Trp—Val—Tyr—<br>Phe—Ala—Phe—Phe—Asn—Tyr—Tyr—Trp—OH SEQ ID NO:50 |
| I-34 (34) | ⌐Gly—Asn—Trp—His—Gly—Thr—Ala—Pro—Asp—Trp—Val—Tyr—<br>Tyr—Ala—His—Leu—Asp—Ile—Ile—Trp—OH SEQ ID NO:51 |
| I-35 (35) | ⌐Gly—Asn—Trp—His—Gly—Thr—Ala—Pro—Asp—Trp—Ala—His—<br>Leu—Asp—Ile—Ile—Trp—OH SEQ ID NO:52 |
| I-36 (36) | ⌐Gly—Asn—Trp—His—Gly—Thr—Ala—Ala—Asp—Trp—Phe—Phe—<br>Asp—Tyr—Tyr—Trp—OH SEQ ID NO:53 |
| I-37 (37) Sequence 10 | H—Gly—Asn—Trp—His—Gly—Thr—<br>Ala—Pro—Asp—Trp—Val—Tyr—Tyr—<br>Ala—His—Leu—Asp—Ile—Ile—<br>Trp—OH SEQ ID NO:54 |
| I-38 (38) Sequence 11 | H—Gly—Asn—Trp—His—Gly—Thr—<br>Ala—Pro—Asp—Trp—Leu—Tyr—Phe—<br>Ala—His—Gln—Asp—Val—Ile—<br>Trp—OH SEQ ID NO:55 |
| I-39 (39) | ⌐Gly—Asn—Trp—His—Gly—Thr—Ala—Pro—Asp—Trp—Phe—Phe—<br>Asn—Tyr—Tyr—Asn—Ile—Ile—Trp—OH SEQ ID NO:56 |
| I-40 (40) | ⌐Gly—Asn—Trp—His—Gly—Thr—Ala—Pro—Asp—Trp—Phe—Phe—<br>Asn—Tyr—Tyr—Ala—His—Leu—Asp—Ile—Ile—Trp—OH SEQ ID NO:57 |
| I-41 (41) | ⌐Gly—Asn—Trp—His—Gly—Thr—Ala—Pro—Asp—Trp—Val—Tyr—<br>Phe—Ala—His—Leu—Asp—Ile—Ile—Trp—OH SEQ ID NO:58 |
| I-42 (42) | ⌐Gly—Asn—Trp—Lys—Gly—Thr—Ala—Pro—Asp—Trp—Val—Tyr—<br>Phe—Ala—His—Leu—Asp—Ile—Ile—Trp—OH SEQ ID NO:59 |
| I-43 (43) Sequence 12 | H—Gly—Asp—Trp—His—Gly—Thr—<br>Ala—Pro—Asp—Trp—Val—Tyr—<br>Phe—Ala—His—Leu—Asp—Ile—<br>Ile—Trp—OH SEQ ID NO:60 |
| I-44 (44) Sequence 13 | H—Gly—Asn—Trp—Lys—Gly—Thr—<br>Ala—Pro—Asp—Trp—Val—Tyr—<br>Phe—Ala—His—Leu—Asp—Ile—<br>Ile—Trp—OH SEQ ID NO:61 |
| (I-45) Ex. 45 | ⌐Gly—Asn—Trp—His—Gly—Thr—Ala—Pro—Asp—Trp—<br>Phe—Phe—Asn—Tyr—Tyr—Trn |
| (I-46) Ex. 46 | ⌐Gly—Asn—Trp—His—Gly—Thr—Ala—Pro—Asp—Trp—<br>Phe—Phe—Asn—Tyr—Tyr—Trp—OCH₃ SEQ ID NO:63 |
| (I-47) Ex. 47 | ⌐Gly—Asn—Trp—His—Gly—Thr—Ala—Pro—Asp—Trp—<br>Phe—Phe—Asn—Tyr—Tyr—Trp—OCH₂C₆H₅ SEQ ID NO:64 |

| Compound Example | Amino Acid Sequence |
|---|---|
| (I-48) Ex. 48 | Gly—Asn—Trp—His—Gly—Thr—Ala—Pro—Asp—Trp—Phe—Phe—Asn—Tyr—Tyr—Trp—NH₂ SEQ ID NO:65 |
| (I-49) Ex. 49 | Gly—Asn—Trp—His—Gly—Thr—Ala—Pro—Asp—Trp—Phe—Phe—Asn—Tyr—Tyr—Nal—OH SEQ ID NO:66 |

The pharmacological effects of representative compounds of Compound (I) are illustrated below, referring to Test Examples.

Test Example 1

Effect of Compound (I) on lowering intracellular calcium concentration increased by endothelin.

In this test, cell line A10 (ATCC CRL 1476) taken from an aortic unstriated muscle of a rat's breast was suspended in a Dulbecco's modified Eagle culture medium (product of Nissui Seiyaku Co.) containing 10% fetal calf serum (product of Hyclone Co.). The suspended cells were plated on a glass coverslip with a silicon rubber wall for 3 days. The cultured cells were washed with a physiological experimental solution A (pH 7.4) comprising 130 mM NaCl, 2.5 mM KCl, 1 mM CaCl₂, 1 mM MgSO₄, 1 mM NaH₂PO₄, 10 mM N-(2-hydroxyethyl)-piperazine-N'-2-ethanesulfonic acid (HEPES), 15 mM glucose and 2 mg/ml bovine serum albumin (BSA) (product of Sigma Co.). Then, 10 μM of fura-2/AM (calcium fluorescent indicator, product of Dojin Kagaku Laboratory) was added to the cells and the mixture was incubated for one hour.

After washing the culture with physiological experimental solution A, the glass covership with a silicon rubber wall was filled with 1 ml of physiological experimental solution A containing Compound (I-1) (final concentration: 1 μg/ml) or 1 ml of experimental solution A containing no Compound (I-1), and endothelin (final concentration: 0.3 nM) was added thereto. The intracellular calcium concentration of the individual cells and the change in the concentration was determined by measuring the fluorescence intensity at 510 nm, exposed to ultraviolet light at excitation wavelengths 340 nm and 380 nm, with an ARGUS200 system (product of Hamamatsu Photonics Co.).
Result:

By comparison of the increase in the intracellular calcium concentration due to the addition of endothelin (final concentration: 0.3 nM), between the control group (cell count: 201) where Compound (I-1) was not added, and the test group (final concentration: 1 μg/ml, cell count: 171) where Compound (I-1) was added, the increase ratio of the test group was 46% to the increase of the control group.

Test Example 2

Endothelin receptor-antagonizing activity

Bovine lung tissue was homogenized at 4° C. using POLYTRON (type PT10/35, manufactured by Kinematica GmbH Co.) in a buffer solution A (pH 8.3) comprising 1 mM NaHCO₃, 5 mM ethylenediaminetetraacetic acid, 5 μg/ml leupeptin, 5 μg/ml pepstatin A and 40 μM phenylmethylsulfonyl fluoride.

The thus obtained suspension was centrifuged for 10 minutes at 8,000 G and 4° C., and the resulting supernatant was centrifuged for 60 minutes at 40,000 G and 4° C., to obtain a pellet. The pellet was suspended in buffer solution A and again centrifuged for 60 minutes at 40,000 G and 4° C. The resulting solid substance was prepared as a suspension containing 2 mg/ml of a protein, and the suspension was used as the membrane fraction liquid. A membrane fraction solution was then prepared by adding 7 μl of the membrane fraction liquid per 1 ml of a buffer solution B (pH 7.6) comprising 50 mM Tris-HCl, 1 mM ethylenediaminetetraacetic acid and 0.2% bovine serum albumin.

$^{125}$I-Endothelin-1 (approx. 30,000 cpm) was added to the membrane fraction solutions containing unlabelled endotheline-1 (final concentration 100 nM), Compound (I-1) or Compound (I-2) or containing neither of them. These mixtures were allowed to stand at 25° C. for 2 hours, and then filtered with a GF/B glass filter (product of Whatman Co.). After washing the glass filter with a buffer solution C (pH 7.6) comprising 50 mM Tris-HCl and 1 mM ethylenediaminetetraacetic acid, the radioactivity on the glass filter was measured to determine the amount of the receptor and the non-specific bound $^{125}$I-endothelin. The inhibition rate against endothelin receptor binding activity was calculated according to the following equation.

$$\text{Inhibition rate}=(C-A/C-B)\times 100(\%)$$

A: Radioactivity in the presence of Compound (I-1) or Compound (I-2)

B: Radioactivity in the presence of unlabelled endothelin-1

C: Radioactivity in the absence of Compound (I-1), Compound (I-2) and unlabelled endothelin-1

Result:

The concentration (IC₅₀) of Compound (I-1) causing 50% inhibition of endothelin-1 binding was 25 nM, and the concentration of Compound (I-2) causing 50% inhibition of endothelin-1 binding (IC50) was 55 nM.

Test Example 3

Effect of Compound (I) on lowering intracellular guanosine-3',5'-cyclic-monophosphate concentration increased by endothelin Evaluation was made using the method of Ishii et al., described in the Journal of Pharmacology and Experimental Therapeutics, 259, 3, 1102–1108 (1991).

Endothelin-1 (final concentration 1 nM) was added to test solutions containing Compound (I-1) (final concentration: 3 μg/ml) or Compound (I-2) (final concentration: 3 μg/ml) or to a test solution containing neither of them. The intracellular guanosine-3',5'-cyclic monophosphate concentration was measured with a Cyclic GMP Assay Kit (manufactured by Yamasa Shoyu Co.) to determine the change in the concentration.

Result:

The amount of increase in intracellular guanosine-3',5'-cyclic monophosphate concentration due to 1 nM endothelin in the presence of 3 µg/ml of Compound (I-1) was 0% to that due to addition to only 1 nM endothelin. The amount of increase in intracellular guanosine-3',5'-cyclic monophosphate concentration due to 1 nM endothelin in the presence of 3 µg/ml of Compound (I-2) was 17% to that due to addition of only 1 nM endothelin. The increase in intracellular guanosine-3',5'-cyclic monophosphate concentration due to 1 nM endothelin was suppressed by the addition of 3 µg/ml Compound (I-1) and 3 µg/ml Compound (I-2).

Test Example 4

Endothelin receptor-antagonizing effect

The inhibition rate against endothelin receptor binding activity was calculated by the same method as in Test Example 2, except for using bovine cerebellar tissue instead of the bovine lung tissue used in Test Example 2, and except for using the test compounds listed in Table 2.

The results are shown in Table 2.

TABLE 2

| Compound No. | IC$_{50}$ [nM] | Compound No. | *IC$_{50}$ [nM] |
| --- | --- | --- | --- |
| I-1 | 10 | I-29 | >1,000 |
| I-2 | 30 | I-30 | >1,000 |
| I-3 | 5 | I-31 | >1,000 |
| I-4 | >5,000 | I-32 | >570 |
| I-5 | >5,000 | I-33 | >40 |
| I-6 | >5,000 | I-34 | 2.5 |
| I-7 | >5,000 | I-35 | >51 |
| I-8 | >5,000 | I-36 | >570 |
| I-14 | >1,000 | I-37 | 0.83 |
| I-15 | >900 | I-38 | 0.33 |
| I-16 | >1,000 | I-39 | >72 |
| I-17 | 54 | I-40 | >45 |
| I-18 | 36 | I-41 | 0.25 |
| I-19 | 370 | I-42 | 0.38 |
| I-20 | 300 | I-43 | 0.63 |
| I-21 | 470 | I-44 | 0.29 |
| I-22 | 12 | I-45 | 50 |
| I-23 | 45 | I-46 | 15 |
| I-24 | 810 | I-47 | 140 |
| I-25 | 0.24 | I-48 | 49 |
| I-26 | <0.13 | I-49 | 6.3 |
| I-27 | >6,000 | | |
| I-28 | 3.8 | | |

*Concentration causing 50% inhibition of endothelin-1 binding activity.

Test Example 5

Effect of Compound (I) against airway contraction due to endothelin

The in vivo effect of the compounds according to the present invention against airway contraction was evaluated according to a slightly modified version of the method of C. Touvay et al. described in European Journal of Pharmacology, 176, 23–33, 1990. That is, male Hartley guinea pigs weighing 350 to 550 grams each which had been previously β-blocked by intravenous injection of propranolol (3 mg/kg) were anesthetized, bronchial cannula were inserted therein and fixed, and connected to an artificial respirator. Next, spontaneous breathing was stopped with 10 mg/kg Gallamine triethiodide (product of Sigma Co. administered intravenously), after which artificial respiration was initiated at a determined rate. A respiration volume measuring device was connected to the bronchial cannula bypass, and the change in the air flow was measured as an indication of airway contraction. Endothelin-3 (1.5 µmol/l; product of Peptide Institute, Inc.) was intravenously injected at a dose of 0.1 ml per 100g body weight. Airway contraction (air flow increase) was observed immediately after injection, and was followed by a diphasic airway contraction reaction with an early and late phase which peaked at 30 seconds and 3 minutes, respectively. When a solution of Compound (I-1) (dimethylsulfoxide: physiological saline=1:1) was intravenously administered before injection of endothelin-3 in order to counter the airway contraction reaction, a more excellent contraction-inhibiting effect was observed in the endothelin-added group than in the control group.

Evaluation of the effect of Compound (I-1) against airway contraction was made twice, at 30 seconds (earlier phase) and 3 minutes (later phase) after injection of endothelin-3, and the rate or magnitude of inhibition was calculated according to the following equation.

Rate of inhibition (%)=(1−b/a)×100 a: Airway contraction without injection of Compound (I-1) (control)

b: Airway contraction with injection of Compound (I-1)

TABLE 3

| | Rate of inhibition (%) | |
| --- | --- | --- |
| Dose (mg/kg, i.v.) | Earlier phase 30 seconds | Later phase 3 minutes |
| Compound (I-1) | | |
| 0.1 | 12.5 | 44.0 |
| 0.3 | 46.0 | 52.7 |
| 1.0 | 91.8 | 78.2 |

The results show that Compound (I-1) has an antagonizing effect against endothelin-3 and an inhibiting effect on airway contraction, in a living body as well.

Test Example 6

Acute toxicity

Compound (I-1) was intraperitoneally administered to a group consisting of 3 ddy strain mice weighing 20±1 g. The mortality was observed seven days after the administration, and the minimum lethal dose (MLD) was determined to be 300 mg/kg or higher.

Test Example 7

Endothelin receptor-antagonizing activity

The inhibition rate against endothelin receptor binding activity was calculated by the same method as in Test Example 2, except for adding 1.5 µg/ml Compound (I-1) to the membrane fraction solution.

The results are shown in Table 3.

TABLE 3

| Compound No. | *IC$_{50}$ (nM) |
| --- | --- |
| I-1 | >1000 |
| I-45 | 300 |
| I-46 | 58 |
| I-47 | >470 |
| I-48 | >490 |
| I-49 | >440 |

*Concentration causing 50% inhibition of endothelin-1 binding activity.

BEST MODE FOR CARRYING OUT THE INVENTION

The abbreviations for the amino acids and their protective groups used in the following examples follow the recommendations of the IUPAC-IUB Commission on Biochemical Nomenclature relating to biochemical nomenclature (Biochemistry, 11, 1726, 1972). The amino acids and protective groups are defined as follows.

Gly: Glycine
Val: L-valine
Ile: L-isoleucine
Leu: L-leucine
Glx: L-glutamic acid or L-glutamine
Gln: L-glutamine
Ser: L-serine
Thr: L-threonine
Asp: L-aspartic acid
Asn: L-asparagine
Lys: L-lysine
Tyr: L-tyrosine
Cys: L-cysteine
Phe: L-phenylalanine
Trp: L-tryptophan
His: L-histidine
Pro: L-proline
Asx: L-aspartic acid or L-asparagine
Nal: L-$\beta$-(2-naphthyl)alanine
t-Boc: t-butyloxycarbonyl
Me: methyl
Bzl: benzyl
Bzl(NO$_2$): 4-nitrobenzyl
Cl-Z: 2-chlorobenzyloxycarbonyl
Br-Z: 2-bromobenzyloxycarbonyl
4-CH$_3$Bzl: 4-methylbenzyl
t-Bu: tert-butyl
Bom: benzyloxymethyl
Trt: trityl
Fmoc: 9-fluorenylmethyloxycarbonyl
Z: benzyloxycarbonyl
CHO: formyl
Ac: acetyl
CHPh$_2$: benzhydryl
Trn: 2-(3-indolyl)ethylamine The side-chain protected amino acids are defined as follows.

Trp(CHO): N$^{in}$-formyl-L-tryptophan
t-Boc-Tyr(Br-Z): N$^\alpha$-t-butyloxycarbonyl-O-2-bromobenzyloxycarbonyl-L-tyrosine
t-Boc-His (Bom): N$^\alpha$-t-butyloxycarbonyl-N$^{im}$-benzyloxycarbonyl-L-histidine
Asp(Ot-Bu): $\beta$-t-butyl aspartate
t-Boc-Thr(Bzl): N$^\alpha$-t-butyloxycarbonyl-O-benzyl-L-threonine
t-Boc-Asp(OBzl): $\beta$-benzyl N$^\alpha$-t-butyloxycarbonyl-L-aspartate
t-Boc-Cys(4-CH$_3$Bzl): N$^\alpha$-t-butyloxycarbonyl-S-4-methylbenzyl-L-cysteine
Fmoc-Asp(Ot-Bu)-OH: $\beta$-t-butyl N$^\alpha$-9-fluorenylmethyloxycarbonyl-L-aspartate
Fmoc-Tyr(t-Bu)-OH: N$^\alpha$-9-fluorenylmethyloxycarbonyl-O-t-butyl-L-tyrosine
Fmoc-Asn(Trt)-OH: N$^\alpha$-9-fluorenylmethyloxycarbonyl-N$\gamma$-trityl-L-asparagine
Fmoc-His(Trt)-OH: N$^\alpha$-9-fluorenylmethyloxycarbonyl-N$^{im}$-trityl-L-histidine
Fmoc-Thr(t-Bu)-OH: N$^\alpha$-9-fluorenylmethyloxycarbonyl-O-t-butyl-L-threonine
Fmoc-Gln(Trt)-OH: N$^\alpha$-9-fluorenylmethyloxycarbonyl-N$^\delta$-trityl-L-glutamine
Fmoc-Lys(Z)-OH: N$^\alpha$-9-fluorenylmethyloxycarbonyl-N$^\epsilon$-carbobenzoxy-L-lysine
Fmoc-Lys(t-Boc)-OH: N$^\alpha$-9-fluorenylmethyloxycarbonyl-N$^\epsilon$-t-butyloxycarbonyl-L-lysine
H-Trp-OMe: L-tryptophan methyl ester
H-Trp-OB$_z$l: L-tryptophan benzyl ester
H-Nal-OBzl(NO$_2$): L-$\beta$-(2-naphthyl)alanine 4-nitrobenzyl ester The abbreviations for the reactive solvents and reagents are defined as follows.
DCC: dicyclohexylcarbodiimide
DEPC: diethylphosphorocyanidate
HONSu: N-hydroxysuccinimide
PyBOP: benzotriazole-1-yl-oxy-tris(pyrrolidino) phosphonium hexafluorophosphate
HOB t: N-hydroxybenzotriazole
NMM: N-methylmorpholine
DMF: N,N-dimethylformamide
TFA: trifluoroacetic acid
TosOH: p-toluenesulfonic acid
Pd/C: Palladium-carbon catalyst
TEA: triethylamine In the following Examples 1, 3 and 6–10 and Reference Examples 1 and 2, a 430A peptide synthesizer, manufactured by ABI Co., was used to synthesize the peptides using reagents and solvents of ABI Co., operating the synthesizer according to the synthesis program of ABI Co. The condensation reaction of the amino acids was effected with a symmetrical acid anhydride under standard conditions.

Also, in the following Examples 16, 17 and 21–40 and Reference Examples 3 and 4, a PSSM8 peptide synthesizer, manufactured by Shimadzu Seisakusho, was used to synthesize the peptides using reagents and solvents of Shimadzu Seisakusho, operating the synthesizer according to the synthesis program of Shimadzu Seisakusho. The condensation reaction of the amino acids was effected under standard conditions following the Fmoc method ("Fundamentals and Experiments in Peptide Synthesis", Izumiya, N. et al., Maruzen).

BEST MODE FOR CARRYING OUT THE INVENTION

Example 1

Streptomyces sp. RE-701 was used as a seed strain. One loopful of the seed strain was inoculated in 10 ml of a seed medium (pH 7.2) comprising 10 g/l glucose, 3 g/l beef extract (product of Kyokutoh Seiyaku), 5 g/l powdered yeast extract S (product of Nihon Seiyaku), 5 g/l Bacto-Tryptone (product of Difco Co., Ltd.), 1 g/l monopotassium phosphate, 0.5 g/l magnesium phosphate 7 hydrate and 2 g/l calcium carbonate, charged in a 50 ml-large test tube, and cultured with shaking at 28° C. for 5 days.

Nine milliliters of the seed culture medium was transferred to 300 ml of a second medium charged in a 2-liter Erlenmeyer flask provided with baffles. The second culture medium has the same composition as the seed medium. The second culture was carried out at 28° C. for 2 days, and 300 ml of the second culture was transferred to 9.7 liters of a third medium in a 30 liter-stainless steel jar fermenter. The third medium has the same composition as the seed medium. The third culture was carried out at 28° C. for 3 days with the aeration and stirring (250 rpm, aeration: 10 liter/min). Ten liters of the third culture was transferred to 90 liters of a fermentation medium (pH 7.0) comprising 40 g/l glucose, 40 g/l soluble starch, 10 g/l soybean powder, 5 g/l corn steep liquor, 5 g/l dried yeast, 0.5 g/l potassium phosphate, 1 μg/l cobalt chloride, 1 μg/l nickel sulfate, 10 μg/l zinc sulfate and 0.5 g/l magnesium phosphate, charged in a 200-liter stainless steel jar fermenter. Culturing was carried out at 28° C. for 4 days with the aeration and stirring (200 rpm, aeration: 100 l/min).

One hundred liters of the culture obtained was continuously centrifuged to collect the cells, and 70 liters of acetone was added to the cells. The mixture was agitated and filtered. The filtrate thus obtained was concentrated under reduced pressure to remove the acetone, and the residue was passed through a DIAION HP-20 column DIAION (5 l) for adsorption. Then, 25 liters of 50% methanol was passed through the column, and the elution was carried out with methanol. The fractions containing Compound (I-1) were collected and diluted with water. The aqueous solution was passed through a DIAION HP-20SS column (2.5 l) filled with 50% methanol, for adsorption. The column was washed with 7.5 liters of 70% methanol, and the elution was carried out with 80% methanol. The fractions containing Compound (I-1) were collected and concentrated to dryness under reduced pressure, and thus 2.2g of a light-brown solid was obtained. The obtained solid was dissolved in methanol, and the solution was passed through an LH-20 column (2 l) filled with methanol. The elution was carried out with methanol. The fractions containing Compound (I-1) were collected and concentrated to dryness under reduced pressure, and 350 mg of a white solid was obtained. The resulting solid was dissolved in methanol, and isolated and purified using a preparative HPLC (LC-8 system, manufactured by Shimadzu Seisakusho) under the conditions listed below. The trifluoroacetic acid in the fractions containing Compound (I-1) was removed with a Sep-Pak C-18 (manufactured by Waters Co.) and the residue was concentrated to dryness under reduced pressure to obtain 20 mg of dry powder of Compound (I-1).

Separatory HPLC conditions:

Column: SH-363-10 (C-18 reverse phase silica gel, YMC Co.)

Eluent: 0.1% TFA solution-acetonitrile (30%–65%) linear concentration gradient.

Elution time: 20 min.

Flow rate: 25 ml/min.

The physiological properties of Compound (I-1) are described below. The properties were determined using the instruments listed below. MS spectrum: Nihon Denshi JMS-SX102A (measured according to FAB)

Amino acid analysis was made according to the method of Bidlingmeyer, B. A. et al. (J. Chromatogr., 336, 93, 1984). Hydrolysis was conducted in hydrochloric acid vapor at 110° C. for 22 hours, and the amino acid composition of the hydrolyzates was analyzed with a Waters Pico Tag amino acid analyzer. Further, only tryptophan was hydrolyzed by the method of Matsubara, et al. (Biochem. Biophys. Res. Commun., 35,175, 1969), and analyzed with a JLC-300 amino acid analyzer (manufactured by Nihon Denshi). The found values were expressed with the value for Ala defined as 1.00.

MS analysis: Found: 2042.8722 Calculated for $^{12}C_{103}H_{115}N_{23}O_{23}+H$: 2042.8614

Amino acid analysis: Found (theoretical): Asx 2.54(3), Gly 2.13(2), His 0.93(1), Thr 1.00(1), Ala 1.00(1), Pro 1.15(1), Tyr 1.95 (2), Phe 2.06(2), Trp 2.54(3)

After hydrolysis, derivation of the amino acid was made with (+)-1-(9-fluorenyl) ethylchloroformate and analysis using reverse phase HPLC showed that all the amino acid configurations were L-form.

The primary structure of the amino acids was determined by partial hydrolysis with 0.05N hydrochloric acid at 108° C. for 2 hours, isolation by HPLC, and automatic Edman degradation of the resulting partially hydrolyzed peptides (470A protein sequencer, 120A on-line PTH amino acid analyzer, manufactured by ABI Co.) and FAB-MS spectrum analysis. Also, tryptophan at the C-terminal was identified by the hydrazinolysis method [Akabori, et al., Bull, Chem. Soc. Jap., 25, 214 (1967)].

The Rf values for RES-701-1 were determined by development by thin-layer chromatography using various solvents. Detection was made by iodine reaction, sulfate coloration or ultraviolet irradiation at 253.7 nm. Developing conditions 1:

Thin Layer: Kiselgel 60F$_{254}$ (manufactured by Merck Co., Art. 5629)

Developing solvent: chloroform:methanol:ethanol:water= 10:4:4:2

Developing method: room temperature, upward, 15–60 min.

Rf value: 0.4

Developing conditions 2:

Thin-layer and developing method are the same as described in development conditions 1.

Developing solvent: 100% methanol

Rf value: 0.6

Developing conditions 3: Developing method is the same as described in development conditions 1.

Thin-layer: RP-18 (manufactured by Merck Co., Art. 13724)

Development solvent: 80% methanol

Rf value: 0.3

Developing conditions 4: Developing method is the same as described in development conditions 1.

Thin-layer: RP-18 (manufactured by Merck Co., Art. 13724)

Developing solvent: 90% acetonitrile

Rf value: 0.4

EXAMPLE 2

Compound (I-2)

Streptomyces sp. RE-701 was used as a seed strain.

One loopful of the seed strain were inoculated in each of four 250 ml Erlenmeyer flasks containing 40 ml of a first seed medium (pH 7.2) comprising 10 g/l glucose, 10 g/l soluble starch, 3 g/l beef extract (product of Kyokutoh Seiyaku), 5 g/l powdered yeast extract S (product of Nihon Seiyaku), 5 g/l Bacto-Tryptone (product of Difco Co., Ltd.), 1 g/l monopotassium phosphate, 0.5 g/l magnesium sulfate heptahydrate, 2 g/l calcium carbonate and 0.5 g/l LG-109 (product of Shinetsu Kagaku Co.), and cultured with shaking at 28° C. for 3 days.

Ten milliliters of the first seed culture obtained was transferred to each of six 2 l Erlenmeyer flasks provided with baffles, containing 300 ml of a second seed culture medium. The second seed culture medium had the same composition as the first seed culture medium. The second seed culturing was carried out at 28° C. for 2 days, and 1800 ml of the second culture was transferred to 100 liters of a third seed medium in a 200 l stainless steel jar fermenter. The third medium had the same composition as the first seed culture medium. The third culturing was carried out at 28° C. for 27 hours with aeration and stirring (220 rpm, aeration: 60 liter/min). One hundred liters of the third culture obtained was transferred to 1,000 liters of a main fermentation medium charged in a 2,000 l stainless steel jar fermenter. The main fermentation medium used (pH 7.0) comprised 50 g/l soluble starch, 30 g/l dried yeast, 0.5 g/l monopotassium phosphate, 0.5 g/l magnesium phosphate and 0.5 g/l LG-109 (product of Shinetsu Kagaku Co.). The main fermentation culturing was carried out at 28° C. for 3 days with aeration and stirring (140 rpm, aeration: 400 l/min).

Upon addition of 400 l of n-propyl alcohol and a filtration aid to 1,000 l of the obtained culture, the mixture was thoroughly stirred and filtered with a filter press. Water was then added to the filtrate until the concentration of n-propyl alcohol was 20%, and the mixture was passed through a 50 liter column filled with DIAION HP-20 (product of Mitsubishi Kasei Corporation). The RES-701-2 was adsorbed, washed with 200 l of 60% methanol, and eluted with 250 l of 80% methanol. To 150 ml of the fractions containing RES-701-2 were added water and ammonium acetate, the pH was adjusted to 7.0 with 30% methanol containing 50 mM ammonium acetate, and the mixture was passed through a 15 l Sepabead FP-DA13 column (product of Mitsubishi Kasei Corporation) filled with 30% methanol and 30% methanol (pH 7.0) containing 50.mM ammonium acetate, washed with 15 l of 30% methanol (pH 7.0) containing 50 mM ammonium acetate and 45 liters of 30% methanol (pH 7.0) containing 1M ammonium acetate, and eluted with 60 liters of 50% methanol containing 0.6M acetic acid. Fractions containing Compound (I-2) were collected, passed through an HP-20SS column (10 liters) filled with 60% methanol, washed first with 50% methanol and then with 70% methanol, and eluted with 75% methanol. Fractions containing RES-701-2 were collected and dried under reduced pressure to obtain a light-brown solid. The solid was then dissolved in 25% acetonitrile, and isolated again by preparative HPLC (product of Soken Kagaku Co.) under the conditions described below.

Carrier: ODS AQ S-50 (product of YMC Co.)

Eluent: acetonitrile (25%–50%) linear concentration gradient.

Elution time: 250 min.

Amount of sample: 500 mg/elution

Flow rate: 250 ml/min.

The fractions having a retention time of 3.5–4.5 hours were taken and dried under reduced pressure to obtain 800 mg of a dry powder containing RES-701-2.

The physiological properties of RES-701-2 are described below. The properties were determined using the instruments listed below. MS spectrum: Nihon Denshi JMS-HX110A (measured according to FAB)

Amino acid analysis was made according to the method of Bidlingmeyer, B. A. et al. (J. Chromatogr., 336, 93, 1984). Hydrolysis was conducted in hydrochloric acid vapor at 110° C. for 22 hours, and the amino acid composition of the hydrolyzates was analyzed with a Waters Pico Tag amino acid analyzer. Further, only tryptophan was hydrolyzed by the method of R. J. Simpson, et al. [J. Biol., Chem., 251, 1936, (1976)], and analyzed with the above mentioned amino acid analyzer. The found values were expressed with the value for Ala defined as 1.00.

MS analysis: Found: 2058.8496

Amino acid analysis: Found (theoretical): Asx 2.61 (3), Gly 2.25(2), His 0.92(1), Thr 1.02(1), Ala 1.00(1), Pro 1.14(1), Tyr 1.74(2), Phe 1.90(2), Trp 2.15(2)

After hydrolysis, derivation of the amino acid with (+)-1-(9-fluorenyl) ethylchloroformate and analysis by reverse phase HPLC showed that all the amino acid configurations were L-form.

The primary structure of the amino acids other than the C-terminal amino acid was determined by partial hydrolysis in 0.1N hydrochloric acid at 108° C. for 2 hours, isolation by reverse phase HPLC, and analysis of the partially hydrolyzed peptides by use of automatic Edman degradation (470A protein sequencer, 120A on-line PTH amino acid analyzer, manufactured by ABI Co.) and FAB-MS spectrum.

The C-terminal amino acid was identified to be 7-hydroxytryptophan by the hydrazinolysis method (Akabori, et al., Bull. Chem. Soc. Jap., 25, 214, 1964), digestion with carboxypeptidase A (product of Sigma Co.), isolation of the C-terminal amino acid by reverse phase HPLC, and the above mentioned FAB-MS spectrum analysis and NMR spectrum analysis (product of Bruker Co., AM500, $^1$H-500 MHz). A polarimeter (Jasco DIP-370) clearly showed the amino acid configuration to be L-form.

EXAMPLE 3

Compound (I-3)

Streptomyces sp. RE-629 was used as a seed strain.

One loopful of the seed strain were inoculated in each of four 250 ml Erlenmeyer flasks containing 40 ml of a first seed culture medium (pH 7.2) comprising 10 g/l glucose, 10 g/l soluble starch, 3 g/l beef extract (product of Kyokutoh Seiyaku), 5 g/l powdered yeast extract S (product of Nihon Seiyaku), 5 g/l Bacto-Tryptone (product of Difco Co., Ltd.), 1 g/l monopotassium phosphate, 0.5 g/l magnesium sulfate heptahydrate, 2 g/l calcium carbonate and 0.5 g/l LG-109 (product of Shinetsu Kagaku Co.), and cultured with shaking at 28° C. for 3 days. Ten milliliters of the first seed culture obtained was transferred to each of six 2 l Erlenmeyer flasks provided with baffles, which contained 300 ml of a second seed medium. The second seed medium had the same composition as the first seed medium. The second seed culturing was carried out at 28° C. for 2 days, and 1800 ml of the second culture obtained was transferred to 100 liters of a main fermentation culture medium in a 200-liter stainless steel jar fermenter. The main fermentation medium used (pH 7.0) comprised 50 g/l soluble starch, 30 g/l dried yeast, 0.5 g/l monopotassium phosphate, 0.5 g/l magnesium phosphate and 0.5 g/l LG-109 (product of Shinetsu Kagaku Co.). The main fermentation culturing was carried out at 28° C. for 3 days with aeration and stirring (140 rpm, aeration: 400 l/min). Upon addition of 40 liters of n-propyl alcohol and a filtration aid to 100 liters of the obtained culture solution, the mixture was thoroughly stirred and filtered with a filter press. Water was then added to the filtrate until the concentration of n-propyl alcohol was 20%, and the mixture was passed through a 5 liter column filled with DIAION HP-20 (product of Mitsubishi Kasei Corporation). The Compound (I-3) was adsorbed, washed with 20 l of 60% methanol, and eluted with 25 l of 80% methanol. To 15 ml of the fractions containing Compound (I-3) were added water and ammonium acetate, the pH was adjusted to 7.0 with 30% methanol containing 50 mM ammonium acetate, and the mixture was passed through a 1.5 l Sepabead FP-DA13 column (product of Mitsubishi Kasei Corporation) filled with 30% methanol (pH 7.0) containing 50 mM of ammonium acetate, washed with 1.5 l of 30% methanol (pH 7.0) containing 50 mM ammonium acetate, 4.5 liters of 30% methanol (pH 7.0) containing 1M ammonium acetate, and eluted with 6 liters of 50% methanol containing 0.6M of acetic acid. Fractions containing Compound (I-3) were collected, passed through an HP-20SS column (1 l) filled with 50% methanol, washed first with 50% methanol and then with 70% methanol, and eluted with 75% methanol. The fractions containing Compound (I-3) were collected and dried under reduced pressure to obtain a brown solid. The solid was then dissolved in 25% acetonitrile, and repeatedly isolated by preparative HPLC (product of Shimadzu Seisakujo Co.) under the conditions described below.

Column: ODS (diameter: 5 cm, length: 50 cm) (product of YMC Co.)
Eluent: acetonitrile (25%–50%) linear concentration gradient.
Elution time: 250 min.
Amount of sample: 10 mg/elution
Flow rate: 30 ml/min.

Fractions having the retention times of 180 to 210 minutes were isolated repeatedly, and then dried under reduced pressure to obtain 7 mg of dry powder containing Compound (I-3).

The physiological properties of Compound (I-3) are described below. The properties were determined using the instruments listed below. MS spectrum: Nihon Denshi JMS-HX110A Amino acid analysis was carried out in the same manner as in Example 2. The found values were expressed with the value for Phe defined as 2.00.

a) MS analysis Found: 2059.4626
a) Amino acid analysis: Found (theoretical): Asx 3.16(3), Ser 0.90(1), Gly 1.97(2), His 0.96(1), Thr 0.89(1), Pro 1.12(1), Tyr 1.92(2), Phe 2.00(2), Trp 2.91(3)

After hydrolysis, derivation of the amino acid with (+)-1-(9-fluorenyl) ethylchloroformate and analysis by reverse phase HPLC showed that all the amino acid configurations were L-form.

The primary structure was determined by partial hydrolysis in 0.1N hydrochloric acid at 108° C. for 2 hours, isolation by reverse phase HPLC, and analysis of the partially hydrolyzed peptides by use of automatic Edman degradation (470A protein sequencer, 120A on-line PTH amino acid analyzer, manufactured by ABI Co.) and FAB-MS spectrum analysis (JMS-HX110A, product of Nihon Denshi Co.).

The C-terminal amino acid was identified by the hydrazinolysis method (Akabori, et al., Bull. Chem. Soc. Jap., 25, 214, 1964), to be tryptophan.

EXAMPLE 4

Synthesis of Compound (I-4 ):

H-Gly-Asn-Trp-His-Gly-Thr-Ala-Pro-Asp-Trp-Phe-Phe-Asn-Tyr-Tyr-Trp-OH          SEQ ID NO:21

Following the synthesis program of ABI Co., 0.73 g of a carrier resin combined with 0.5 mmol of t-Boc-Trp (CHO) was placed in the reactor of an automatic synthesizer, and the following procedure was effected.

(a) A methylene chloride solution containing 33% TFA was added thereto and the mixture was stirred for 1 minute, 20 seconds, and the solution was drawn off.

(b) A methylene chloride solution containing 50% TFA was added thereto and the mixture was stirred for 18 minutes, 30 seconds and the solution was drawn off.

(c) The carrier resin was washed 3 times with methylene chloride.

(d) A methylene chloride solution containing 10% diisopropylethylamine was added thereto and the mixture was stirred for 1 minute, the solution was drawn off, and this procedure was repeated again.

(e) The carrier resin was washed 5 times with DMF. Thus, a Trp(CHO)-bound carrier resin was obtained.

(f) To the carrier resin was added 4 ml of a DMF solution containing 2.0 mmol of a symmetric acid anhydride of t-Boc-Tyr(Br-Z), the mixture was stirred for 18 minutes, and the solution was drawn off.

(g) The carrier resin was washed 5 times with methylene chloride.

In this manner, t-Boc-Tyr(Br-Z)-Trp(CHO) was synthesized on the carrier. Next, after the deprotective steps (a)–(e) above, the symmetric anhydride of t-Boc-tyr(Br-Z)-OH was added for a condensation reaction in step (f), after which t-Boc-Tyr(Br-Z)-Tyr(Br-Z)-Trp(CHO) was synthesized on the carrier resin in the washing step (g). In step (f), t-Boc-Asn-OH, t-Boc-Phe-OH, t-Boc-Phe-OH, t-Boc-Trp (CHO)-OH, t-Boc-Asp (OBzl)-OH, t-Boc-Pro-OH, t-Boc-Ala-OH, t-Boc-Thr (Bzl)-OH, t-Boc-Gly-OH, t-Boc-His (Bom)-OH, t-Boc-Trp (CHO)-OH, t-Boc-Asn-OH and t-Boc-Gly-OH were used in order, and steps (a)–(g) were repeated to obtain 2.0g of a side chain-protected peptide-bound carrier resin.

To 0.8 g of the obtained carrier resin were added 0.8 ml of 1,2-ethanedithiol, 0.8 ml of dimethylsulfide and 0.2 ml of anisol, and the mixture was allowed to stand for 3 hours, after which 18 ml of hydrogen fluoride was added thereto and the mixture was stirred on ice for 70 minutes. Next, the hydrogen fluoride was removed off under reduced pressure, 100 ml of ethyl acetate was added to the. carrier resin, and the mixture was stirred for half an hour. To the carrier resin obtained by filtration was added 100 me of DMF and the mixture was stirred for one hour. The carrier resin was then subjected to a fully automatic high speed cooling centrifuge (RE-20 model, Tomy Seiko), and centrifugation was carried out at 10,000 rpm for 10 minutes to obtain a supernatant. The DMF in this supernatant was removed using a concentrator (Rotary Vacuum Evaporator N-2 model, Tokyo Rika Kiki), and was redissolved in 2M acetic acid to obtain a crude product. This crude product was purified by HPLC using a reverse phase column (Capcell Pack C18 SG-120, 30×250 mm, manufactured by Shiseido). The elution was carried out with a linear concentration gradient pattern using 0–90% acetonitrile containing 0.1% TFA, and upon detection at 220 nm, fractions containing Compound (I-4) were obtained. These fractions were lyophilized to obtain 18.2 mg of Compound (I-4).

The MS analysis of Compound (I-4) was conducted using a Nihon Denshi JMS-HX110A, and amino acid analysis was carried out in the same manner as in Example 2.

In the following examples as well, MS analyses and amino acid analyses were effected in the same manner as in Example 4.

MS analysis [FABMS]: 2062 (M+H)

Amino acid analysis: Asx 2.5 (3), Gly2.2 (2), His 1.1 (1), Thr 1.1 (1) Ala 1.1 (1), Pro 1.1 (1), Tyr 2.1 (2), Phe 1.9 (2), (no analysis of Trp).

EXAMPLE 5

Synthesis Compound (I-1 ):

```
 ┌─────────────────────────────────────────────────┐
 └─ Gly—Asn—Trp—His—Gly—Thr—Ala—Pro—Asp—Trp—
```

Phe—Phe—Asn—Tyr—Tyr—Trp—OH SEQ ID NO:18

Synthesis of Compound (I-5):

cyclo(Gly-Asn-Trp-His-Gly-Thr-Ala-Pro-Asp-Trp-Phe-Phe-Asn-Tyr-Tyr-Trp)          SEQ ID NO:22

1.84 mg of the TFA salt of Compound (I-4) synthesized according to Example 4, was dissolved in 0.35 mg of methanol, after which 1.7 μl of a 5% HCl-methanol solution was added thereto and the mixture was allowed to stand at room temperature for 1 hour. A gel filtration column [Sephadex G-15 (manufactured by Pharmacia Co.), 44×9 mm I.D.] was then used for elution with methanol, to obtain fractions containing Compound (I-4). Next, the solvent was evaporated under reduced pressure to obtain 1.25 mg of a hydrochloride of Compound (I-4). 0.2 mg of the hydrochloride of Compound (I-4), was dissolved in 0.3 ml of dry DMF, and 0.1 ml each of 0.4 mg/ml HOBt and 0.61 mg/ml DCC prepared with dry DMF was added with cooling on ice. The reaction solution was allowed to stand on ice for 2 hours, and the temperature of the reaction solution was brought back to room temperature. The reaction solution was allowed to stand overnight. The insoluble matters were removed by centrifugation (15,000 rpm ×5 min., 0° C.), and the resulting supernatant was purified by reverse phase HPLC. The reverse phase column used was a YMC Pack ODS-AM312 (150×6 mm I.D.) manufactured by YMC Co. The elution was carried out with a linear concentration gradient pattern using 0–90% acetonitrile containing 0.1% TFA, with detection at 220 nm, to obtain a fraction containing both 5% Compound (I-1) and 95% Compound (I-5). The solvent of the fraction was then evaporated under reduced pressure to obtain a 0.01 mg of residue. The residue was dissolved in 50 μl of ethanol and purified by reverse phase HPLC using an ion pairing agent. The reverse phase column used was a YMC Pack ODS-AM312 (150×6 mm I.D.) manufactured by YMC Co., and the elution was carried out with an aqueous solution (pH=3.3) of 1 mM tetraethylammonium hydroxide and 0.1M monosodium phosphate containing 36% acetonitrile. The solvent of the fractions containing Compound (I-1) was evaporated under reduced pressure, and again purified by reverse phase HPLC with a linear concentration gradient pattern using 0–90% acetonitrile containing 0.1% TFA, and the solvent was evaporated under reduced pressure to obtain 0.5 μg of Compound (I-1).

The same procedure was followed to obtain 25 μg of Compound (I-5).

Compound (I-1)

MS analysis [FABMS]: 2044 (M+H)

Amino acid analysis: Asx 2.5 (3), Gly 2.2 (2), His 1.1 (1), Thr 1.1 (1), Ala 1.1 (1), Pro 1.1 (1), Tyr 2.1 (2), Phe 1.9 (2), (no analysis of Trp).

Compound (I-5)

MS analysis [FABMS]: 2044 (M+H)

Amino acid analysis: Asx 2.5 (3), Gly 2.2 (2), His 1.1 (1), Thr 1.1 (1), Ala 1.1 (1), Pro 1.1 (1), Tyr 2.1 (2), Phe 1.9 (2), (no analysis of Trp)

EXAMPLE 6

Synthesis of Compound (I-6 ):

H-Cys-Asn-Trp-His-Gly-Thr-Ala-Pro-Cys-Trp-Phe-Phe-Asn-Tyr-

Tyr-Trp-OH SEQ ID NO:23

A t-Boc-Trp(CHO)-combined carrier resin and N-protected amino acids, t-Boc-Tyr (Br-Z)-OH, t-Boc-Tyr (Br-Z)-OH, t-Boc-Asn-OH, t-Boc-Phe-OH, t-Boc-Phe-OH, t-Boc-Trp (CHO) -OH, t-Boc-Cys (4-CH₃Bzl)-OH, t-Boc-Pro-OH, t-Boc-Ala-OH, t-Boc-Thr (Bzl)-OH, t-Boc-Gly-OH, t-Boc-His (Bom)-OH, t-Boc-Trp (CHO)-OH, t-Boc-Asn-OH and t-Boc-Cys (4-CH₃Bzl)-OH were used in order, to obtain 2.0 g of the carrier resin combined with the side chain protected peptides, in the same manner as in Example 4. 0.8 g of the obtained carrier resin was treated in the same manner as in Example 4, with hydrogen fluoride followed by purification by HPLC, to obtain 298.4 mg of Compound (I-6).

MS analysis [FABMS]: 2096 (M+H)

Amino acid analysis: Asx 1.7 (2), Gly 1.0 (1), His 1.0 (1), Thr 1.0 (1), Ala 1.0 (1), Pro 1.0 (1), Tyr 2.0 (2), Phe 2.0 (2), Cys 1.9 (2) (no analysis of Trp).

EXAMPLE 7

Synthesis of Compound (I-7):

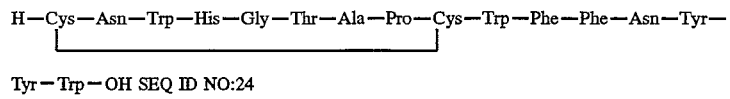

Tyr—Trp—OH SEQ ID NO:24

3 mg of Compound (I-6) obtained in Example 6 was dissolved in 10 ml of anhydrous methanol, and 0.2 ml of a 50 mM Tris-HCl buffer solution (pH 7.5) was added thereto with cooling on ice. Next, 1 ml of a hydrous methanol solution [MeOH: H₂O (V/V)=5:1] containing 1.6 mM oxidized glutathione was added to the solution. The mixture was stirred at room temperature for 16 hours. The reaction solution was then adjusted to pH 4 with hydrochloric acid and purified by reverse phase HPLC according to the same method as in Example 5, to obtain 1.5 mg of Compound (I-7).

MS analysis [FABMS]: 2094 (M+H)

Amino acid analysis: Asx 1.8 (2), Gly 1.0 (1), His 1.0 (1), Thr 0.9 (1), Ala 1.0 (1), Pro 1.0 (1), Tyr 2.0 (2), Phe 1.9 (2), (No analysis of Cys and Trp).

EXAMPLE 8

Synthesis of Compound (I-8):

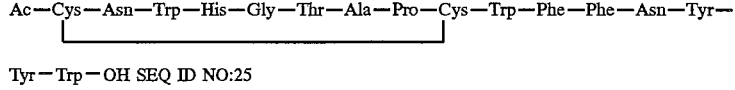

Tyr—Trp—OH SEQ ID NO:25

0.2 mg of Compound (I-7) was dissolved in 0.2 ml of DMF, and 100 μl of a 20 mM sodium phosphate buffer solution (pH 7.2) containing 40 μM EDTA was added to the solution. 50 μg of N-acetylsuccinimide was added thereto with cooling on ice, and the solution was stirred at 10° C. for 16 hours. The resulting reaction solution was adjusted to pH 4 with hydrochloric acid, and purified by reverse phase HPLC according to the same method as in Example 5, to obtain 110 μg of Compound (I-8).

29

MS analysis [FAMBS]: 2136 (M+H)

Amino acid analysis: Asx 1.8 (2), Gly 1.0 (1), His 1.0 (1), Thr 0.9 (1), Ala 1.0 (1), Pro 1.0 (1), Tyr 2.0 (2), Phe 1.9 (2) (no analysis of Cys and Trp).

EXAMPLE 9

Synthesis of Compound (II-9):

H-Trp-Phe-Phe-Asn-Tyr-Tyr-Trp-OH    SEQ ID NO:26

A t-Boc-Trp(CHO)-combined carrier resin and N-protected amino acids, t-Boc-Tyr (Br-Z)-OH, t-Boc-Tyr (Br-Z)-OH, t-Boc-Asn-OH, t-Boc-Phe-OH, t-Boc-Phe-OH, and t-Boc-TrP (CHO)-OH were used in order, to obtain 1.35 g of the carrier resin combined with the side chain-protected peptides, in the same manner as in Example 4. Using 0.8 g of the obtained carrier resin, free peptides were cleaved from the resin by treatment with hydrogen fluoride in the same manner as in Example 4, and then dissolved in 2M acetic acid and lyophilized to obtain 46.2 mg of a crude product. 4.0 mg of the crude product was purified by HPLC in the same manner as in Example 4, to obtain 2.4 mg of Compound (II-9).

MS analysis [FABMS]: 1126 (M+H)

Amino acid analysis: Asx 1. 0 (1), Phe 2.0 (2), Tyr 2.0 (2), (no analysis of Trp).

EXAMPLE 10

Synthesis of Compound (II-10 ):

H-Trp-Phe-Asn-Tyr-Tyr-Trp-OH    SEQ ID NO:27

A t-Boc-Trp(CHO)-combined carrier resin and N-protected amino acids, t-Boc-Tyr (Br-Z)-OH, t-Boc-Tyr (Br-Z)-OH, t-Boc-Asn-OH, t-Boc-Phe-OH and t-Boc-Trp (CHO)-OH were used in order, to obtain 1.3 g of the carrier resin combined with the side chain-protected peptides, in, the same manner as in Example 4. Using 0.8 g of the obtained carrier resin, free peptides were cleaved from the resin by treatment with hydrogen fluoride in the same manner as in Example 4, and dissolved in 2M acetic acid and lyophilized to obtain 215.2 mg of a crude product. 4.0 mg of the crude product was purified by HPLC in the same manner as in Example 4, to obtain 2.0 mg of Compound (II-10).

MS analysis [FABMS]: 979 (M+H)

Amino acid analysis: Asx 0.9 (1), Tyr 2.1 (2), Phe 1.0 (1), (no analysis of Trp).

EXAMPLE 11

Synthesis of Compound (II-11):

H-Trp-Phe-Phe-Asn-Tyr-Trp-OH    SEQ ID NO:28

A t-Boc-Trp(CHO)-combined carrier resin and N-protected amino acids, t-Boc-Tyr (Br-Z)-OH, t-Boc-Asn-OH, t-Boc-Phe-OH, t-Boc-Ph e-OH and t-Boc-Trp (CHO)-OH were used in order, to obtain 1.2 g of the carrier resin combined with the side chain-protected peptides, in the same manner as in Example 4. Using 0.8 g of the obtained carrier resin, free peptides were cleaved from the resin by treatment with hydrogen fluoride in the same manner as in Example 4, dissolved in 2M acetic acid and lyophilized to obtain 264.7 mg of a crude product. 8.0 mg of the crude product was purified by HPLC in the same manner as in Example 4, to obtain 4.7 mg of Compound (I-11).

MS analysis [FABMS]: 963 (M+H)

Amino acid analysis: Asx 0. 8 (1), Tyr 1.1 (1), Phe 2.2 (2) (no analysis of Trp).

EXAMPLE 12

Synthesis of Compound (II-12):

H-Trp-Phe-Phe-Tyr-Tyr-Trp-OH    SEQ ID NO:29

A t-Boc-Trp(CHO)-combined carrier resin and N-protected amino acids, t-Boc-Tyr (Br-Z)-OH, t-Boc-Tyr (Br-Z)-OH, t-Boc-Phe-OH, t,Boc-Phe-OH and t-Boc-Trp (CHO)-OH were used in order, to obtain 1.3 g of the carrier resin combined with the side chain-protected peptides, in the same manner as in Example 4. Using 0.8 g of the obtained carrier resin, free peptides were cleaved from the resin by treatment with hydrogen fluoride in the same manner as in Example 4, and dissolved in 2M acetic acid. The solution was lyophilized to obtain 243.4 mg of a crude product. 78.0 mg of the crude product was purified by HPLC in the same manner as in Example 4, to obtain 12.2 mg of Compound (II-12).

MS analysis [FABMS]: 1012 (M+H)

Amino acid analysis: Tyr 2.0 (2), Phe 2.0 (2) (no analysis of Trp).

EXAMPLE 13

Synthesis of Compound (II-13):

H-Phe-Phe-Asn-Tyr-Tyr-Trp-OH    SEQ ID NO:30

A carrier resin combined with t-Boc-Trp(CHO) and N-protected amino acids, t-Boc-Tyr (Br-Z)-OH, t-Boc-Tyr (Br-Z)-OH, t-Boc-Asn-OH, t-Boc-Phe-OH and t-Boc-Phe-OH were used in order, to obtain 1.2 g of the carrier resin combined with the protective peptides, in the same manner as in Example 4. Using 0.8 g of the obtained carrier resin, free peptides were cleaved from the resin by treatment with hydrogen fluoride in the same manner as in Example 4, and dissolved in 2M acetic acid. The solution was lyophilized to obtain 285.5 mg of a crude product. 150.0 mg of the crude product was purified by HPLC in the same manner as in Example 4, to obtain. 39.1 mg of Compound (II-13).

MS analysis [FABMS]: 940 (M+H)

Amino acid analysis: Asx 0.8 (1), Tyr 2.0 (2), Phe 2.2 (2) (no analysis of Trp).

EXAMPLE 14

Synthesis of Compound (I-14):

```
┌─────────────────────────────────────────┐  SEQ ID NO: 31
└─ Gly — Asn — Trp — His — Gly — Thr — Ala — Pro — Asp — OH
```

11.3 mg of Compound (a) obtained in Reference Example 1 was dissolved in 12.3 ml of DMF, 5.2 mg of DEPC and 6.4 mg of TEA were added thereto with cooling at −10° C., and the solution was stirred for 30 minutes. To the resulting reaction solution was added 4.0 mg of α-benzyl-β-diphenylmethyl aspartate which was obtained by reacting diphenyldiazomethane with a benzyl ester of aspartic acid in the same manner as in Example 27, and the mixture was further stirred at 4° C. for 7 days. The obtained compound was purified by reverse phase HPLC equipped with an ODS-AQ column (250×30 mm I.D.), manufactured by YMC CO., using 0–90% acetonitrile containing 0.1% TFA with a linear concentration gradient pattern, and lyophilized to obtain 5 mg of a condensate.

To the condensate were added in order 500 µl of methylene chloride, 10 µl of anisol, 1 µl of 1,2-ethanedithiol and 500 µl of TFA with cooling on ice. The mixture was stirred, and allowed to stand for 30 minutes. The solvent was evaporated under reduced pressure, and the residue was purified by HPLC and lyophilized in the same manner as above, to obtain 2 mg of the de-diphenylmethyl ester condensate.

The obtained ester product was dissolved in 800 µl of DMF, 200 µl of piperidine was added thereto, and the mixture was stirred and then allowed to stand at room temperature for 10 minutes. 300 µl of acetic acid and 450 µl of methanol were then added thereto for neutralization, and the compound was purified by reverse phase HPLC in the same manner as described above and lyophilized, to obtain 1.5 mg of the Fmoc-eliminated ester product.

The obtained Fmoc-eliminated ester product was dissolved in 1.9 ml of DMF, 0.47 mg of DEPC and 0.59 mg of TFA were added thereto with cooling at −10° C. The mixture was allowed to stand for 30 minutes, and the temperature of the mixture was brought back to 4° C. The mixture was stirred for 3 days. The compound was purified by reverse phase HPLC in the same manner as described above and lyophilized, to obtain 1 mg of a benzyl ester of Compound (I-14).

The obtained benzyl ester was then dissolved in 150 µl of methanol containing 50 µl of acetic acid, hydrogen gas was added thereto in the presence of about 1 mg of 10% Pd/C, and the catalytic reduction was carried out with stirring at room temperature for 2 hours. The compound was purified by reverse phase HPLC in the same manner as described above and lyophilized, to obtain 1 mg of Compound (I-14).

MS analysis [FABMS]: 936 (M+H)

Amino acid analysis: Asx 1.9 (2), Gly 2.3 (2) His 1.0 (1), Thr 0.7 (1), Ala 0.9 (1), Pro 1.0 (1), Trp 0.4 (1).

EXAMPLE 15

Synthesis of Compound (I-15):

```
┌─────────────────────────────────────────┐  SEQ ID NO: 32
└ Gly—Asn—Trp—His—Gly—Thr—Ala—Pro—Asp—Trp—OH
```

Step 1: H-Asp (Ot-Bu)-Trp-OBzl (a) 41 mg of Fmoc-Asp(Ot-Bu)-OH was dissolved in 1 ml of methylene chloride. The solution was cooled to 0° C., and then 12 mg of HONSu and 21 mg of DCC were added thereto. The mixture was stirred at 0° C. for 30 minutes. To the mixture were added 1 ml of a methylene chloride containing 33 mg of H-Trp-OBzl.HCl and 14 µl of TEA, followed by stirring,at 0° C. for 3 hours. The insoluble matters were filtered off and the filtrate was washed with cold methylene chloride. The solvent was evaporated under reduced pressure, and the residue was purified by silica gel column chromatography (Wakogel C-200, manufactured by Wako Junyaku Kogyo, 50 g, elution with chloroform/methanol=25/1), to obtain 67 mg of Fmoc-Asp(Ot-Bu-Trp-OBzl as a white powder.

MS analysis [FABMS]: 688 (M+H)

(b) 10 mg of the peptide obtained in (a) was dissolved in 3 ml of DMF, 0.75 ml of piperidine was added thereto, and the solution was allowed to stand at room temperature for 10 minutes. To the reaction solution were added ether and hexane, the precipitated white crystals were filtered off, and dried under reduced pressure to obtain 2 mg of H-Asp(Ot-Bu)-Trp-OBzl.

MS analysis [FABMS]: 466 (M+H)

Step 2: H-Gly-Asn-Trp-His-Gly-Thr-Ala-Pro-Asp-Trp-OBzl SEQ ID NO:67

(a) To 4.4 ml of the Compound (a) obtained in Reference Example 1 was added 5.5 ml of a DMF solution containing 1.7 mg of the dipeptide obtained in Step 1, and the mixture was cooled to 0° C. To the mixture were added in order 0.5 µl of DEPC and 1.0 µl of TEA, and stirring was effected at 0° C. for 5 days. The solvent was then evaporated under reduced pressure, and the residue was again dissolved in 1 ml of DMF and purified by HPLC using a reverse phase column (YMC-Pack ODS-AM312, 150×6 mm I.D., manufactured by YMC Co.), to obtain 320 µg of Fmoc-Gly-Asn-Trp-His-Gly-Thr-Ala-Pro-Asp(Ot-Bu)-Trp-OBzl, SEQ ID NO:67, as a white powder.

(b) To 250 µg of the protected peptide obtained in (a) was added 50 µl of a mixture comprising 900 µl of TFA, 50 µl of 1,2-ethanditihiol, 50 µl of anisol and 5 mg of 2-methylindole, and the mixture was allowed to stand at room temperature for 1.5 hours. Ether was added thereto, and the resulting white precipitate was filtered off and dried, 100 µl of DMF containing 20% piperidine was added thereto, and the mixture was allowed to stand at room temperature for 15 minutes. Again, ether was added thereto, and the resulting white precipitate was filtered off and dried, to obtain 200 µg of H-Gly-Asn-Trp-His-Gly-Thr-Ala-Pro-Asp-Trp-OBzl, SEQ ID NO:67.

Step 3: Compound (I-15)

(a) 66 µg of the peptide obtained in dissolved in Step 2 was dissolved in 60 µl of DMF, and to the solution were added at room temperature 1.6 µl of a DMF containing 0.1M PyBOP, 1.6 µl of a DMF containing 0.1M HOBt and 3 l of a DMF containing 1% NMM, and the mixture was stirred at room temperature for 3 hours. The solvent was then evaporated under reduced pressure, and the product was subjected to purification on a reverse phase HPLC column (YMC-Pack ODS-AM312, 150×6 mm I.D., manufactured by YMC Co.), to obtain 20 µg of a benzyl ester of Compound (I-15).

(b) 250 µg of the benzyl ester obtained in (a) was dissolved in 80 µg of a mixture of methanol and acetic acid at a proportion of 3:1, and about 0.5 mg of 10% Pd/C was added thereto under a nitrogen atmosphere. A hydrogen gas was introduced, and the mixture was stirred at room temperature for 1 hour. The Pd/C was filtered off, and ether was added to the filtrate to generate a white precipitate. The white precipitate was filtered off and dried to obtain 100 µg of Compound (I-15).

MS analysis [FABMS]: 1123 (M+H)

Amino acid analysis: Gly 2.3 (2), Asx 1.6 (2), His 0.9 (1), Thr 1.0 (1), Ala 1.0 (1), Pro 1.1 (1)

EXAMPLE 16

Synthesis of Compound (I-16):

```
┌──────────────────────────────────────────────┐
└ Gly—Asn—Trp—His—Gly—Thr—Ala—Pro—Asp—Gly—OMe  SEQ ID NO:33
```

10 μg of Compound (I-14) obtained in Example 14 was dissolved in 10 μl of DMF, and then 4.3 μg of HOBt, 16.7 μg of PyBOP and 4.9 μg of NMM were added in order to the solution with cooling on ice, and the mixture was allowed to stand for 30 minutes. To the reaction mixture was added 4.0 μg of H-Gly-OMe.HCl, and the mixture was allowed to stand at 4° C. overnight, and was purified in the same manner as in Example 15, by reverse phase HPLC equipped with a YMC Pack ODS-AM 312 column (150×6 mm I.D.) manufactured by YMC Co., and lyophilized to obtain 6 μg of Compound (I-16).

MS analysis [FABMS]: 1008 (M+H)

Amino acid analysis: Asx 1.8 (2), Gly 3.2 (3), His 1.0 (1), Thr 1.0 (1), Ala 0.9 (1), Pro 1.0 (1) (no analysis of Trp)

EXAMPLE 17

Synthesis of Compound (1–17):

```
 ┌─────────────────────────────────────────────────────────────┐
 └─ Gly—Asn—Trp—His—Gly—Thr—Ala—Pro—Asp—Trp—Phe—Phe—Asn—Tyr—Tyr—OH SEQ ID NO:34
```

7.1 mg of Compound (I-1) was dissolved in 2.84 ml of methanol, 25.56 ml of a 0.1M Tris-HCl buffer solution (pH 8.0) and then about 0.3 mg of carboxypeptidase A (C-9762, product of Sigma Co.) were added thereto, and the mixture was stirred at 37° C. overnight. The reaction mixture was acidified by addition of an appropriate amount of hydrochloric acid, and reverse phase HPLC equipped with a NUCLEOSIL 5C18 (250×20 mm I.D., manufactured by Chemco Inc.) was used with a linear concentration gradient pattern wherein an increase in the concentration of acetonitrile in the 0.1% TFA solution from 0% to 50% was effected in 30 minutes, at a flow rate of 10 ml/min to obtain 3.5 mg of Compound (I-17).

MS analysis [FABMS]: 1858 (M+H)

Amino acid analysis: Asx 2.6 (3), Gly 2.2 (2), His 0.9 (1), Thr 1.0 (1), Ala 1.0 (1), Pro 1.1 (1), Tyr 1.8 (2), Phe 1.9 (2), (no analysis of Trp)

EXAMPLE 18

Synthesis of Compound (I-18):

```
 ┌─────────────────────────────────────────────────────────────────┐
 └─ Gly—Asn—Trp—His—Gly—Thr—Ala—Pro—Asp—Trp—Phe—Phe—Asn—Tyr—Tyr—Trp—OH SEQ ID NO:35
```

To 270 μl of a DMF solution containing 0.49 mg of Compound (I-1) were added 375 μg of PyBOP, 97 μg of HOBt and 121 μg of NMM, and the mixture was stirred at room temperature for 1 hour. 80 μl of a DMF solution containing 0.16 mg of H-Trp-OBzl was added thereto and the mixture was stirred at 4° C. for 4 days. The solvent was evaporated under reduced pressure, and the residue was again dissolved in 80 μl of a DMF solution and subjected to HPLC equipped with a reverse phase column (YMC-Pack ODS-AM312, 150×6 mm I.D., manufactured by YMC Co.), with a linear concentration gradient pattern wherein the concentration of acetonitrile in a 0.1% TFA solution was increased from 0% to 90% in 60 minutes, at a flow rate of 1 ml/min, to obtain 70 μg of a benzyl ester of Compound (I-18).

MS analysis [FABMS]: 2320 (M+H)

Next, 70 μg of the benzyl ester was dissolved in 35 μl of DMF, 35 μl of an ammonium formate-saturated methanol and about 0.1 mg of 10% Pd/C were added thereto, and the mixture was stirred at room temperature for 1 hour. The reaction solution was subjected to centrifugation, and the resulting supernatant was recovered, and subjected to purification in the same manner as described above, using a reverse phase column (YMC-Pack ODS-AM312, 150×6 mm I.D., manufactured by YMC Co.), to obtain 25 μg of Compound (I-18).

MS analysis [FABMS]: 2230 (M+H)

Amino acid analysis: Gly 2.2 (2), Asx 2.8 (3), His 0.9 (1), Thr 0.9 (1), Ala 1.0 (1), Pro 1.3 (1), Phe 1.9 (2), Tyr 1.7 (2) (no analysis of Trp)

EXAMPLE 19

Synthesis of Compound (I-19):

```
 ┌─────────────────────────────────────────┐
 └─ Gly—Asn—Trp—His—Gly—Thr—Ala—Pro—Asp—
     Trp—Phe—Phe—Asn—Tyr—Tyr—Trp—Asn—Tyr—Tyr—Trp—OH SEQ ID NO:36
```

Step 1: H-Asn-Tyr-Tyr-Trp-OBzl SEQ ID NO:70.

110 mg of a carrier resin combined with 66 μmol of Fmoc-Tyr(t-Bu) was condensed with Fmoc-Tyr(t-Bu)-OH and Fmoc-Asn(Trt)-OH in order as the N-protected amino acids, for peptide synthesis in the same manner as in Reference Example 3, and free peptides were cleaved from the resin to obtain 89 mg of a crude peptide of Fmoc-Asn-Tyr-Tyr-OH.

Using the same method as in Example 15, 8.2 mg of the above mentioned peptide was condensed with 7.6 mg of H-Trp-OBzl and the obtained peptide was Fmoc-eliminated according to the same method as in Example 15, to obtain 1 mg of H-Asn-Tyr-Tyr-Trp-OBzl, SEQ ID NO:70.

Step 2: Compound (I-19)

Using the same method as in Example 18, 0.29 mg of Compound (I-1) was condensed with 0.10 mg of the above mentioned peptide H-Asn-Tyr-Tyr-Trp-OBzl to obtain a benzyl ester. Debenzylation was effected according to the same method as used in Example 18 to obtain 19 µg of Compound (I-19).

MS analysis [FABMS]: 2671 (M+H)

Amino acid analysis: Gly 2.3 (2), Asx 3.6 (4), His 0.9 (1), Thr 1.0 (1), Ala 1.0 (1), Pro 1. (no analysis of Trp)

EXAMPLE 20

Synthesis of Compound (I-20):

```
┌─────────────────────────────────────────────────────────────────┐
└─ Gly—Asn—Trp—His—Gly—Thr—Ala—Pro—Asp—Trp—Phe—Phe—Asn—Tyr—
```
Tyr—Trp—Val—Tyr—Phe—Ala—His—Leu—Asp—Ile—Ile—Trp—OH SEQ ID NO:37

Step 1: H-Val-Tyr-Phe-Ala-His-Leu-Asp(OBzl)-Ile-Ile-Trp-OBzl, SEQ ID NO:71,

Fmoc-Val-Tyr-Phe-Ala-His-Leu-Asp(OBzl)-Ile-Ile-OH SEQ ID NO:72 was synthesized in the same manner as in Reference Example 3, by condensing an Fmoc-Ile-combined carrier resin in order with the N-protected amino acids Fmoc-Ile-OH, Fmoc-Asp(OBzl)-OH, Fmoc-Leu-OH, Fmoc-His(Trt)-OH, Fmoc-Ala-OH, Fmoc-Phe-OH, Fmoc-Tyr(t-Bu)-OH and Fmoc-Val-OH therewith. Cleaving from the resin was effected in a similar manner to obtain the above mentioned crude peptide.

2.0 mg of the obtained peptide was dissolved in 200 µl of dry DMF, and to the solution were added in order, with cooling on ice, 10 µl of dry DMF containing 42 mg/ml HOBt, 10 µl of dry DMF containing 162 mg/ml PyBOP, 10 µl of dry DMF containing 34.3 µl/ml NMM and 10 µl of dry DMF containing 62 mg/ml of H-Trp-OBzl hydrochloride. The mixture was allowed to stand at 4° C. overnight and the insoluble matters were filtered off and the filtrate was purified by reverse phase HPLC. The column used was a Chemco Pack NUCLEOSIL 5C18, 250×20 mm I.D. (manufactured by Chemco Inc.), and the dilution was effected with a linear concentration gradient pattern using 0–90% acetonitrile containing 0.1% TFA. The fractions containing the subject compound were lyophilized to obtain 2.7 mg of Fmoc-Val-Tyr-Phe-Ala-His-Leu-Asp(OBzl)-Ile-Ile-Trp-OBzl, SEQ ID NO:71.

Next, 100 µl of dry DMF containing 20% piperidine was added to the obtained peptide above and the mixture was allowed to stand at room temperature for 5 minutes. Diethylether was added thereto, and the precipitated product was washed with diethyl ether and dried under reduced pressure, to obtain 467 µg of H-Val-Tyr-Phe-Ala-His-Leu-Asp(OBzl)-Ile-Ile-Trp-OBzl SEQ ID NO:71.

(2) Compound (I-20)

```
┌─────────────────────────────────────────────────────────────────┐
└─ Gly—Asn—Trp—His—Gly—Thr—Ala—Pro—Asp—Trp—Phe—Phe—Asn—Tyr—Tyr—Phe—OH SEQ ID NO:39
```

In the same manner as in Example 18, 0.14 mg of Compound (I-1) was condensed with 10 mg of the peptide obtained in Step 1 above to obtain a benzyl ester, and debenzylation was effected to obtain 10.5 µg of Compound (I-20).

MS analysis [FABMS]: 3303 (M+H)

Amino acid analysis: Gly 2.3 (2), Asx 4.0 (4), His 1.8 (2), Thr 1.0 (1), Ala 2.0 (2), Pro 1.2 (1), Phe 2.7 (3), Tyr 2.6 (3), Val 0.9 (1), Leu 1.0 (1), Ile 1.7 (2), (no analysis of Trp)

EXAMPLE 21

Synethesis of compound (I-21):

-continued
```
┌─────────────────────────────────────────────────────────────────┐
└─ Gly—Asn—Trp—His—Gly—Thr—Ala—Pro—Asp—
```
Trp—Phe—Phe—Asn—Tyr—Tyr—Ala—OH SEQ ID NO:38

To 0.2 mg of a DMF solution containing 0.22 mg of Compound (I-17) obtained in Example 17 were added 187 µg of PyBOP, 49 µg of HOBt and 61 µg of NMM, and the mixture was stirred at room temperature for 1 hour. Next, 0.12 mg of H-Ala-OBzl.TosOH and 35 µg of a DMF solution containing 35 µg of NMM were added thereto, and the mixture was stirred at 4° C. for 2 days. The solvent was removed by evaporation under reduced pressure, and the resulting residue was dissolved in 1 mg of DMF and then subjected to purification by HPLC in the same manner as in Example 15, to obtain 36 µg of a benzyl ester of Compound (I-21).

MS analysis [FABMS]:2019 (M+H)

36 µg of the obtained benzyl ester was dissolved in 20 µg of DMF, 20 µg of a methanol solution saturated with ammonium formate and about 0.1 mg of 10% Pd/C were added thereto, and the mixture was stirred at room temperature for 1 hour. The reaction solution was subjected to centrifugation and the resulting supernatant was collected. The supernatant was then subjected to purification by reverse phase HPLC according to the same method as used in Example 18, and the crude product was separated and purified to obtain 27 µg of Compound (I-21).

MS analysis [FABMS]: 1929 (M+H)

Amino acid analysis: Gly 2.2 (2), Asx 2.6 (3), His 1.0 (1), Thr 1.1 (1), Ala 2.0 (2), Pro 1.1 (1), Phe 2.0 (2), Tyr 1.9 (2), (no analysis of Trp)

EXAMPLE 22

Synthesis of compound (I-22):

In the same manner as in Example 15, 0.22 mg of Compound (I-17) was condensed with 0.15 mg of H-Phe-OBzl.TosOH to obtain a benzyl ester, and debenzylation was effected to obtain 27 µg of Compound (I-22).

MS analysis [FABMS]: 2005 (M+H)

Amino acid analysis: Gly 2.1 (2), Asx 2.6 (3), His 1.0 (1), Thr 1.0 (1), Ala 1.0 (1), Pro 1.0 (1), Phe 3.0 (3), Tyr 2.0 (2), (no analysis of Trp)

EXAMPLE 23

Synthesis of Compound (I-23):

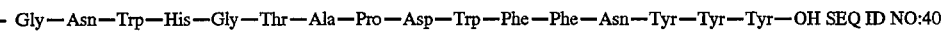
Gly—Asn—Trp—His—Gly—Thr—Ala—Pro—Asp—Trp—Phe—Phe—Asn—Tyr—Tyr—Tyr—OH SEQ ID NO:40

In the same method as in Example 15, 0.22 mg of Compound (I-17) was condensed with 0.16 mg of H-Tyr-OBzl.TosOH to obtain a benzyl ester, and debenzylation was carried out to obtain 30 µg of Compound (I-23).

MS analysis [FABMS]: 2021 (M+H)

Amino acid analysis: Gly 2.2 (2), Asx 2.6 (3), His 1.0 (1), Thr 1.0 (1), Ala 1.0 (1), Pro 1.1 (1), Phe 2.0 (2), Tyr 2.9 (3), (no analysis of Trp)

EXAMPLE 24

Synthesis of Compound (I-24):

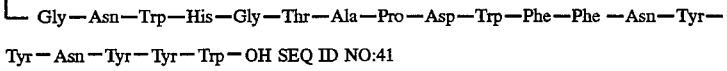
Gly—Asn—Trp—His—Gly—Thr—Ala—Pro—Asp—Trp—Phe—Phe —Asn—Tyr—
Tyr—Asn—Tyr—Tyr—Trp—OH SEQ ID NO:41

In the same method as in Example 15, 0.22 mg of Compound (I-17) was condensed with 0.17 mg of H-Asn-Tyr-Tyr-Trp-OBzl, SEQ ID NO:70, to obtain a benzyl ester, and debenzylation was effected to obtain 36 µg of Compound (I-24).

MS analysis [FABMS]: 2485 (M+H)

Amino acid analysis: Gly 2.1 (2), Asx 4.0 (4), His 1.0 (1), Thr 1.0 (1), Ala 1.0 (1), Pro 1.1 (1), Phe 1.9 (2), Tyr 3.9 (4), (no analysis of Trp)

EXAMPLE 25

Synthesis of Compound (I-25):

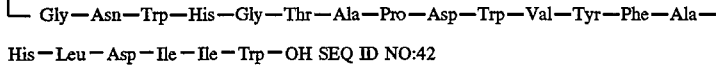
Gly—Asn—Trp—His—Gly—Thr—Ala—Pro—Asp—Trp—Val—Tyr—Phe—Ala—
His—Leu—Asp—Ile—Ile—Trp—OH SEQ ID NO:42

In 150 µg of Compound (I-15) was dissolved 113 µl of dry DMF, and to the solution were added in order, with cooling on ice, 100 µl each of 0.53 mg/ml HOBt, 2.0 mg/ml PyBOP and 0.71 µl/ml NMM, which were prepared with dry DMF. To the resulting mixture was added 87 µl of a solution in dry DMF containing 2.4 mg/ml H-Val-Tyr-Phe-Ala-His-Leu-Asp(OBzl)-Ile-Ile-Trp-OBzl, SEQ ID NO:71, obtained in Example 20. The resulting mixture was allowed to stand for 5 hours with cooling on ice, and purified by reverse phase HPLC in the same manner as in Example 15. The fractions containing the condensate were lyophilized to obtain 140 µg of a benzyl ester of Compound (I-25). Next, 200 µl of a methanol solution containing 25% acetic acid and 50 µl of dry DMF were added thereto in a nitrogen atmosphere, 0.5 mg of 10% Pd/C was further added thereto, hydrogen gas was introduced, and the mixture was vigorously stirred at room temperature for 1 hour. The catalyst was filtered off and the filtrate was purified by reverse phase HPLC according to the same method as in Example 15. The solvent of the fractions containing the subject compound was evaporated under reduced pressure to obtain 6.5 µg of Compound (I-25).

MS analysis [FABMS]: 2472 (M+H)

Amino acid analysis: Asx 2.6 (3), Gly 2.0 (2), His 1.6 (2), Thr 0.9 (1), Ala 1.6 (2), Pro 0.8 (1), Val 0.7 (1), Tyr 0.9 (1), Phe 0.8 (1) (no analysis of Trp)

EXAMPLE 26

Synthesis of Compound (I-26):

H-Gly-Asn-Trp-His-Gly-Thr-Ala-Pro-Asp-Trp-Val-Tyr-Phe-Ala-His-Leu-AsD-Ile-Ile-TrD-OH    SEQ ID NO:43

In the same manner as in Reference Example 3, 20 mg of a carrier resin combined with 10.4 µmol of Pmoc-Trp was condensed in order with Fmoc-Ile-OH, Fmoc-Ile-OH, Fmoc-Asp(Ot-Bu)-OH, Fmoc-Leu-OH, Fmoc-His(Trt)-OH, Fmoc-Ala-OH, Fmoc-Phe-OH, Fmoc-Tyr(t-Bu)-OH, Fmoc-Val-OH, Fmoc-Trp-OH, Fmoc-Asp(Ot-Bu)-OH, Fmoc-Pro-OH, Fmoc-Ala-OH, Fmoc-Thr(t-Bu)-OH, Fmoc-Gly-OH, Fmoc-His(Trt)-OH, Fmoc-Trp-OH, Fmoc-Asn(Trt)-OH and Fmoc-Gly-OH as the N-protected amino acids. The same procedure as in Reference Example 3 was repeated except that piperidine treatment in (b) was effected in the final step. The free peptide was cleaved from the resin in the same manner as in Reference Example 3, to obtain 25 mg of a crude product. 4.0 mg of the crude product was purified by HPLC according to the same method as used in Example 4, to obtain 1.8 mg of Compound (I-26).

MS analysis [FABMS]: 2400 (M+H)

Amino acid analysis: Gly 2.4 (2), Ala 2.0 (2), Asx 2.9 (3), His 1.9 (2), Ile 1.0 (2), Leu 0.9 (1), Phe 0.9 (1), Pro 1.1 (1), Thr 1.1 (1), Tyr 0.9 (1), Val 0.7 (1), (no analysis of Trp)

EXAMPLE 27

Synthesis of Compound (I-27):

┌─────────────────────────────────────────────────────────────────────────┐
└─ Gly—Asn—Trp—His—Gly—Thr—Ala—Pro—Asp—Trp—Ile—Ile—Trp—OH SEQ ID NO:44

Step 1: H-Ile-Ile-Trp-OCHPh$_2$

Fmoc-Ile-Ile-Trp-OH was synthesized in the same manner as in Reference Example 3, by condensing a carrier resin combined with Fmoc-Trp with Fmoc-Ile-OH and Fmoc-Ile-OH in order as the N-protected amino acids, and a crude product of the above mentioned peptide was cleaved from the resin. To 126 µg of the peptide were added 200 µl of methanol and 200 µl methylene chloride, and the peptide was dissolved in the mixture, and 30 µl of methylene chloride containing 7.8 mg/ml diphenyldiazomethane and 30 µl of methanol containing 28.6 µl/ml hydrochloric acid were added thereto with cooling on ice. The mixture was allowed to stand with cooling on ice for 2 hours, and the temperature of the mixture was brought back to room temperature. The mixture was allowed to stand overnight. The insoluble matters were filtered off and the filtrate was purified by reverse phase HPLC (YMC-Pack ODS-AM312 column, manufactured by YMC Co.) in the same manner as in Example 20. Lyophilization was effected to obtain 75 µg of Fmoc-Ile-Ile-Trp-OCHPh$_2$. Next, 100 µl of dry DMF containing 20% piperidine solution was added thereto, and the mixture was allowed to stand at room temperature for 5 minutes. The insoluble matters were filtered off and the filtrate was purified by reverse phase HPLC in the same manner as above. The solvent of the fractions containing the subject compound was evaporated under reduced pressure to obtain 32 µg of H-Ile-Ile-Trp-OCHPh$_2$.

Step 2: Compound (I-27)

64 µg of Compound (I-15) obtained in Example 15 was dissolved in 40 l of dry DMF. To the mixture were added in order 20 µl each of 1.1 mg/ml HOBt, 4.1 mg/ml PyBOP, 1.5 µl/ml NMM and 31.7 mg/ml H-Ile-Ile-Trp-OCHPh$_2$, each of which was prepared with dry DMF with cooling on ice. The mixture was allowed to stand with cooling on ice for 2 hours, and the reaction solution was purified by reverse phase HPLC in the same manner as in Example 15. The solvent of the obtained fractions was evaporated under reduced pressure to obtain 37 µg of a benzhydryl ester of Compound (I-27). Next, 25 µl of a mixed solution of 900 µl of TFA, 50 µl of anisol, 50 µl of 1,2-ethanedithiol and 5 mg of 2-methylindole was added thereto, and the mixture was stirred at room temperature for one hour. To the reaction solution was added 0.5 ml of diethylether, and Compound (I-27) was crystallized, washed with ether and dried under reduced pressure to obtain 10.1 µg of Compound (I-27).

MS analysis [FABMS]: 1535 (M+H)

Amino acid analysis: Asx 1.7 (2), Gly 2.1 (2), His 0.9 (1), Thr 1.0 (1), Ala 1.0 (1), Pro 1.3 (1), Ile 2.0 (2), (no analysis of Trp)

EXAMPLE 28

Synthesis of Compound (I-28):

Step 1: H-Leu-Tyr-Phe-Ala-His-Gln-Asp (OBz 1)-Val-Ile-Trp-OBz 1 SEQ ID NO:73

Of Compound (d) obtained in Reference Example 4, 555 µg was dissolved in 200 µl of dry DMF, and to the solution were added in order, with cooling on ice, 10 µl each of 15.9 mg/ml HOBt, 61.2 mg/ml PyBOP, 21.5 µl/ml NMM and then 20 µl of 7.8 mg/ml H-Trp-OBzl hydrochloride, each of which was prepared with dry DMF. The reaction solution was allowed to stand at 4° C. overnight and the insoluble matters were filtered off and the filtrate was purified by reverse phase HPLC in the same manner as in Reference Example 3. Using a Chemco Pack NUCLEOSIL 5C18, 250×20 mm I.D. (manufactured by Chemco Inc.) column, lyophilization was effected. Next, to the lyophilized product was added 100 l of a 20% piperidine solution prepared with DMF, and the mixture was allowed to stand at room temperature for 5 minutes. The solution was then concentrated to 50 µl under reduced pressure, diethylether was added thereto for precipitation, and the mixture was further washed with ether and dried under reduced pressure to obtain 250 µg of H-Leu-Tyr-Phe-Ala-His-Gln-Asp(OBzl)-Val-Ile-Trp-OBzl SEQ ID NO:73.

Step 2: Compound (I-28)

Compound (I-15) obtained in Example 15 was dissolved in 100 l of dry DMF, and 50 µl each of 0.72 mg/ml HOBt, 2.8 mg/ml PyBOP, 1.0 µl/ml NMM and 2.5 mg/ml of the above mentioned peptide each of which was prepared with dry DMF were added in order with cooling on ice. The mixture was allowed to stand at 4° C. overnight, and the insoluble matters were filtered off and the filtrate was purified by reverse phase HPLC in the same manner as in Example 15. The obtained fractions were lyophilized to obtain 66 µg of a benzyl ester of Compound (I-28). Next, 30 µl of dry DMF and 30 µl of methanol saturated with ammonium formate were added thereto, a small amount of 10% Pd/C was further added thereto, and the mixture was vigorously stirred at room temperature for one hour. Then, the catalyst was filtered off and the filtrate was purified by reverse phase HPLC according to the same method as used in Example 15. The column used was a YMC Pack ODS-AM312 (150×6 mm I.D.) manufactured by YMC Co. The solvent of the fractions containing the subject compound was evaporated under reduced pressure to obtain 1.2 µg of Compound (I-28).

MS analysis [FABMS]: 2397 (M+H)

Amino acid analysis: Asx 2.6 (3), Glx 1.0 (1), Gly 2.2 (2), His 2.0 (2), Thr 1.0 (1), Ala 2.0 (2), Pro 1.2 (1), Tyr 1.1 (1), Val 0.9 (1), Ile 0.7 (1), Leu 1.1 (1), Phe 1.3 (1), (no analysis of Trp)

SEQ ID NO:45

┌─────────────────────────────────────────────────────────────────────────┐
└─ Gly—Asn—Trp—His—Gly—Thr—Ala—Pro—Asp—Trp—Leu—Tyr—Phe—Ala—

His—Gln—Asp—Val—Ile—Trp—OH

EXAMPLE 29

Synthesis of Compound (I-29):

SEQ ID NO:46

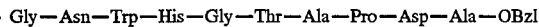
Gly—Asn—Trp—His—Gly—Thr—Ala—Pro—Asp—Ala—OBzl 10.0 μg of Compound (I-14) obtained in Example 14 was dissolved in 10 μl of DMF, 4.3 μg of HOBt, 16.7 μg of PyBOP and 4.9 μg of NMM were added thereto with cooling on ice, and the mixture was allowed to stand for 30 minutes. To the reaction solution was added 11.3 μg of H-Ala-OBzl.TosOH, the solution was allowed to stand at 15° C. overnight, and then purified by reverse phase HPLC equipped with a YMC Pack ODS-AM312 column (150×6 mm I.D.) manufactured by YMC Co., according to the same method as used in Example 14 and lyophilized, to obtain 5.0 μg of Compound (I-29).

MS analysis [FABMS]: 1098 (M+H)

Amino acid analysis: Asx 1.6 (2), Gly 2.2 (2), His 1.0 (1), Thr 0.9 (1), Ala 1.8 (2), Pro. 1.2 (1), (no analysis of Trp)

EXAMPLE 30

Synthesis of Compound (I-30):

SEQ ID NO:47

Gly—Asn—Trp—His—Gly—Thr—Ala—Pro—Asp—Ala—OBzl 10.0 μg of Compound (I-14) obtained in Example 14 was dissolved in 10 μg of DMF, 4.3 μg of HOBt, 16.7 μg of PyBOP and 4.9 μg of NMM were added thereto with cooling on ice, and the mixture was allowed to stand for 30 minutes. To the reaction solution was added 4.0 μg of H-Val-OBzl.TosOH, and the solution was allowed to stand at 15° C. overnight and then purified by reverse phase HPLC equipped with a YMC Pack ODS-AM312 column (150×6 mm I.D.) manufactured by YMC Co., according to the same method as used in Example 14 and lyophilized, to obtain 7.0 μg of Compound (I-30).

MS analysis [FABMS]: 1126 (M+H)

Amino acid analysis: Asx 1.8 (2), Gly 2.2 (3), His 1.0 (1), Thr 1.0 (1), Ala 1.1 (1), Pro 1.0 (1), Val 1.2 (1), (no analysis of Trp)

EXAMPLE 31

Synthesis of Compound (I-31):

SEQ ID NO:48

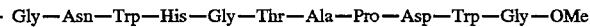
Gly—Asn—Trp—His—Gly—Thr—Ala—Pro—Asp—Trp—Gly—OMe

To 30 μg of Compound (I-15) obtained in Example 15 was added 30 μl of dry DMF, and then 10 μl each of 0.53 mg/ml HOBt, 2.0 mg/ml PyBOP and 0.71 μl/ml NMM each of which was prepared with dry DMF, were added in order, with cooling on ice. 40 μl of dry DMF containing 0.064 mg/ml H-Gly-OMe was further added to the reaction solution. The mixture was then allowed to stand for one hour with cooling on ice, and the temperature of the mixture was brought back to room temperature. The mixture was allowed to stand for an additional 2 hours. Next, the insoluble matters were filtered off and the filtrate was purified by reverse phase HPLC according to the same method as used in Example 15. The solvent of the fractions containing the condensate was then evaporated under reduced pressure to obtain 8.0 μg of Compound (I-31).

MS analysis [FABMS]: 1194 (M+H)

Amino acid analysis: Asx 1.8 (2), Gly 2.4 (2), His 0.9 (1), Thr 1.1 (1), Ala 1.0 (1), Pro 1.2 (1), (no analysis of Trp)

EXAMPLE 32

Synthesis of Compound (I-32):

SEQ ID NO:49

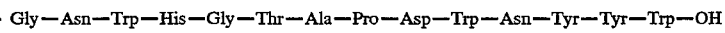
Gly—Asn—Trp—His—Gly—Thr—Ala—Pro—Asp—Trp—Asn—Tyr—Tyr—Trp—OH

In the same manner as in Reference Example 3, the carrier resin combined with Fmoc-Tyr was condensed with the N-protected amino acids, Fmoc-Tyr(t-Bu)-OH and Fmoc-Asn(Trt)-OH, in order to synthesize a protected peptide, and the crude peptide Fmoc-Asn-Tyr-Tyr-OH was cleaved from the carrier resin. Next, 8.2 mg of the obtained crude peptide was dissolved in 5 ml of dry DMF, and 250 μl each of 15.4 mg/ml HOBt, 59.6 mg/ml PyBOP, 21 μl/ml NMM and 15.2 mg/ml H-Trp-OBzl hydrochloride each of which was prepared with dry DMF, was added in order with cooling on ice. The mixture was allowed to stand at 4° C. for 5 hours, and the insoluble matters were filtered and the filtrate was purified by reverse phase HPLC. The column used was a Chemco Pack NUCLEOSIL 5C18 (250×20 mm I.D.), manufactured by Chemco Inc. The fractions containing the subject compound were lyophilized to obtain 6.75 mg of Fmoc-Asn-Tyr-Tyr-Trp-OBzl, SEQ ID NO:70.

Next, 100 μl of dry DMF containing 20% piperidine was added to 2.7 mg of the subject compound, the mixture was allowed to stand at room temperature for 5 minutes, diethylether was added thereto for crystallization, and the obtained crystal was washed with ether and dried under reduce pressure to obtain 2.25 mg of H-Asn-Tyr-Tyr-Trp-OBzl, SEQ ID NO:70.

Next, 100 μl of dry DMF was added to 100 μl of Compound (I-15) obtained in Example 15, and 50 μg each of 0.72 mg/ml HOBt, 2.8 mg/ml PyBOP, 1 μl/ml NMM and 0.45 μg/μl H-Asn-Tyr-Tyr-Trp-OBzl, SEQ ID NO:70, each of which was prepared with dry DMF was added in order, with cooling on ice. The reaction solution was then allowed to stand for 3 hours with cooling on ice. The insoluble matters were filtered off and the filtrate was purified by reverse phase HPLC according to the same method as in Example 25. The solvent of the obtained fractions was evaporated under reduced pressure to obtain 80 μg of a benzyl ester of Compound (I-32).

Next, 30 µl of dry DMF and 30 µl of methanol saturated with ammonium formate were added to 80 µg of the benzyl ester obtained above, and a minute amount of 10% Pd/C was further added thereto, and the mixture was vigorously stirred at room temperature for 1 hour. Then, the catalyst was filtered off and the filtrate was purified by reverse phase HPLC in the same manner as above. The column used was an ODS-AM312, manufactured by YMC Co. The solvent of the fractions containing the subject compound was evaporated under reduced pressure to obtain 42 µg of Compound (I-32).

MS analysis [FABMS]: 1750 (M+H)

Amino acid analysis: Asx 2.0 (2), Gly 2.4 (2), His 1.1 (1), Thr 0.9 (1), Ala 1.0 (1), Pro 1.4 (1), Tyr 2.0 (2), (no analysis of Trp)

EXAMPLE 33 was prepared with dry DMF, was added thereto in order with cooling on ice, and 50 µl of a dry DMF solution containing 3.0 mg/ml of the peptide obtained in Step 1 above was further added thereto. The reaction solution was allowed to stand for 3 hours with cooling on ice, and the insoluble matters were filtered off and the filtrate was purified by reverse phase HPLC (Column: ODS-AM312, manufactured by YMC Co.). The solvent of the fractions containing the condensate was evaporated under reduced pressure to obtain 110 µg of a benzyl ester of Compound (I-33). Next, 50 µl of dry DMF and 50 µl of methanol saturated with ammonium formate were added to 110 µg of the benzyl ester, a minute amount of 10% Pd/C was further added thereto, and the mixture was vigorously stirred at room temperature for 2 hours. Then, the catalyst was filtered off and the filtrate was purified by reverse phase HPLC in the same manner as above. The solvent of the fractions containing the subject compound was then evaporated under reduced pressure to obtain 2.0 µg of Compound (I-33).

SEQ ID NO:50

Synthesis of Compound (I-33): Gly—Asn—Trp—His—Gly—Thr—Ala—Pro—Asp—Trp—Val—Tyr—Phe—Ala—Phe—Phe—Asn—Tyr—Tyr—Trp—OH Step 1(1) H-Val-Tyr-Phe-Ala-Phe-Phe-Asn-Tyr-Tyr-Trp-OBzl SEQ ID NO:74

In the same manner as in Reference Example 3, a carrier resin combined with Fmoc-Tyr was condensed with the N-protected amino acids, Fmoc-Tyr(t-Bu)-OH, Fmoc-Asn(Trt)-OH, Fmoc-Phe-OH, Fmoc-Phe-OH, Fmoc-Ala-OH, Fmoc-Phe-OH, Fmoc-Tyr(t-Bu)-OH and Fmoc-Val-OH were combined therewith in order, and the crude peptide Fmoc-Val-Tyr-Phe-Ala-Phe-Phe-Asn-Tyr-Tyr-OH, SEQ ID NO:75, was cleaved from the carrier resin.

Next, 4.9 mg of the obtained peptide was dissolved in 2 mg of dry DMF, and 0.5 mg each of 2.8 mg/ml HOBt, 10.6 mg/ml PyBOP, 4 µl/ml NMM and 2.7 mg/ml H-Trp-OBzl hydrochloride, each of which was prepared with dry DMF, was added in order with cooling on ice. The mixture was allowed to stand at 4° C. overnight, and the insoluble matters were filtered off and the filtrate was purified by reverse phase HPLC. The column used was a Chemco Pack NUCLEOSIL 5C18 (250×20 mm I.D.), manufactured by Chemco Inc. The fractions containing the condensate were lyophilized to obtain 5.4 mg of Fmoc-Val-Tyr-Phe-Ala-Phe-Phe-Asn-Tyr-Tyr-Trp-OBzl, SEQ ID NO:74.

To 5.4 mg of this compound was added 100 µl of dry DMF containing 20% piperidine, and the mixture was allowed to stand at room temperature for 5 minutes. Diethylether was then added thereto for crystallization, and the crystals were washed with ether and dried under reduced pressure to obtain 3.0 mg of H-Val-Tyr-Phe-Ala-Phe-Phe-Asn-Tyr-Tyr-Trp-OBzl, SEQ ID NO:74.

Step 2: Compound (I-33)

To 100 µg of Compound (I-15) obtained in Example 15 was added 100 µl of dry DMF, 50 µl each of 0.72 mg/ml HOBt, 2.8 mg/ml PyBOP and 1 µl/ml NMM, each of which MS analysis [FABMS]: 2525 (M+H)

Amino acid analysis: Asx 3.0 (3), Gly 2.5 (2), His 1.1 (1), Thr 1.3 (1), Ala 2.0 (2), Pro 1.1 (1), Phe 3.0 (3), Tyr 2.9 (3), Val 1.0 (1), (no analysis of Trp)

EXAMPLE 34

Synthesis of Compound (I-34):

SEQ ID NO:51

Gly—Asn—Trp—His—Gly—Thr—Ala—Pro—Asp—Trp—Val—Tyr—Tyr—Ala—His—Leu—Asp—Ile—Ile—Trp—OH

Step 1: H-Val-Tyr-Tyr-Ala-His-Leu-Asp(OBzl)-Ile-Ile-Trp-OBzl SEQ ID NO:75

In the same manner as in Reference Example 3, a carrier resin combined with Fmoc-Ile was condensed with the N-protected amino acids, Fmoc-Ile-OH, Fmoc-Asp(OBzl)-OH, Fmoc-Leu-OH, Fmoc-His(Trt)-OH, Fmoc-Ala-OH, Fmoc-Tyr(t-Bu)-OH, Fmoc-Tyr(t-Bu)-OH and Fmoc-Val-OH in order to synthesize the protected peptide, and the crude peptide Fmoc-Val-Tyr-Tyr-Ala-His-Leu-Asp(OBzl)-Ile-Ile-OH, SEQ ID NO:76, was cleaved from the carrier resin. 4.1 mg of the obtained peptide was dissolved in 1 ml of dry DMF, and 0.5 ml each of 3 mg/ml HOBt, 12 mg/ml PyBOP, 4 µl/ml NMM and 3 mg/ml H-Trp-OBzl hydrochloride, each of which was prepared with dry DMF, was added in order with cooling on ice. The mixture was allowed to stand at 4° C. overnight, and the insoluble matters were filtered off and the filtrate was purified by reverse phase HPLC. The column used was a Chemco Pack NUCLEOSIL 5C18 (250×20 mm I.D.), manufactured by Chemco Inc., and the elution was effected wit a linear concentration gradient pattern using 0–90% acetonitrile containing 0.1% TFA.

The fractions containing the subject compound were lyophilized to obtain 2.95 mg of Fmoc-Val-Tyr-Tyr-Ala-His-Leu-Asp(OBzl)-Ile-Ile-Trp-OBzl, SEQ ID NO:75.

To 2.95 mg of the obtained peptide was added 100 µl of dry DMF containing 20% piperidine, and the mixture was allowed to stand at room temperature for 5 minutes. Diethylether was then added thereto for crystallization of the subject compound, and the crystals were washed with ether and dried under reduced pressure to obtain 1.87 mg of H-Val-Tyr-Tyr-Ala-His-Leu-Asp(OBzl)-Ile-Ile-Trp-OBzl, SEQ ID NO:75.

Step 2: Compound (I-34)

To 100 µg of Compound (I-15) obtained in Example 15 was added 100 µl of dry DMF, 50 µl each of 0.72 mg/ml HOBt, 2.8 mg/ml PyBOP and 1 µl/ml NMM, each of which was prepared with dry DMF, was added thereto in order with cooling on ice, and 50 µl of a dry DMF solution containing 2.2 mg/ml of the compound obtained in Step 1 above was further added thereto. The reaction solution was allowed to stand for 3 hours with cooling on ice, and the insoluble matters were filtered off and the filtrate was purified by reverse phase HPLC. The column used was an ODC-AM312, manufactured by YMC Co. The solvent of the fractions containing the condensate was evaporated under reduced pressure to obtain 74.5 µg of a benzyl ester of Compound (I-34). Next, 30 µl of dry DMF and 30 µl of methanol saturated with ammonium formate were added to the 74.5 µg of the benzyl ester, a minute amount of 10% Pd/C was further added thereto, and the mixture was vigorously stirred at room temperature for 2 hours. The catalyst was filtered off and the filtrate was purified by reverse phase HPLC in the same manner as above. The solvent of the fractions containing the subject compound was then evaporated under reduced pressure to obtain 0.74 µg of Compound (I-34).

MS analysis [FABMS]: 2398 (M+H)

Amino acid analysis: Asx 2.8 (3), Gly 2.8 (2), His 1.9 (2), Thr 1.1 (1), Ala 2.0 (2), Pro 1.3 (1), Val 1.0 (1), Tyr 1.6 (2), Leu 1.0 (1), Ile 2.4 (2), (no analysis of Trp)

EXAMPLE 35

Example 17. The fractions containing the peptide were lyophilized to obtain 5.7 mg of Fmoc-Ala-His-Leu-Asp (OBzl)-Ile-Ile-Trp-OBzl, SEQ ID NO:76.

To the 5.7 mg of the peptide was added 150 µl of dry DMF containing 20% piperidine, and the mixture was allowed to stand at room temperature for 5 minutes. Diethylether was then added thereto for crystallization, and the crystals were washed with ether and dried under reduced pressure to obtain 964 µg of H-Ala-His-Leu-Asp(OBzl)-Ile-Ile-Trp-OBzl, SEQ ID NO:76.

Step 2: Compound (I-35)

To 100 µg of Compound (I-15) obtained in Example 15 was added 130 µg of dry DMF, 50 µl each of 0.72 mg/ml HOBt, 2.8 mg/ml PyBOP and 1 µl/ml NMM, each of which was prepared with dry DMF, was added thereto in order with cooling on ice, and 19 µl of a dry DMF containing 6 mg/ml of the compound obtained in Step 1 above was further added thereto. The reaction solution was allowed to stand for 5 hours with cooling on ice, and the insoluble matters were filtered off and the filtrate was purified by reverse phase HPLC according to the same method as used in Example 15. The solvent of the fractions containing the condensate was evaporated under reduced pressure to obtain 172 µg of a benzyl ester of Compound (I-35). Next, 50 µl of dry DMF and 50 µl of an ammonium formate-saturated methanol were added to the 172 µg of the benzyl ester, a minute amount of 10% Pd/C was further added thereto, and the mixture was vigorously stirred at room temperature. The catalyst was filtered off and the filtrate was purified by reverse phase HPLC in the same manner as above. The solvent of the fractions containing the subject compound was then evaporated under reduced pressure to obtain 56 µg of Compound (I-35).

MS analysis [FABMS]: 1973 (M+H)

Amino acid analysis: Asx 2.7 (3), Gly 2.1 (2), His 2.1 (2), Thr 1.1 (1), Ala 2.0 (2), Pro 1.0 (1), Phe 1.0 (1), Ile 1.9 (2), Leu 1.1 (1), (no analysis of Trp)

SEQ ID NO:52

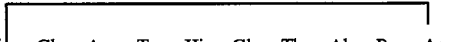

Step 1: H-Ala-His-Leu-Asp (OBz 1)-Ile-Ile-Trp-OBzl SEQ ID NO:76

In the same manner as in Reference Example 3, a carrier resin combined with Fmoc-Ile was condensed in order with the N-protected amino acids, Fmoc-Ile-OH, Fmoc-Asp (OBzl)-OH, Fmoc-Leu-OH, Fmoc-His(Trt)-OH and Fmoc-Ala-OH, and the crude peptide Fmoc-Ala-His-Leu-Asp (OBzl)-Ile-Ile-OH, SEQ ID NO:77, was cleaved from the carrier resin. 9.9 mg of the obtained peptide was dissolved in 1 ml of dry DMF, and 2.7 mg of HOBt, 40.4 mg of PyBOP and 4.4 ml of NMM were added to the solution at room temperature and the mixture was stirred for 5 minutes. 1 ml of 3.3 mg/ml H-Trp-OBzl hydrochloride as prepared with dry DMF was added thereto. The mixture was allowed to stand at room temperature for 3 hours, and the insoluble matters were filtered off and the filtrate was purified by reverse phase HPLC according to the same method as in

EXAMPLE 36

Synthesis of Compound (I-36):

SEQ ID NO:53

Step 1: H-Asp (Ot-Bu) -Trp-Phe-Phe-Asn-Tyr-Tyr-Trp-OBzl SEQ ID NO:77

(a) In the same manner as in Reference Example 3, a carrier resin combined with Fmoc-Tyr(t-Bu) was condensed in order with N-protected amino acids and the crude peptide Fmoc-Trp-Phe-Phe-Asn-Tyr-Tyr-OH SEQ ID NO:78 was cleaved from the carrier resin. In 0.5 ml of dry DMF were dissolved 12.75 mg of the obtained peptide and 10.4 mg of PyBOP. 0.5 ml of a DMF solution containing 4.4 µl of NMM and 0.5 ml of a DMF solution containing 3.1 mg of HOBt were each added thereto, and the mixture was stirred at room temperature for 5 minutes. To this mixture was added 0.5 ml of a DMF solution containing 3.3 mg of H-Trp-OBzl.HCl containing 1.1 μl of NMM, and the mixture was stirred at room temperature for 2 hours. The reaction solution was concentrated to 0.5 ml, and the white precipitate produced by addition of ether was filtered off an dried to obtain 9 mg of Fmoc-Trp-Phe-Phe-Asn-Tyr-Tyr-Trp-OBzl, SEQ ID NO:79.

(b) 9 mg of the protected peptide obtained in (a) was dissolved in 300 μl of DMF containing 20% piperidine, and the solution was allowed to stand at room temperature for 15 minutes. The white precipitate obtained by addition of ether was filtered off and dried to obtain 6.6 mg of H-Trp-Phe-Phe-Asn-Tyr-Tyr-Trp-OBzl, SEQ ID NO:79.

MS analysis [FABMS]: 1216 (M+H)

(c) In 0.5 ml of DMF were dissolved 3.4 mg of Fmoc-Asp(Ot-Bu)-OH and 8.4 mg of PyBOP, 2.7 μl of NMM and 0.5 ml of a DMF containing 3.1 mg of HOBt were each added. The mixture was then stirred at room temperature for 5 minutes. To the solution was added 1 ml of a DMF containing 6.6 mg of the peptide obtained in (b), and the mixture was stirred at room temperature for 2 hours. The product was purified by reverse phase HPLC according to the same method as used in Example 17, to obtain 3.6 mg of Fmoc-Asp(Ot-Bu)-Trp-Phe-Phe-Asn-Tyr-Tyr-Trp-OBzl, SEQ ID NO:77.

MS analysis [FABMS]: 1610 (M+H)

(d) 3.6 mg of the protected peptide obtained in (c) was treated in the same manner as in (b) to obtain 2 mg of the captioned compound in Step 1.

MS analysis [FABMS]: 1386 (M+H)

Step 2: H-Gly-Asn-Trp-His-Gly-Thr-Ala-Ala-Asp-Trp-Phe-Phe-Asn-Tyr-Tyr-Trp-OBzl SEQ ID NO:80

4.2 mg of Compound (c) obtained in Reference Example 3 was dissolved in 56 μl of DMF. To the solution were added 8.1 μl of a DMF containing 0.2M PyBOP, 8.1 μl of a DMF containing 0.2M HOBt and 15 μl of a DMF containing 2% NMM. The mixture was then stirred at 0° C. for 30 minutes. To the resulting mixture was added 0.1 ml of a DMF containing 0.27 μmol of H-Asp(Ot-Bu)-Trp-Phe-Phe-Asn-Tyr-Tyr-Trp-OBzl, SEQ ID NO:77, obtained in Step 1 above. The mixture was stirred at 4° C. for 24 hours, and at room temperature for 6 hours. The solvent was evaporated under reduced pressure, the residue was again dissolved in DMF, and the product was purified by reverse phase HPLC according to the same method as used in Example 15, to obtain 0.18 mg of the captioned compound, Fmoc-Gly-Asn-Trp-His-Gly-Thr-Ala-Ala-Asp(Ot-Bu)-Trp-Phe-Phe-Asn-Tyr-Tyr-Trp-OBzl, SEQ ID NO:80.

(b) To 180 μg of the protected peptide obtained in was added 20 μl of 98% formic acid, and the mixture was allowed to stand at room temperature for 2 hours. Ether was added to obtain a precipitate. The precipitate was filtered and dried, and 20 μl of DMF containing 20% piperidine was added. The mixture was then allowed to stand at room temperature for 15 minutes. Ether was added to obtain a precipitate. The precipitate was filtered and dried to obtain 140 μg of the captioned compound.

MS analysis [FABMS]: 2126 (M+H)

Step 3: Compound (I-36)

(a) 500 μl of a DMF solution containing 600 μg of the peptide obtained in Step 2 was cooled to 0° C., and 0.2 μl of DEPC and 0.4 μl of TEA were added. The mixture was then stirred at 4° C. for 3 days. The solvent was evaporated under reduced pressure and the resulting products were purified by reverse phase HPLC according to the same method as used in Step 2 (a), to obtain 420 μg of a benzyl ester of Compound (I-36).

MS analysis [FABMS]: 2108 (M+H)

(b) 150 μg of the Compound obtained in (a) was dissolved in 50 μl of DMF, 50 μl of an ammonium formate-saturated methanol and about 0.1 mg of 10% Pd/C were each added. The mixture was then stirred at room temperature for 1.5 hours. The reactants were subjected to centrifugation to obtain a supernatant. The supernatant was then purified by reverse phase HPLC according to the same method as used in (a), to obtain 52 μl of Compound (I-36).

MS analysis [FABMS]: 2016 (M+H)

Amino acid analysis: Gly 2.1 (2), Asx 2.7 (3), His 1.0 (1), Thr 1.1 (1), Ala 2.0 (2), Phe 2.3 (2), Tyr 2.4 (2), (no analysis of Trp)

EXAMPLE 37

Synthesis of Compound (I-37): H-Gly-Asn-Trp-His-Gly-Thr-Ala-Pro-Asp-Trp-Val-Tyr-Tyr-Ala-His-Leu-Asp-Ile-Ile-Trp-OH SEQ ID NO:54

In the same manner as Reference Example 3, 30 mg of a carrier resin combined with 15.6 μmol of Fmoc-Trp was condensed in order with Fmoc-Ile-OH, Fmoc-Ile-OH, Fmoc-Asp(OtBu)-OH, Fmoc-Leu-OH, Fmoc-His (Trt)-OH, Fmoc-Ala-OH,Fmoc-Tyr (t-Bu)-OH, Fmoc-Tyr (t-Bu)-OH, Fmoc-Val-OH, Fmoc-Trp-OH, Fmoc -Asp (Ot-Bu)-OH, Fmoc-Pro-OH, Fmoc -Ala-OH, Fmoc-Thr (t-Bu)-OH, Fmoc-Gly-OH, Fmoc-His (Trt)-OH, Fmoc-Tr p-OH, Fmoc-Asn (Trt)-OH, and Fmoc-Gly-OH as the N-protected amino acids. The process differed from that of Reference Example 3 only in the final step, and the piperidine treatment in (b) was also effected. The peptide was cleaved from the resin in the same manner as in Reference Example 3, to obtain 63.5 mg of the crude product. 1.7 mg of the crude peptide was purified by reverse phase HPLC according to the same method as used in Example 3 and then lyophilized, to obtain 0.44 mg of the purified peptide.

MS analysis [FABMS]: 2415 (M+H)

Amino acid analysis: Gly 2.3 (2), Ala 2.0 (2), Asx 2.6 (3), His 2.0 (2), Ile 1.6 (2), Leu 0.9 (1), Pro 1.1 (1), Thr 1.1 (1), Tyr 1.6 (2), Val 0.7 (1), (no analysis of Trp)

EXAMPLE 38

Synthesis of Compound (I-38): H-Gly-Asn-Trp-His-Gly-Thr-Ala-Pro-AsD-Trp-Leu-Tyr-Phe-Ala-His-Gln-Asp-Val-Ile-Trp-OH SEQ ID NO:55

In the same manner as Reference Example 3, 30 mg of a carrier resin combined with 15.6 μmol of Fmoc-Trp was condensed in order with Fmoc-Ile-OH, Fmoc-Val-OH-Fmoc-Asp (Ot-Bu)-OH, Fmoc-Gln (Trt)-OH, Fmoc-His (Trt)-OH, Fmoc-Ala-OH, Fmoc-Phe-OH, Fmoc-Tyr (t-Bu) -OH, Fmoc-Leu-OH, Fmoc-Trp-OH, Fmoc-Asp (Ot-Bu)-OH, Fmoc-Pro-OH, Fmoc-Ala-OH, Fmoc-Thr (t-Bu)-OH, Fmoc-Gly-OH, Fmoc-His (Trt)-OH, Fmoc-Trp-OH, Fmoc-Asn (Trt)-OH and Fmoc-Gly-OH in order as the N-protected amino acids. The process differed from Reference Example 3 only in the final step, and piperidine treatment in (b) was effected. The peptide was cleaved from the resin in the same manner as in Reference Example 3, to obtain 56.0 mg of the crude product. 2.5 mg of the crude peptide was purified by reverse phase HPLC according to the same method as used in Example 3 and the lyophilized, to obtain 0.42 mg of the purified peptide.

MS analysis [FABMS]: 2414 (M+H)

Amino acid analysis: Gly 2.2 (2), Ala 2.0 (2), Asx 2.7 (3), His 2.0 (2), Ile 0.6 (1), Leu 1.1 (1), Pro 1.1 (1), Thr 1.0 (1), Tyr 1.0 (1), Val 0.6 (1), Glx 1.2 (1), Phe 1.1 (1), (no analysis of Trp)

EXAMPLE 39

Synthesis of Compound (I-39):

SEQ ID NO:56

Gly—Asn—Trp—His—Gly—Thr—Ala—Pro—Asp—Trp—Phe—Phe—Asn—Tyr—Tyr—Asn—Ile—Ile—Trp—OH

Step 1: H-Asn-Ile-Ile-Trp-OBzl SEQ ID NO:57

In the same manner as in Reference Example 3, a carrier resin combined with Fmoc-Ile was condensed with N-protected amino acids, Fmoc-Ile and Fmoc-Asn(Trt)-OH in order to synthesize a protected peptide, and the crude peptide Fmoc-Asn-Ile-Ile-OH was cleaved from the carrier resin. Of the obtained crude peptide, 5.8 mg was dissolved in 1 ml of DMF, 10.4 mg of PyBOP, 2.7 mg of HOBt and 4.4 µl of NMM were added. The solution was then stirred at room temperature for 5 minutes. To the reaction mixture was added 1 ml of a DMF containing 3.3 mg of H-Trp-OBzl.HCl, and stirred at room temperature for 3 hours. The solvent was evaporated under reduced pressure, and the residue was purified by reverse phase HPLC according to the same method as used in Step 1 of Example 36 to obtain 5.4 mg of the Fmoc derivative of the captioned compound in Step 1. The compound was dissolved in 1 ml of DMF containing 20% piperidine, and the solution was allowed to stand at room temperature for 10 minutes. The white precipitate produced by addition of ether was purified by reverse phase HPLC to obtain 5 mg of the captioned Compound in Step 1.

Step 2: Compound (I-39)

In the same manner as in Example 21, 0.19 mg of Compound (I-17) was condensed with 0.1 mg of H-Asn-Ile-Ile-Trp-OBzl, SEQ ID NO:81, to obtain a benzyl ester, and debenzylation was effected to obtain 10 µg of the captioned compound.

MS analysis [FABMS]: 2385 (M+H)

Amino acid analysis: Gly 2.2 (2), Asx 3.3 (4), His 0.9 (1), Thr 0.9 (1), Ala 1.0 (1), Pro 1.0 (1), Phe 1.8 (2), Tyr 1.7 (2), Ile 1.4 (2), (no analysis of Trp)

EXAMPLE 40

Synthesis of Compound (I-40):

SEQ ID NO:57

Gly—Asn—Trp—His—Gly—Thr—Ala—Pro—Asp—Trp—Phe—Phe—Asn—Tyr—Tyr—Ala—His—Leu—Asp—Ile—Ile—Trp—OH

In the same manner as in Example 21, 0.19 mg of Compound (I-17) obtained in Example 17 was condensed with 0.1 mg of H-Ala-His-Leu-Asp(OBzl)-Ile-Ile-Trp-OBzl, SEQ ID NO:82, obtained in Step 1 of Example 35 to obtain a benzyl ester of Compound (I-40). The resulting product was debenzylated according to the same method as used in Example 18 to obtain 9.5 µg of the captioned compound.

MS analysis [FABMS]: 2708 (M+H)

Amino acid analysis: Gly 2.3 (2), Asx 3.4 (4), His 1.9 (2), Thr 1.1 (1), Ala 2.0 (2), Pro 1.2 (1), Phe 1.8 (2), Tyr 1.8 (2), Ile 2.5 (2), Leu 1.0 (1), (no analysis of Trp)

EXAMPLE 41

Synthesis of Compound (I-41):

SEQ ID NO:58

Gly—Asn—Trp—His—Gly—Thr—Ala—Pro—Asp—Trp—Val—Tyr—Phe—Ala—His—Leu—Asp—Ile—Ile—Trp—OH

Step 1: Fmoc-Gly-Asp (OBzl)-Trp-His-Gly-Thr-Ala-OH SEQ ID NO:83

In the same manner as Reference Example 3, 100 mg of a carrier resin combined with 60 µmol of Fmoc-Ala was condensed with Fmoc-Thr(t-Bu)-OH, Fmoc-Gly-OH, Fmoc-His(Trt)-OH, Fmoc-Trp-OH, Fmoc-Asp(OBzl)-OH and Fmoc-Gly-OH in order as the N-protected amino acids. The peptide was cleaved from the resin and purified by HPLC in the same manner as in Example 15, to obtain 40.5 mg of the captioned compound.

MS analysis [FABMS]: 1056 (M+H)

Amino acid analysis: Asx 0.6 (1), Gly 1.6 (2), His 1.0 (1), Thr 0.9 (1), Ala 1.0 (1), (no analysis of Trp)

Step 2: H-Gly-Asp (OBzl)-Trp-His-Gly-Thr-Ala-Pro-Asp-Trp-OBzl (NO$_2$), SEQ ID NO:84

(a) H-pro-Asp(Ot-Bu)-Trp-OBzl (NO$_2$)

In 5 mg of DMP was dissolved 0.33 g of t-Boc-Trp(CHO)-OH, 0.17 g of sodium hydrogen carbonate was added. The solution was then stirred. To the mixture was added 1.08 g (5 mmol) of p-nitrobenzyl bromide, and stirring was effected at room temperature for 24 hours. Water and ethyl acetate were added to the reaction solution. The mixture was shaken, and the organic layer was recovered and the solvent was evaporated. The residue was purified with a silica gel column (manufactured by Merck Co., Kieselgel 60, 50 g, elution with hexane:ethyl acetate=6:4), to obtain 0.2 g of t-Boc-Trp(CHO)-OBzl (NO$_2$). The peptide was dissolved in 5 ml of DMF, 0.5 ml of piperidine was added thereto, and the mixture was stirred at 0° C. for 1.5 hours. The solvent was evaporated under reduced pressure, 0.5 ml of 98% formic acid was added thereto, and the mixture was stirred at room temperature for 4 hours. About 30 ml of ether was added to obtain a precipitate. The precipitate was filtered and dried to obtain 0.16 g of H-Trp-OBzl (NO$_2$).

41 mg of Fmoc-Asp(Ot-Bu)-OH was dissolved in 2 ml of methylene chloride, and the solution was cooled to 0° C. 78 mg of PyBOP, 20 mg of HOBt and 22 µl of NMM were added thereto in order and stirring was effected for 5 minutes, at 0° C. 2 ml of the methylene chloride solution containing 34 mg of H-Trp-OBzl (NO$_2$) as obtained above was cooled to 0° C. and then added to the resulting reaction solution. Stirring was effected at 4° C. for 4 hours and at room temperature for 1 hour, the solvent was evaporated under reduced pressure, and the residue was purified with a silica gel column (manufactured by Merck Co., Kieselgel 60, 50 g, elution with chloroform:methanol=25:1), to obtain 53 mg of Fmoc-Asp(Ot-Bu)-Trp-OBzl(NO$_2$). The obtained product was dissolved in 100 µl of DMF, 25 µl of piperidine was added. The mixture was then allowed to stand at room temperature for 10 minutes, and purified with a silica gel column (manufactured by Merck Co., Kieselgel 60, 50 g, elution with hexane:ethyl acetate=2:1), to obtain 1 mg of H-Asp(Ot-Bu)-Trp-OBzl (NO$_2$).

In 0.5 ml of DMF was dissolved 3.4 mg of Fmoc-Pro-OH, 5.2 mg of PyBOP, 1.4 mg of HOBt and 1.7 µl of NMM were added in order to the solution. The mixture was then stirred at room temperature for 10 minutes. To the resulting reaction solution was added 0.5 ml of a DMF containing 1 mg of H-Asp(Ot-Bu)-Trp-OBzl (NO$_2$) obtained in Step 2, and stirring was effected at room temperature for 1.5 hours. The reaction solution was then concentrated to about 0.2 ml, and the residue was purified by reverse phase HPLC according to the same method as used in Example 17, to obtain 1.5 mg of Fmoc-Pro-Asp(Ot-Bu)-Trp-OBzl (NO$_2$).

The peptide was dissolved in 160 µl of DMF, 40 µl of piperidine was added to the solution. The mixture was then allowed to stand at room temperature for 12 minutes, and the solvent was evaporated under reduced pressure. The residue was purified by HPLC in the same manner as above, to obtain 1.4 mg of H-Pro-Asp(Ot-Bu)-Trp-OBzl (NO$_2$).

MS analysis [FABMS]: 608 (M+H)

2.4 mg of the peptide obtained in Step 1 was dissolved in 0.5 ml of DMF, 4.8 mg of PyBOP, 1.2 mg of HOBt and 1.2 µl of NMM were added thereto, and the mixture was stirred at room temperature for 15 minutes and then cooled to 0° C. To the reaction mixture was added 0.5 ml of a DMF containing 0.7 mg of H-Pro-Asp(Ot-Bu)-Trp-OBzl (NO$_2$) obtained above. The mixture was stirred at 4° C. for 18 hours and at room temperature for 3 hours. The solvent was evaporated under reduced pressure and the residue was purified by reverse phase HPLC in the same manner as above. The resulting compound was dissolved in 98% formic acid and stirred at room temperature for 2 hours, and ether was added to the reaction mixture to obtain a precipitate. The precipitate was dissolved in 20% piperidine/DMF and stirred at room temperature for 15 minutes, followed by precipitation by addition of ether, to obtain 400 µg of H-Gly-Asp(OBzl)-Trp-His-Gly-Thr-Ala-Pro-Asp-Trp-OBzl (NO$_2$), SEQ ID NO:84.

HOBt and 152 µg of NMM at 0° C., and the mixture was stirred at 0° C. for 1 hour and at room temperature for 3.5 hours. The solvent was evaporated under reduced pressure, and the residue was purified by reverse phase HPLC in the same manner as above to obtain 40 µg of a 4-nitrobenzyl ester of the captioned compound. The obtained product was then dissolved in 50 µl of 90% acetic acid and cooled to 0° C. Approximately 0.1 mg of zinc powder was added thereto and the mixture was stirred at 0° C. for 30 minutes. The zinc powder was removed by centrifugation, and the supernatant was purified by reverse phase HPLC according to the same method as used in Example 15, to obtain 27 µg of the captioned compound.

Step 4: Compound (I-41)

25 µg of the compound obtained in Step 3 was dissolved in 23 µl of DMF and cooled to 0° C., 0.2M DMF containing 68 µg of PyBOP, 0.2M DMF containing 18 µg of HOBt and 0.2M DMF containing 21 µg of NMM were each added, and the mixture was allowed to stand at 0° C. for 10 minutes. To the reaction solution was added 27 µl of a DMF containing 44 µg of H-Val-Tyr-Phe-Ala-His-Leu-Asp(OBzl)-Ile-Ile-Trp-OBzl obtained in Step 1 of Example 20, and the mixture was stirred at 4° C. for 24 hours. The solvent was evaporated under reduced pressure, and the residue was purified by reverse phase HPLC in the same manner as in Step 3, to obtain 15 µg of Compound (I-41) whose side chains and C-terminal were protected. 13 µg of the compound was dissolved in 10 µl of DMF, 10 µl of a methanol saturated with ammonium formate and about 0.1 mg of 10% Pd/C were added. The mixture was then stirred at room temperature for 1.5 hours. The Pd/C was removed by centrifugation, and the supernatant was purified by reverse phase HPLC in the same manner as above, to obtain 2 µg of Compound (I-41).

MS analysis [FABMS]: 2383 (M+H)

Amino acid analysis: Asx2.1 (3), Gly 2.3 (2), His 1.4 (2), Thr 1.1 (1), Ala 2.0 (2), Pro 1.0 (1), Tyr 0.9 (1), Val 1.3 (1), Ile 2.5 (2), Leu 1.3 (1), Phe 0.9 (1), (no analysis of Trp)

EXAMPLE 42

Synthesis of Compound (I-42):

SEQ ID NO:85

Step 3: ⌐Gly—Asp(OBzl)—Trp—His—Gly—Thr—Ala—Pro—Asp—
Trp—OH

To 100 µl of a DMF containing 200 µg of the peptide obtained in Step 2 were added 468 µg of PyBOP, 122 µg of

SEQ ID NO:59

⌐Gly—Asn—Trp—Lys—Gly—Thr—Ala—Pro—Asp—Trp—Val—Tyr—Phe—Ala—

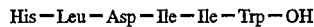

Step 1: Fmoc-Gly-Asn-Trp-Lys (Z)-Gly-Thr-Ala-OH SEQ ID NO:86

In the same manner as Reference Example 3, 100 mg of a carrier resin combined with 60 μmol of Fmoc-Ala was condensed in order with Fmoc-Thr(t-Bu)-OH, Fmoc-Gly-OH, Fmoc-Lys(Z)-OH, Fmoc-Trp-OH, Fmoc-Asn(Trt)-OH and Fmoc-Gly-OH as the N-protected amino acids. The resulting peptide was cleaved from the resin and purified by HPLC in the same manner as in Example 17, to obtain 9.9 mg of the captioned compound.

MS analysis [FABMS]: 1090 (M+H)

Amino acid analysis: Asx 0.6 (1), Gly 1.5 (2), Thr 0.8 (1), Ala 1.0 (1), Lys 0.9 (1), (no analysis of Trp)

Step 2: H-Gly-Asn-Trp-Lys (Z)-Gly-Thr-Ala-Pro-Asp-Trp-OBzl (NO₂) SEQ ID NO:87

2.5 mg of the peptide obtained in Step 1 was dissolved in 0.5 ml of DMF, 2.4 mg of PyBOP, 0.6 mg of HOBt and 0.8 μl of NMM were added. The mixture was then stirred at room temperature for 15 minutes and then cooled to 0° C. To the reaction mixture was added 0.5 ml of a DMF containing 0.7 mg of H-Pro-Asp(Ot-Bu)-Trp-OBzl (NO₂) obtained in Example 41, and the mixture was stirred at 4° C. for 6 hours. The solvent was evaporated under reduced pressure and the residue was purified by reverse phase HPLC in the same manner as above. The resulting compound was then treated with 70 μl of 98% formic acid and stirred at room temperature for 2 hours, and then mixed with a mixture of 10 μl of 20% piperidine and 40 μl of DMF and stirred at room temperature for 15 minutes. Crystallization was then effected with 3 ml of ether, followed by washing with ether and drying under reduced pressure, to obtain 420 μg of the compound captioned in Step 2.

SEQ ID NO:88

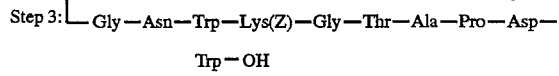

To 100 μl of a DMF containing 200 μg of the peptide obtained in Step 2 were added 468 μg of PyBOP, 122 μg of HOBt and 152 μg of NMM at 0° C., and the mixture was stirred at 0° C. for 1 hour and at room temperature for 3.5 hours. The solvent was evaporated under reduced pressure, and the residue was purified by reverse phase HPLC in the same manner as above to obtain 43 μg of a 4-nitrobenzyl ester of the captioned compound. The obtained product was then dissolved in 50 μl of 90% acetic acid and cooled to 0° C. Approximately 0.1 mg of zinc powder was added, and the mixture was then stirred at 0° C. for 30 minutes. The zinc powder was removed by centrifugation, and the supernatant was purified by reverse phase HPLC according to the same method as used in Example 15, to obtain 59 μg of the compound captioned in Step 3.

Step 4: Compound (I-42)

The Compound obtained in Step 3, 59 μg was dissolved in 32 μl of DMF and cooled to 0° C. To the mixture were added 156 μg of PyBOP, 41 μg of HOBt and 51 μg of NMM, each of which was prepared with 0.2 ml of a DMF solution, and the mixture was allowed to stand at 0° C. for 10 minutes. To the resulting reaction mixture was added 68 μl of a DMF containing 109 μg of H-Val-Tyr-Phe-Ala-His-Leu-Asp (OBzl)-Ile-Ile-Trp-OBzl, SEQ ID NO:71, obtained in Step 1 of Example 20, and the mixture was stirred at 4° C. for 13 hours. The solvent was evaporated under reduced pressure, and the residue was purified by reverse phase HPLC in the same manner as in Step 3, to obtain 31 μg of Compound (I-42) whose side chains and C-terminal were protected.

28 μg of the compound was dissolved in 15 μl of DMF, 15 μl of methanol saturated with ammonium formate and about 0.1 mg of 10% Pd/C were added thereto. The mixture was stirred at room temperature for 2 hours. The Pd/C was removed by centrifugation, and the supernatant was purified by reverse phase HPLC in the same manner as above, to obtain 10.6 μg of Compound (I-42).

MS analysis [FABMS]: 2373 (M+H)

Amino acid analysis: Asx 2.8 (3), Gly 2.6 (2), His 1.0 (1), Thr 0.9 (1), Ala 2.0 (2), Pro 1.2 (1), Tyr 1.0 (1), Val 1.1 (1), Ile 2.4 (2), Phe 1.0 (1), Lys 0.9 (1), (no analysis of Trp)

EXAMPLE 43

Synthesis of Compound (I-43): H-Gly-Asp-Trp-His-Gly-Thr-Ala-Pro-Asp-Trp-Val-Tyr-Phe-Ala-His-Leu-Asp-Ile-Ile-Trp-OH SEQ ID NO:60

In the same manner as Reference Example 3, 20 mg of a carrier resin combined with 10.4/ μmol of Fmoc-Trp was condensed with Fmoc-Ile-OH, Fmoc-Ile-OH, Fmoc-Asp (Ot-Bu)-OH, Fmoc-Leu-OH, Fmoc-His (Trt)-OH, Fmoc-Ala-OH, Fmoc-Phe-OH, Fmoc-Tyr (t-Bu)-OH, Fmoc-Val-OH, Fmoc-Trp-OH, Fmoc-Asp (Ot-Bu)-OH, Fmoc-Pro-OH, Fmoc-Ala-OH, Fmoc-Thr (t-Bu)-OH, Fmoc-Gly-OH, Fmoc-His (Trt)-OH, Fmoc-Trp-OH, Fmoc-Asp (Ot-Bu)-OH, and Fmoc-Gly-OH in order as the N-protected amino acids. The process differed from that of Reference Example 3 only in the final step, and piperidine treatment in (b) was effected. The peptide was cleaved form the resin in the same manner as in Reference Example 3, to obtain 19.2 mg of a crude peptide. 6.2 mg of the crude peptide was purified by HPLC according to the same method as in Example 17 and then lyophilized, to obtain 1.24 mg of the purified product.

MS analysis [FABMS]: 2400 (M+H)

Amino acid analysis: Gly 2.1 (2), Ala 2.0 (2), Asx 2.1 (3), His 1.4 (2), Ile 2.5 (2), Leu 1.3 (1), Pro 1.0 (1), Thr 1.1 (1), Phe 0.9 (1), Tyr 0.9 (1), Val 1.3 (1), (no analysis of Trp)

EXAMPLE 44

Synthesis of Compound (I-44): H-Gly-Asn-Trp-Lys-Gly-Thr-Ala-Pro-Asp-Trp-Val-Tyr-Phe-Ala-His-Leu-Asp-Ile-Ile-Trp-OH SEQ ID NO:61

In the same manner as Reference Example 3, 20 mg of a carrier resin combined with 10.4 μmol of Fmoc-Trp was condensed in order with Fmoc-Ile-OH, Fmoc-Ile-OH, Fmoc-Asp (Ot-Bu)-OH, Fmoc-Leu-OH, Fmoc-His (Trt)-OH, Fmoc-Ala-OH, Fmoc-Phe-OH, Fmoc-Tyr (t-Bu)-OH, Fmoc-Val-OH, Fmoc-Trp-OH, Fmoc-Asp (Ot-Bu)-OH, Fmoc-Pro-OH, Fmoc-Ala-OH, Fmoc-Thr (t-Bu)-OH, Fmoc-Gly-OH, Fmoc-Lys (t-Boc)-OH, Fmoc-Trp-OH, Fmoc-Asn (Trt)-OH, and Fmoc-Gly-OH as the N-protected amino acids. The process differed from that of Reference Example 3 only in the final step, and piperidine treatment in (b) was effected. The peptide was cleaved from the resin in the same manner as in Reference Example 3, to obtain 30.0 mg of a crude peptide. 6.9 mg of the crude product was purified by HPLC according to the same method as in Example 17 and then lyophilized, to obtain 1.30 mg of the purified product.

MS analysis [FABMS]: 2390 (M+H)

Amino acid analysis: Gly 2.6 (2), Ala 2.0 (2), Asx 2.8 (3), His 1.0 (1), Ile 2.4 (2), Leu 1.1 (1), Pro 1.2 (1), Thr 0.9 (1), Tyr 1.0 (1), Val 1.1 (1), Phe 1.0 (1), Lys 0.9 (1), (no analysis of Trp)

EXAMPLE 45

Synthesis of Compound (I-45):

SEQ ID NO:62

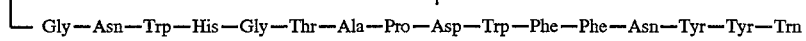

0.1 ml of DMF solution containing 0.84 mg of PyBOP, 0.1 ml of DMF solution containing 0.22 mg of HOBt and 0.1 ml of DMF solution containing 0.3 μl of NMM were added to 0.5 ml of DMF solution containing 1 mg of Compound (I-17) obtained in Example 17 and allowed to stand at 0° C. for 10 minutes. Next, 0.1 ml of DMF solution containing 0.53 mg of H-Trn.HCl and 0.3 μl of NMM was added thereto and stirred for 16 hours at 4° C. 0.1 ml of 2M acetic acid was added thereto, and the crude product was subjected to HPLC purification using a reverse, phase column (CAPCELL PACK C18, 250 mm×30 mm I.D., manufactured by Shiseido). The elution was carried out with a linear concentration gradient pattern using 0 to 90% acetonitrile containing 0.1% TFA, and upon detection at 220 nm, fractions containing the entitled Compound (I-45) were obtained. These fractions were lyophilized to obtain 0.1 mg of Compound (I-45).

MS analysis [FABMS]: 1998 (M+H)

Amino acid analysis: Gly 2.2 (2), Ala 1.0 (1), Asx 2.0 (3), His 1.0 (1), Pro 1.1 (1), Thr 1.1 (1), Tyr 1.9 (2), Phe 1.9 (2), (no analysis of Trp and Trn).

EXAMPLE 46

Synthesis of Compound (I-46)

SEQ ID NO:63

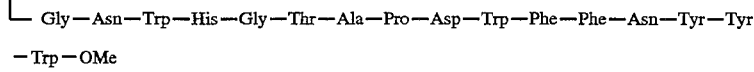

0.1 ml of DMF solution containing 0.84 mg of PyBOP, 0.1 ml of DMF solution containing 0.22 mg of HOBt and 0.1 ml of DMF solution containing 0.3 μl of NMM were added to 0.5 ml of DMF solution containing 1 mg of Compound (I-17) obtained in Example 17 and allowed to stand at 0° C. for 10 minutes. Next, 0.1 ml of DMF solution containing 0.69 mg of H-Trp-OMe.HCl and 0.3 μl of NMM was added thereto and stirred for 6 hours at room temperature. 0.1 ml of 2M acetic acid was added thereto, and the crude product was partitioned and purified in the same manner as in Example 45 to obtain 0.03 mg of Compound (I-46).

MS analysis [FABMS]: 2056 (M+H)

Amino acid analysis: Gly 2.1 (2), Ala 1.0 (1), Asx 2.1 (3), His 1.0 (1), Pro 1.0 (1), Thr 1.0 (1), Tyr 1.8 (2), Phe 1.8 (2), (no analysis of Trp).

EXAMPLE 47

Synthesis of Compound (I-47):

SEQ ID NO:64

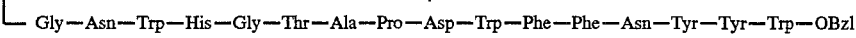

10 μl of DMF solution containing 84 μg of PyBOP, 10 μl of DMF solution containing 22 μg of HOBt and 10 μl of DMF solution containing 0.03 μl of NMM were added to 55 μl of DMF solution containing 100 μg of Compound (I-17) obtained in Example 17 and allowed to stand at 0° C. for 10 minutes. Next, 10 μl of DMF solution containing 89 μg of H-Trp-OBzl.HCl and 0.03 μl of NMM were added thereto and stirred for 54 hours at 4° C. 10 μl of 2M acetic acid were added thereto, and the crude product was purified in the same manner as in Example 45 to obtain 50 μg of Compound (I-47).

MS analysis [FABMS]: 2132 (M+H)

Amino acid analysis: Gly 2.2 (2), Ala 1.0 (1), Asx 2.2 (3), His 1.1 (1), Pro 1.2 (1), Thr 1.0 (1), Tyr 1.9 (2), Phe 1.9 (2), (no analysis of Trp).

EXAMPLE 48

Synthesis of Compound (I-48):

SEQ ID NO:65

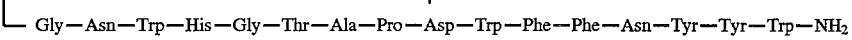

10 μl of DMF solution containing 84 μg of PyBOP, 10 μl of DMF solution containing 22 μg of HOBt and 10 μl of DMF solution containing 0.03 μl of NMM were added to 55 μl of DMF solution containing 100 μg of Compound (I-17) obtained in Example 17 and allowed to stand at 0° C. for 10 minutes. Next, 10 μl of DMF solution containing 32 μg of H-Trp-NH₂·HCl and 0.03 μl of NMM was added thereto and stirred for 54 hours at 4° C. 10 μl of 2M acetic acid was added thereto, and the crude product was purified in the same manner as in Example 45 to obtain 62 μg of Compound (I-48).

MS analysis [FABMS]: 2041 (M+H)

Amino acid analysis: Gly 2.2 (2), Ala 1.0 (1), Asx 2.1 (3), His 1.0 (1), Pro 1.1 (1), Thr 1.0 (1), Tyr 1.9 (2), Phe 1.9 (2), (no analysis of Trp).

EXAMPLE 49

Synthesis of Compound (I-49):

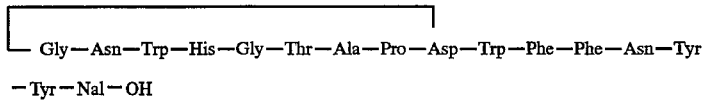

Step 1: H-Nal-OBzl(NO₂)

43.75 mg of Fmoc-Nal-OH were dissolved in 1 ml of DMF, and 16.8 mg of sodium hydrogencarbonate and 108 mg of 4-nitrobenzyl bromide were added thereto and stirred for 17 hours at room temperature. 30 ml of ethyl acetate and 70 ml of water were added thereto and shaken, and the ethyl acetate layer was recovered and dried on sodium sulfate. The dried product was filtered, and the solvent was removed from the resulting filtrate by distillation. The residue was subjected to silica gel column chromatography (Kieselgel 60, manufactured by Merck Co., elution with ethyl acetate/ hexane) to obtain Fmoc-Nal-OBzl(NO₂) as a white powder. The thus-obtained powder was dissolved in DMF containing 20% piperidine and allowed to stand at room temperature for 20 minutes. The solvent was removed by evaporation under reduced pressure, and the residue was partitioned and purified in the same manner as in Example 45 to obtain 33.6 mg of H-Nal-OBzl(NO₂).

MS analysis [FABMS]: 351 (M+N)

Step 2: Compound (5)

10 μl of DMF solution containing 84 μg of PyBOP, 10 μl of DMF solution containing 22 μg of HOBt and 10 μl of DMF solution containing 0.03 μl of NMM were added to 55 μl of DMF solution containing 100 μg of Compound (I-17) obtained in Example 17 and allowed to stand at 0° C. for 10 minutes. Next, 10 μl of DMF solution containing 125 μg of H-Nal-OBzl(NO₂) obtained in the previous Step 1 and 0.03 μl of NMM were added thereto and stirred for 54 hours at 4° C. 100 μl of 90% acetic acid was added thereto, then about 5 mg of zinc powder was added thereto under cooling with ice, and the mixture were left as they were for 10 minutes. Then, the temperature of the mixture was brought back to room temperature and then stirred for one hour. After centrifugation, the resulting supernatant was purified in the same manner as in Example 45 to obtain 14 μg of Compound (I-49).

MS analysis [FABMS]: 2053 (M+H)

Amino acid analysis: Gly 2.3 (2), Ala 1.0 (1), Asx 2.0 (3), His 1.0 (1), Pro 1.1 (1), Thr 1.0 (1), Tyr 1.9 (2), Phe 1.9 (2), (no analysis of Trp and Nal).

Reference Example 1

Synthesis of Compound (a): Fmoc-Gly-Asn-Trp-His-Gly-Thr-Ala-Pro-OH SEQ ID NO:89

In the same method as in Example 4, a carrier resin combined with t-Boc-Pro was condensed in order with t-Boc-Ala-OH, t-Boc-Ala-OH, t-Boc-Thr (Bzl)-OH, t-Boc-Gly-OH, t-Boc-His (Bom)-OH, t-Boc-Trp (CHO)-OH, t-Boc-Asn-OH and Fmoc-Gly-OH as the protected amino acids, to obtain 1.2 g of the carrier resin combined with a protected peptide. 1.2 g of the carrier resin was treated with hydrogen fluoride in the same manner as in Example 4 to cleave the synthesized peptide from the resin, and the peptide was dissolved in 2M acetic acid and lyophilized to obtain 464.0 mg of a crude product. The crude product was purified by HPLC in the same manner as in Example 4, to obtain 131.9 mg of Compound (a).

MS analysis [FABMS]: 1061 (M+H)

Amino acid analysis; Asx 0.7 (1), Gly 9.1 (2), His 1.0 (1), Thr 1.0 (1), Pro 1.1 (1), Ala 1.1 (1), (no analysis of Trp).

Reference Example 2

Synthesis of Compound (b): H-Val-Tyr-Phe-Ser-His-Leu-Asp-Ile-Ile-Trp-OH SEQ ID NO:90

In the same method as in Example 4, a carrier resin combined with t-Boc-Trp (CHO) was condensed with t-Boc-Ile-OH, t-Boc-Ile-OH, t-Boc-Asp (OBzl)-OH, t-Boc-Leu-OH, t-Boc-His (Bom)-OH, t-Boc-Ser-OH, t-Boc-Phe-OH, t-Boc-Tyr (Br-Z)-OH and t-Boc-Val-OH in order as the N-protected amino acids, to obtain 1.5 g of the carrier resin with a protected peptide. 0.8 g of the peptide was cleaved from the resin by treatment with hydrogen fluoride, and the peptide was dissolved in 2M acetic acid and lyophilized to obtain 243.3 mg of a crude product. 101 mg of the crude product, was purified by HPLC in the same manner as in Example 4, to obtain 7.0 mg of Compound (b).

MS analysis [FABMS]: 1293 (M+H)

Amino acid analysis: Asx 1.1 (1), Ser 1.1 (1), His 1.2 (1), Tyr 1.0 (1), Val 1.0 (1), Ile 1.5 (2), Leu 1.2 (1), Phe 1.1 (1)

Reference Example 3

Synthesis of Compound (c) : Fmoc-Gly-Asn-Trp-His-Gly-Thr-Ala-Ala-OH SEQ ID NO:91

Using 50 mg of a carrier resin combined with 30 μmol of Fmoc-Ala as the starting material was placed in an automatic synthesizer reactor, the automatic peptide synthesis was effected following the synthesis program of Shimadzu Seisakusho, in the following manner.

(a) The carrier resin was washed with DMF for 3 minutes, and the solution was drawn off.

(b) A DMF solution containing 30% piperidine was added thereto, and the mixture was stirred for 4 minutes. The solution was drawn off, and the procedure was repeated one more time.

(c) The carrier resin was washed with DMF for 1 minute, the solution was drawn off, and the procedure was repeated 5 times.

In this manner, an Ala-combined carrier resin lacking Fmoc group was obtained.

(d) 1.05 ml of a DMF containing 300 μmol of Fmoc-Ala-OH, 300 μmol of PyBOP, 300 μmol of HOBt and 450

μmol of NMM were added, the mixture was stirred for 3 minutes, and the resulting solution was added to the resin. The mixture Was stirred for 30 minutes and the solution was drawn off.

(e) The carrier resin was washed with DMF for 1 minute, and the washing was repeated 5 times. Fmoc-Ala-Ala was thus synthesized on the carrier. Next, washing was effected as in (a)–(c) above, followed by de-protection. A condensation reaction was effected using Fmoc-Thr (t-Bu) in step (d) above, followed by washing as in (e) for synthesis of Fmoc-Thr(t-Bu)-Ala-Ala on the carrier resin. Steps (a)–(e) were then repeated in order to obtain a carrier resin combined with a protected peptide bound thereto. Here, in Step (d), Fmoc-Gly-OH, Fmoc-His(Trt)-OH, Fmoc-Trp-OH, Fmoc-Asn(Trt)-OH and Fmoc-Gly-OH were used in order. Treatment with piperidine in Step (b) was omitted only in the final step of condensation of Gly. The obtained carrier resin was washed with methanol and butyl ether, and then dried under reduced pressure for 3 hours. To the dried product was added 200 μl of a mixture of 90% TFA, 5% thioanisol and 5% 1,2-ethanedithiol containing 2-methylindole at a proportion of 5 mg/ml, the mixture was allowed to stand at room temperature for 2 hours, and the peptide was cleaved from the resin. Next, the resin was filtered off, about 10 mg of ether was added to the filtrate, and 23 mg of the resulting precipitate was filtered off as the crude peptide. This crude product was then purified by HPLC using a reverse phase column (column: Chemco Pack NUCLEOSIL 5C18 250×20 mm I.D., manufactured by Chemco Co.). The elution was effected with a linear concentration gradient pattern 0–90% acetonitrile containing 0.1% TFA, and detection was effected at 220 nm to obtain fractions containing the captioned compound. These fractions were lyophilized to obtain 16 mg of Compound (c).

MS analysis [FABMS]: 1036 (M+H)

Amino acid analysis: Gly 1.9 (2), Asx 0.7 (1), His 1.0 (1), Thr 0.9 (1), Ala 2.0 (2), (no analysis of Trp)

Reference Example 4

Synthesis of Compound (d): Fmoc-Leu-Tyr-Phe-Ala-His-Gln-Asp (OBzl)-Val-Ile-OH SEQ ID NO:92

According to the same method as used in Reference Example 3, 70 mg of a carrier resin combined with 31 μmol of Fmoc-Ile was used, and Fmoc-Val-OH, Fmoc-Asp(OBzl)-OH, Fmoc-Gln(Trt)-OH, Fmoc-His(Trt)-OH, Fmoc-Ala-OH, Fmoc-Phe-OH, Fmoc-Tyr(t-Bu)-OH and Fmoc-Leu-OH were used in order as the N-protected amino acids for synthesis. The cleaving of the peptide from the resin was effected by adding 300 μl of a mixture containing 90% TFA, 5% thioanisol and 5% 1,2-ethanedithiol at room temperature for 2 hours. Of the obtained peptide, 25 mg was purified by HPLC according to the same method as used in Reference Example 3, to obtain 3.6 mg of Compound (d).

MS analysis [FABMS]: 1419 (M+H)

Amino acid analysis: Ala 1.0 (1), Asx 1.0 (1), His 0.9 (1), Glx 1.0 (1), Ile 0.8 (1), Leu 0.8 (1), Phe 0.9 (1), Tyr 1.0 (1), Val 0.7 (1)

Industrial Applicability

According to the present invention, a peptide is provided which possesses endothelin-antagonizing activity.

We claim:

1. A peptide represented by the following formula (I):

SEQ ID NO: 2

$$X^1-Gly-A-Trp-B-Gly-Thr-E-Pro-Asp-Z$$
$$\phantom{X^1-Gly-A-Trp-B-Gly-Thr-E-Pro-}|$$
$$\phantom{X^1-Gly-A-Trp-B-Gly-Thr-E-Pro-}Y^1$$

wherein

A represents Asn or Asp;

B represents His or Lys;

E represents Ala or Ser;

(1) $X^1$ and $Y^1$ are combined together to form a single bond as $X^1$-$Y^1$, or (2) $X^1$ represents hydrogen and $Y^1$ represents hydroxy; and Z represents, in case of (1), Trp-Phe-Phe-Asn-Tyr-Tyr-7Hyt-$Z^1$    SEQ ID NO:4 where $Z^1$ is hydroxy, lower alkoxy, benzyloxy, amino

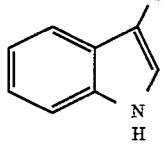,

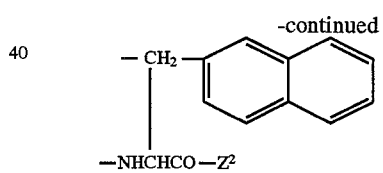

wherein $Z^2$ is OH and 7Hyt represents 7-hydroxytryptophan,

Trp-Val-Tyr-Phe-Ala-His-Leu-Asp-Ile-Ile-Trp-$Z^1$    SEQ ID NO:6 where $Z^1$ is as defined previously,

Trp-Val-Tyr-Tyr-Ala-His-Leu-Asp-Ile-Ile-Trp-$Z^1$    SEQ ID NO:8 where $Z^1$ is as defined previously,

Trp-Leu-Tyr-Phe-Ala-His-Gln-Asp-Val-Ile-Trp-$Z^1$    SEQ ID NO:9 where $Z^1$ is as defined previously,

Trp-Phe-Phe-Asn-Tyr-R-T-$Z^1$    SEQ ID NO:13 where R is Tyr or a covalent bond,
T is Trp,
  Ala,
  Phe,
  Tyr,

Trp-Trp,

Asn-Tyr-Tyr-Trp, SEQ ID NO:14

Trp-Asn-Tyr-Tyr-Trp, SEQ ID NO:15

Trp-Val-Tyr-Phe-Ala-His-Leu-Asp-Ile-Ile-Trp, SEQ ID NO:16 and $Z^1$ is as define previously,
or in case of (2),

Trp-Val-Tyr-Phe-Ala-His-Leu-Asp-Ile-Ile-Trp-$Z^1$ SEQ ID NO:6 where $Z^1$ is as defined previously,

Trp-Val-Tyr-Tyr-Ala-His-Leu-Asp-Ile-Ile-Trp-$Z^1$ SEQ ID NO:8 where $Z^1$ is as defined previously,

Trp-Leu-Tyr-Phe-Ala-His-Gln-Asp-Val-Ile-Trp-$Z^1$ SEQ ID NO:9 where $Z^1$ is as defined previously,
or a pharmaceutically acceptable salt thereof.

2. A peptide which is represented by the following formula (I-1):

SEQ ID NO:18

$$\overline{\phantom{xxxxxxxxxxxxxxxxxxxxxxxxxxxxxxx}}$$
└─ Gly—Asn—Trp—His—Gly—Thr—Ala—Pro—Asp (I-1)

—Trp—Phe—Phe—Asn—Tyr—Tyr—Trp—OH

3. A peptide which is represented by the following formula (I-2):

SEQ ID NO:19

$$\overline{\phantom{xxxxxxxxxxxxxxxxxxxxxxxxxxxxxxx}}$$
└─ Gly—Asn—Trp—His—Gly—Thr—Ala—Pro—Asp (I-2)

—Trp—Phe—Phe—Asn—Tyr—Tyr—7Hyt—OH

4. A peptide which is represented by the following formula (I-3):

SEQ ID NO:20

$$\overline{\phantom{xxxxxxxxxxxxxxxxxxxxxxxxxxxxxxx}}$$
└─ Gly—Asn—Trp—His—Gly—Thr—Ser—Pro—Asp (I-3)

—Trp—Phe—Phe—Asn—Tyr—Tyr—Trp—OH

* * * * *

SEQUENCE LISTING ( 1 ) GENERAL INFORMATION:

( i i i ) NUMBER OF SEQUENCES: 92

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

Xaa  Leu  Xaa  Trp  Xaa  Glu  Ala
    1                      5

( 2 ) INFORMATION FOR SEQ ID NO:2:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:2:

```
Xaa Xaa Trp Xaa Gly Thr Xaa Xaa Xaa
1               5
```

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:3:

```
Trp Asn Tyr Tyr Trp
1               5
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:4:

```
Trp Phe Phe Asn Tyr Tyr Xaa
1               5
```

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:5:

```
Trp Ile Ile Trp
1
```

( 2 ) INFORMATION FOR SEQ ID NO:6:

( i ) SEQUENCE CHARACTERISTICS:
 ( A ) LENGTH: 11 amino acids
 ( B ) TYPE: amino acid
 ( C ) STRANDEDNESS: single
 ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:6:

```
Trp Val Tyr Phe Xaa His Leu Asp Ile Ile Trp
1               5                   10
```

( 2 ) INFORMATION FOR SEQ ID NO:7:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

```
Trp Xaa His Leu Asp Ile Ile Trp
1               5
```

( 2 ) INFORMATION FOR SEQ ID NO:8:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:8:

```
Trp Val Tyr Tyr Xaa His Leu Asp Ile Ile Trp
1               5                   10
```

( 2 ) INFORMATION FOR SEQ ID NO:9:

( i ) SEQUENCE CHARACTERISTICS:
  ( A ) LENGTH: 11 amino acids
  ( B ) TYPE: amino acid
  ( C ) STRANDEDNESS: single
  ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:9:

Trp Leu Tyr Phe Xaa His Gln Asp Val Ile Trp
1               5                   10

( 2 ) INFORMATION FOR SEQ ID NO:10:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:10:

Trp Val Tyr Phe Xaa Phe Phe Asn Tyr Tyr Trp
1               5                   10

( 2 ) INFORMATION FOR SEQ ID NO:11:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:11:

Trp Phe Phe Asn Tyr Tyr Xaa His Leu Asp Ile Ile Trp
1               5                   10

( 2 ) INFORMATION FOR SEQ ID NO:12:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

Trp Phe Phe Asn Tyr Tyr Asn Ile Ile Trp
1               5                   10

( 2 ) INFORMATION FOR SEQ ID NO:13:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:13:

```
Xaa  Phe  Xaa  Xaa  Tyr  Xaa  Xaa
1                   5
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:14:

```
Asn  Tyr  Tyr  Trp
1
```

(2) INFORMATION FOR SEQ ID NO:15:

(i) SEQUENCE CHARACTERISTICS:
        (A) LENGTH: 5 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:15:

```
Trp  Asn  Tyr  Tyr  Trp
1                   5
```

(2) INFORMATION FOR SEQ ID NO:16:

(i) SEQUENCE CHARACTERISTICS:
        (A) LENGTH: 11 amino acids
        (B) TYPE: amino acid
        (C) STRANDEDNESS: single
        (D) TOPOLOGY: linear (i i) MOLECULE TYPE: peptide (i i i) HYPOTHETICAL: NO (i v) ANTI-SENSE: NO (v) FRAGMENT TYPE: N-terminal (x i) SEQUENCE DESCRIPTION: SEQ ID NO:16:

```
Trp  Val  Tyr  Phe  Xaa  His  Leu  Asp  Ile  Ile  Trp
1                   5                        10
```

( 2 ) INFORMATION FOR SEQ ID NO:17:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:17:

Xaa  Phe  Xaa  Xaa  Tyr  Xaa  Xaa
    1                          5

( 2 ) INFORMATION FOR SEQ ID NO:18:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

Gly  Asn  Trp  His  Gly  Thr  Ala  Pro  Asp  Trp  Phe  Phe  Asn  Tyr  Tyr  Trp
    1                    5                              10                      15

( 2 ) INFORMATION FOR SEQ ID NO:19:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

Gly  Asn  Trp  His  Gly  Thr  Ala  Pro  Asp  Trp  Phe  Phe  Asn  Tyr  Tyr  Xaa
    1                    5                              10                      15

( 2 ) INFORMATION FOR SEQ ID NO:20:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO -continued (v) FRAGMENT TYPE: N-terminal (xi) SEQUENCE DESCRIPTION: SEQ ID NO:20:

Gly Asn Trp His Gly Thr Ser Pro Asp Trp Phe Phe Asn Tyr Tyr Trp
1               5                   10                  15

(2) INFORMATION FOR SEQ ID NO:21:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:21:

Gly Asn Trp His Gly Thr Ala Pro Asp Trp Phe Phe Asn Tyr Tyr Trp
1               5                   10                  15

(2) INFORMATION FOR SEQ ID NO:22:

(i) SEQUENCE CHARACTERISTICS:
        (A) LENGTH: 16 amino acids
        (B) TYPE: amino acid
        (C) STRANDEDNESS: single
        (D) TOPOLOGY: circular (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:22:

Gly Asn Trp His Gly Thr Ala Pro Asp Trp Phe Phe Asn Tyr Tyr Trp
1               5                   10                  15

(2) INFORMATION FOR SEQ ID NO:23:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:23:

Cys Asn Trp His Gly Thr Ala Pro Cys Trp Phe Phe Asn Tyr Tyr Trp
1               5                   10                  15

(2) INFORMATION FOR SEQ ID NO:24:

(i) SEQUENCE CHARACTERISTICS:
        (A) LENGTH: 16 amino acids
        (B) TYPE: amino acid (C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:24:

Cys Asn Trp His Gly Thr Ala Pro Cys Trp Phe Phe Asn Tyr Tyr Trp
1               5                   10                  15

(2) INFORMATION FOR SEQ ID NO:25:

(i) SEQUENCE CHARACTERISTICS:
(A) LENGTH: 16 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:25:

Cys Asn Trp His Gly Thr Ala Pro Cys Trp Phe Phe Asn Tyr Tyr Trp
1               5                   10                  15

(2) INFORMATION FOR SEQ ID NO:26:

(i) SEQUENCE CHARACTERISTICS:
(A) LENGTH: 7 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:26:

Trp Phe Phe Asn Tyr Tyr Trp
1               5

(2) INFORMATION FOR SEQ ID NO:27:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:27:

Trp Phe Asn Tyr Tyr Trp
1               5

( 2 ) INFORMATION FOR SEQ ID NO:28:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:28:

Trp Phe Phe Asn Tyr Trp
1               5

( 2 ) INFORMATION FOR SEQ ID NO:29:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:29:

Trp Phe Phe Tyr Tyr Trp
1               5

( 2 ) INFORMATION FOR SEQ ID NO:30:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:30:

Phe Phe Asn Tyr Tyr Trp
1               5

( 2 ) INFORMATION FOR SEQ ID NO:31:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: circular ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:31:

Gly Asn Trp His Gly Thr Ala Pro Asp
1               5

( 2 ) INFORMATION FOR SEQ ID NO:32:

( i ) SEQUENCE CHARACTERISTICS:
( A ) LENGTH: 10 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:32:

Gly Asn Trp His Gly Thr Ala Pro Asp Trp
1               5                   10

( 2 ) INFORMATION FOR SEQ ID NO:33:

( i ) SEQUENCE CHARACTERISTICS:
( A ) LENGTH: 10 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:33:

Gly Asn Trp His Gly Thr Ala Pro Asp Gly
1               5                   10

( 2 ) INFORMATION FOR SEQ ID NO:34:

( i ) SEQUENCE CHARACTERISTICS:
( A ) LENGTH: 15 amino acids
( B ) TYPE: amino acid
( C ) STRANDEDNESS: single
( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:34:

Gly Asn Trp His Gly Thr Ala Pro Asp Trp Phe Phe Asn Tyr Tyr
1               5                   10                  15

( 2 ) INFORMATION FOR SEQ ID NO:35:

( i ) SEQUENCE CHARACTERISTICS:
- ( A ) LENGTH: 17 amino acids
- ( B ) TYPE: amino acid
- ( C ) STRANDEDNESS: single
- ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:35:

```
Gly Asn Trp His Gly Thr Ala Pro Asp Trp Phe Phe Asn Tyr Tyr Trp
1               5                   10                  15
Trp
```

( 2 ) INFORMATION FOR SEQ ID NO:36:

( i ) SEQUENCE CHARACTERISTICS:
- ( A ) LENGTH: 20 amino acids
- ( B ) TYPE: amino acid
- ( C ) STRANDEDNESS: single
- ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:36:

```
Gly Asn Trp His Gly Thr Ala Pro Asp Trp Phe Phe Asn Tyr Tyr Trp
1               5                   10                  15
Asn Tyr Tyr Trp
            20
```

( 2 ) INFORMATION FOR SEQ ID NO:37:

( i ) SEQUENCE CHARACTERISTICS:
- ( A ) LENGTH: 26 amino acids
- ( B ) TYPE: amino acid
- ( C ) STRANDEDNESS: single
- ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:37:

```
Gly Asn Trp His Gly Thr Ala Pro Asp Trp Phe Phe Asn Tyr Tyr Trp
1               5                   10                  15
Val Tyr Phe Ala His Leu Asp Ile Ile Trp
                20                  25
```

( 2 ) INFORMATION FOR SEQ ID NO:38:

( i ) SEQUENCE CHARACTERISTICS:
- ( A ) LENGTH: 16 amino acids
- ( B ) TYPE: amino acid
- ( C ) STRANDEDNESS: single
- ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:38:

```
Gly Asn Trp His Gly Thr Ala Pro Asp Trp Phe Phe Asn Tyr Tyr Ala
1               5                   10                  15
```

( 2 ) INFORMATION FOR SEQ ID NO:39:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:39:

```
Gly Asn Trp His Gly Thr Ala Pro Asp Trp Phe Phe Asn Tyr Tyr Phe
1               5                   10                  15
```

( 2 ) INFORMATION FOR SEQ ID NO:40:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:40:

```
Gly Asn Trp His Gly Thr Ala Pro Asp Trp Phe Phe Asn Tyr Tyr Tyr
1               5                   10                  15
```

( 2 ) INFORMATION FOR SEQ ID NO:41:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:41:

```
Gly Asn Trp His Gly Thr Ala Pro Asp Trp Phe Phe Asn Tyr Tyr Asn
1               5                   10                  15

Tyr Tyr Trp
```

( 2 ) INFORMATION FOR SEQ ID NO:42:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:42:

Gly  Asn  Trp  His  Gly  Thr  Ala  Pro  Asp  Trp  Val  Tyr  Phe  Ala  His  Leu
   1                   5                        10                       15
   Asp  Ile  Ile  Trp
                  20

( 2 ) INFORMATION FOR SEQ ID NO:43:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:43:

Gly  Asn  Trp  His  Gly  Thr  Ala  Pro  Asp  Trp  Val  Tyr  Phe  Ala  His  Leu
   1                   5                        10                       15
   Asp  Ile  Ile  Trp
                  20

( 2 ) INFORMATION FOR SEQ ID NO:44:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:44:

Gly  Asn  Trp  His  Gly  Thr  Ala  Pro  Asp  Trp  Ile  Ile  Trp
   1                   5                        10

( 2 ) INFORMATION FOR SEQ ID NO:45:

( i ) SEQUENCE CHARACTERISTICS:
      ( A ) LENGTH: 20 amino acids
      ( B ) TYPE: amino acid
      ( C ) STRANDEDNESS: single (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:45:

```
Gly Asn Trp His Gly Thr Ala Pro Asp Trp Leu Tyr Phe Ala His Gln
1               5                   10                  15
Asp Val Ile Trp
            20
```

(2) INFORMATION FOR SEQ ID NO:46:

(i) SEQUENCE CHARACTERISTICS:
(A) LENGTH: 10 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:46:

```
Gly Asn Trp His Gly Thr Ala Pro Asp Ala
1               5                   10
```

(2) INFORMATION FOR SEQ ID NO:47:

(i) SEQUENCE CHARACTERISTICS:
(A) LENGTH: 10 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:47:

```
Gly Asn Trp His Gly Thr Ala Pro Asp Val
1               5                   10
```

(2) INFORMATION FOR SEQ ID NO:48:

(i) SEQUENCE CHARACTERISTICS:
(A) LENGTH: 11 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:48:

```
        Gly  Asn  Trp  His  Gly  Thr  Ala  Pro  Asp  Trp  Gly
         1             5                        10
```

(2) INFORMATION FOR SEQ ID NO:49:

(i) SEQUENCE CHARACTERISTICS:
        (A) LENGTH: 14 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:49:

```
        Gly  Asn  Trp  His  Gly  Thr  Ala  Pro  Asp  Trp  Asn  Tyr  Tyr  Trp
         1             5                        10
```

(2) INFORMATION FOR SEQ ID NO:50:

(i) SEQUENCE CHARACTERISTICS:
        (A) LENGTH: 20 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:50:

```
        Gly  Asn  Trp  His  Gly  Thr  Ala  Pro  Asp  Trp  Val  Tyr  Phe  Ala  Phe  Phe
         1             5                        10                       15
        Asn  Tyr  Tyr  Trp
                      20
```

(2) INFORMATION FOR SEQ ID NO:51:

(i) SEQUENCE CHARACTERISTICS:
        (A) LENGTH: 20 amino acids
        (B) TYPE: amino acid
        (C) STRANDEDNESS: single
        (D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:51:

```
        Gly  Asn  Trp  His  Gly  Thr  Ala  Pro  Asp  Trp  Val  Tyr  Tyr  Ala  His  Leu
         1             5                        10                       15
        Asp  Ile  Ile  Trp
                      20
```

(2) INFORMATION FOR SEQ ID NO:52:

(i) SEQUENCE CHARACTERISTICS:

(A) LENGTH: 17 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:52:

```
Gly Asn Trp His Gly Thr Ala Pro Asp Trp Ala His Leu Asp Ile Ile
1               5                   10                  15
Trp
```

(2) INFORMATION FOR SEQ ID NO:53:

(i) SEQUENCE CHARACTERISTICS:
(A) LENGTH: 16 amino acids
(B) TYPE: amino acid
(C) STRANDEDNESS: single
(D) TOPOLOGY: both (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:53:

```
Gly Asn Trp His Gly Thr Ala Ala Asp Trp Phe Phe Asn Tyr Tyr Trp
1               5                   10                  15
```

(2) INFORMATION FOR SEQ ID NO:54:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:54:

```
Gly Asn Trp His Gly Thr Ala Pro Asp Trp Val Tyr Tyr Ala His Leu
1               5                   10                  15
Asp Ile Ile Trp
            20
```

(2) INFORMATION FOR SEQ ID NO:55:

(i) SEQUENCE CHARACTERISTICS:
(A) LENGTH: 20 amino acids
(B) TYPE: amino acid
(C) STRANDEDNESS: single
(D) TOPOLOGY: linear (ii) MOLECULE TYPE: peptide (iii) HYPOTHETICAL: NO ( i v ) ANTI-SENSE: NO ( v ) FRAGMENT TYPE: N-terminal ( x i ) SEQUENCE DESCRIPTION: SEQ ID NO:55:

```
Gly Asn Trp His Gly Thr Ala Pro Asp Trp Leu Tyr Phe Ala His Gln
1               5                   10                  15
Asp Val Ile Trp
            20
```

( 2 ) INFORMATION FOR SEQ ID NO:56:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:56:

```
Gly Asn Trp His Gly Thr Ala Pro Asp Trp Phe Phe Asn Tyr Tyr Asn
1               5                   10                  15
Ile Ile Trp
```

( 2 ) INFORMATION FOR SEQ ID NO:57:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:57:

```
Gly Asn Trp His Gly Thr Ala Pro Asp Trp Phe Phe Asn Tyr Tyr Ala
1               5                   10                  15
His Leu Asp Ile Ile Trp
            20
```

( 2 ) INFORMATION FOR SEQ ID NO:58:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:58:

Gly Asp Trp His Gly Thr Ala Pro Asp Trp Val Tyr Phe Ala His Leu
1               5                   10                  15
Asp Ile Ile Trp
            20

( 2 ) INFORMATION FOR SEQ ID NO:59:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:59:

Gly Asn Trp Lys Gly Thr Ala Pro Asp Trp Val Tyr Phe Ala His Leu
1               5                   10                  15
Asp Ile Ile Trp
            20

( 2 ) INFORMATION FOR SEQ ID NO:60:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:60:

Gly Asp Trp His Gly Thr Ala Pro Asp Trp Val Tyr Phe Ala His Leu
1               5                   10                  15
Asp Ile Ile Trp
            20

( 2 ) INFORMATION FOR SEQ ID NO:61:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:61:

Gly Asn Trp Lys Gly Thr Ala Pro Asp Trp Val Tyr Phe Ala His Leu
1               5                   10                  15
Asp Ile Ile Trp
            20

( 2 ) INFORMATION FOR SEQ ID NO:62:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:62:

```
Gly  Asn  Trp  His  Gly  Thr  Ala  Pro  Asp  Trp  Phe  Phe  Asn  Tyr  Tyr  Xaa
1                   5                        10                       15
```

( 2 ) INFORMATION FOR SEQ ID NO:63:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:63:

```
Gly  Asn  Trp  His  Gly  Thr  Ala  Pro  Asp  Trp  Phe  Phe  Asn  Tyr  Tyr  Trp
1                   5                        10                       15
```

( 2 ) INFORMATION FOR SEQ ID NO:64:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:64:

```
Gly  Asn  Trp  His  Gly  Thr  Ala  Pro  Asp  Trp  Phe  Phe  Asn  Tyr  Tyr  Trp
1                   5                        10                       15
```

( 2 ) INFORMATION FOR SEQ ID NO:65:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:65:

Gly Asn Trp His Gly Thr Ala Pro Asp Trp Phe Phe Asn Tyr Tyr Trp
1               5                   10                  15

( 2 ) INFORMATION FOR SEQ ID NO:66:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:66:

Gly Asn Trp His Gly Thr Ala Pro Asp Trp Phe Phe Asn Tyr Tyr Xaa
1               5                   10                  15

( 2 ) INFORMATION FOR SEQ ID NO:67:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:67:

Gly Asn Trp His Gly Thr Ala Pro Asp Trp
1               5                   10

( 2 ) INFORMATION FOR SEQ ID NO:68:

( i ) SEQUENCE CHARACTERISTICS:
    ( A ) LENGTH: 16 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:68:

Gly Asn Trp His Gly Thr Ala Pro Asp Trp Phe Phe Asn Tyr Tyr Trp
1               5                   10                  15

( 2 ) INFORMATION FOR SEQ ID NO:69:

( i ) SEQUENCE CHARACTERISTICS:
    ( A ) LENGTH: 15 amino acids (B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:69:

```
Gly Asn Trp His Gly Thr Ala Pro Asp Trp Phe Phe Asn Tyr Tyr
1               5                   10                  15
```

(2) INFORMATION FOR SEQ ID NO:70:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:70:

```
Trp Phe Phe Asn Tyr Tyr Trp
1               5
```

(2) INFORMATION FOR SEQ ID NO:71:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:71:

```
Val Tyr Phe Ala His Leu Asp Ile Ile Trp
1               5                   10
```

(2) INFORMATION FOR SEQ ID NO:72:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:72:

```
        Val  Tyr  Phe  Ala  His  Leu  Asp  Ile  Ile
        1                   5
```

( 2 ) INFORMATION FOR SEQ ID NO:73:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:73:

```
        Leu  Tyr  Phe  Ala  His  Gln  Asp  Val  Ile  Trp
        1                   5                        10
```

( 2 ) INFORMATION FOR SEQ ID NO:74:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:74:

```
        Val  Tyr  Phe  Ala  Phe  Phe  Asn  Tyr  Tyr  Trp
        1                   5                        10
```

( 2 ) INFORMATION FOR SEQ ID NO:75:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:75:

```
        Val  Tyr  Tyr  Ala  His  Leu  Asp  Ile  Ile  Trp
        1                   5                        10
```

( 2 ) INFORMATION FOR SEQ ID NO:76:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:76:

Val Tyr Tyr Ala His Leu Asp Ile Ile
1               5

( 2 ) INFORMATION FOR SEQ ID NO:77:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:77:

Ala His Leu Asp Ile Ile
1               5

( 2 ) INFORMATION FOR SEQ ID NO:78:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:78:

Trp Phe Phe Asn Tyr Tyr
1               5

( 2 ) INFORMATION FOR SEQ ID NO:79:

( i ) SEQUENCE CHARACTERISTICS:
( A ) LENGTH: 7 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:79:

Trp Phe Phe Asn Tyr Tyr Trp
1               5

( 2 ) INFORMATION FOR SEQ ID NO:80:

( i ) SEQUENCE CHARACTERISTICS:
     ( A ) LENGTH: 16 amino acids
     ( B ) TYPE: amino acid
     ( C ) STRANDEDNESS: single
     ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:80:

```
Gly Asn Trp His Gly Thr Ala Ala Asp Trp Phe Phe Asn Tyr Tyr Trp
 1               5                  10                 15
```

( 2 ) INFORMATION FOR SEQ ID NO:81:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:81:

```
Asn Ile Ile Trp
 1
```

( 2 ) INFORMATION FOR SEQ ID NO:82:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:82:

```
Ala His Leu Asp Ile Ile Trp
 1               5
```

( 2 ) INFORMATION FOR SEQ ID NO:83:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:83:

Gly Asp Trp His Gly Thr Ala
1               5

( 2 ) INFORMATION FOR SEQ ID NO:84:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:84:

Gly Asp Trp His Gly Thr Ala Pro Asp Trp
1               5                   1 0

( 2 ) INFORMATION FOR SEQ ID NO:85:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:85:

Gly Asp Trp His Gly Thr Ala Pro Asp Trp
1               5                   1 0

( 2 ) INFORMATION FOR SEQ ID NO:86:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:86:

Gly Asn Trp Lys Gly Thr Ala
1               5

( 2 ) INFORMATION FOR SEQ ID NO:87:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:87:

```
Gly  Asn  Trp  Lys  Gly  Thr  Ala  Pro  Asp  Trp
1                   5                        10
```

( 2 ) INFORMATION FOR SEQ ID NO:88:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: both ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:88:

```
Gly  Asn  Trp  Lys  Gly  Thr  Ala  Pro  Asp  Trp
1                   5                        10
```

( 2 ) INFORMATION FOR SEQ ID NO:89:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:89:

```
Gly  Asn  Trp  His  Gly  Thr  Ala  Pro
1                   5
```

( 2 ) INFORMATION FOR SEQ ID NO:90:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:90:

```
Val  Tyr  Phe  Ser  His  Leu  Asp  Ile  Ile  Trp
1                   5                        10
```

(2) INFORMATION FOR SEQ ID NO:91:

(i) SEQUENCE CHARACTERISTICS:
    (A) LENGTH: 8 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:91:

Gly  Asn  Trp  His  Gly  Thr  Ala  Ala
    1                   5

(2) INFORMATION FOR SEQ ID NO:92:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:92:

Leu  Tyr  Phe  Ala  His  Gln  Asp  Val  Ile
    1                   5